(12) United States Patent
Defougerolles et al.

(10) Patent No.: US 8,507,663 B2
(45) Date of Patent: Aug. 13, 2013

(54) COMPOSITIONS AND METHODS FOR INHIBITING EXPRESSION OF CD274/PD-L1 GENE

(75) Inventors: Antonin Defougerolles, Cambridge, MA (US); Tatiana Novobrantseva, Cambridge, MA (US); Brian Bettencourt, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/081,270

(22) Filed: Apr. 6, 2011

(65) Prior Publication Data

US 2011/0251259 A1    Oct. 13, 2011

Related U.S. Application Data

(60) Provisional application No. 61/321,263, filed on Apr. 6, 2010.

(51) Int. Cl.
| | |
|---|---|
| *C07H 21/04* | (2006.01) |
| *C07H 21/02* | (2006.01) |
| *A61K 48/00* | (2006.01) |
| *C12N 15/63* | (2006.01) |

(52) U.S. Cl.
USPC ......... 536/24.5; 536/23.1; 514/44; 435/320.1

(58) Field of Classification Search
None
See application file for complete search history.

(56) References Cited

U.S. PATENT DOCUMENTS

| 2006/0003322 A1 | 1/2006 | Bentwich |
| 2008/0027019 A1 | 1/2008 | Vickers et al. |
| 2010/0035973 A1 | 2/2010 | Walker |

FOREIGN PATENT DOCUMENTS

| WO | 99/61631 | 5/1999 |
| WO | 99/32619 | 7/1999 |
| WO | 99/53050 | 10/1999 |
| WO | 00/44895 | 8/2000 |

OTHER PUBLICATIONS

Barber DL et al. 2006. Nature 439:682-87.
Beswick EJ, et al. 2007. Infect. Immun. 75:4334-41.
Blank C et al. 2003. J. Immunol. 171:4574-81.
Boettler T et al. 2006. J. Virol. 80:3532-40.
Boni C et al. 2007. J. Virol. 81:4215-25.
Breton et al., "siRNA knockdown of PD-L1 and PD-l2 in monocyte-derived dendritic cells only modestly improves proliferative responses to Gag by CD8(+) T cells from HIV-1-infected individuals," J. Clin. Immunol., Sep. 2009, vol. 29, No. 5, pp. 637-645.
Brown JA et al., 2003. J. Immunol. 170:1257-66.
Chemnitz JM et al. 2007. Blood 110:3226-33.
Chen L et al. 2007. J. Immunol. 178:6634-41.
Curiel TJ et al. 2003. Nat. Med. 9:562-67.
Das S et al. 2006. J. Immunol. 176:3000-9.
Day CL et al. 2006. Nature 443:350-54.
Dong H et al. 2002. Nat. Med. 8:793-800.
Dorfman DM et al. 2006. Am. J. Surg. Pathol. 30:802-10.
Elbashir et al., EMBO 2001, 20:6877-6888.
Flies DB and Chen L 2007: J Immunother. 30 (3): 251-60.
Geng L et al. 2006. J. Viral Hepat. 13:725-33.
Gotsman I et al. 2007. J. Clin. Invest. 117:2974-82.
Hamanishi J, et al. 2007. Proc. Natl. Acad. Sci. USA 104:3360-65.
Hirano F et al. 2005. Cancer Res.65:1089-96.
Inman BA et al. 2007. Cancer 109:1499-505.
Keir ME et al., 2008. Annu Rev Immunol. 26:677-704.
Konishi J et al. 2004. Clin. Cancer Res. 10:5094-100.
Liu J et al. 2007.Blood 110:296-304.
Loke P and Allison JP, 2003: Proc. Natl. Acad. Sci. U.S.A. 100 (9): 5336-41.
Nakanishi J et al. 2007. Cancer Immunol. Immunother. 56:1173-82.
Nomi T et al. 2007. Clin. Cancer Res. 13:2151-57.
Parsa AT et al. 2007. Nat. Med. 13:84-88.
Petrovas C et al. 2006. J. Exp. Med. 203:2281-92.
Sharma MD et al. 2007. J. Clin. Invest. 117:2570-82.
Shimauchi T et al. 2007. Int. J. Cancer 121: 2585-90.
Smith P et al. 2004. J. Immunol. 173:1240-48.
Strome SE et al. 2003. Cancer Res. 63:6501-5.
Terrazas LI et al. 2005. Int. J. Parasitol. 35:1349-58.
Thompson RH et al. 2004. Proc. Natl. Acad. Sci. USA 101:17174-79.
Trabattoni D et al. 2003. Blood101:2514-20.
Trautmann L et al. 2006. Nat. Med. 12:1198-202.
Urbani S et al. 2006. J. Virol. 80:11398-40.
Velu V et al. 2007. J. Virol.81:5819-28.
Wherry EJ and Ahmed R. 2004. J. Virol. 78:5535-45.
Wu C, Zhu Y, Jiang J, Zhao J, Zhang XG, Xu N. 2006. Acta Histochem. 108:19-24.
Yang, D., et al., Curr. Biol. (2000) 10:1191-1200.
Yao ZQ et al. 2007. Viral Immunol. 20:276-87.
Genbank NM_014143.2 *Homo sapiens* CD274 molecule (CD274), mRNA, Mar. 5, 2010.

*Primary Examiner* — Amy Bowman
(74) *Attorney, Agent, or Firm* — David S. Resnick; Mark J. FitzGerald; Nixon Peabody LLP

(57) ABSTRACT

The invention relates to double-stranded ribonucleic acid (dsRNA) compositions targeting the CD274/PD-L1 gene, and methods of using such dsRNA compositions to inhibit expression of CD274/PD-L1.

16 Claims, 6 Drawing Sheets

Figure 1. SEQ ID NO. 869 (Human CD274/PD-L1 mRNA sequence)

```
   1 cgaggctccg caccagccgc gcttctgtcc gcctgcaggg cattccagaa agatgaggat
  61 atttgctgtc tttatattca tgacctactg gcatttgctg aacgcattta ctgtcacggt
 121 tcccaaggac ctatatgtgg tagagtatgg tagcaatatg acaattgaat gcaaattccc
 181 agtagaaaaa caattagacc tggctgcact aattgtctat tgggaaatgg aggataagaa
 241 cattattcaa tttgtgcatg gagaggaaga cctgaaggtt cagcatagta gctacagaca
 301 gagggccgg ctgttgaagg accagctctc cctgggaaat gctgcacttc agatcacaga
 361 tgtgaaattg caggatgcag gggtgtaccg ctgcatgatc agctatggtg gtgccgacta
 421 caagcgaatt actgtgaaag tcaatgcccc atacaacaaa atcaaccaaa gaattttggt
 481 tgtggatcca gtcacctctg aacatgaact gacatgtcag gctgagggct accccaaggc
 541 cgaagtcatc tggacaagca gtgaccatca agtcctgagt ggtaagacca ccaccaccaa
 601 ttccaagaga gaggagaagc ttttcaatgt gaccagcaca ctgagaatca acacaacaac
 661 taatgagatt ttctactgca cttttaggag attagatcct gaggaaaacc atacagctga
 721 attggtcatc ccagaactac ctctggcaca tcctccaaat gaaaggactc acttggtaat
 781 tctgggagcc atcttattat gccttggtgt agcactgaca ttcatcttcc gtttaagaaa
 841 agggagaatg atggatgtga aaaatgtgg catccaagat acaaactcaa agaagcaaag
 901 tgatacacat ttggaggaga cgtaatccag cattggaact tctgatcttc aagcagggat
 961 tctcaacctg tggtttaggg gttcatcggg gctgagcgtg acaagaggaa ggaatgggcc
1021 cgtgggatgc aggcaatgtg ggacttaaaa ggcccaagca ctgaaaatgg aacctggcga
1081 aagcagagga ggagaatgaa gaaagatgga gtcaaacagg gagcctggag ggagaccttg
1141 atactttcaa atgcctgagg ggctcatcga cgcctgtgac agggagaaag gatacttctg
1201 aacaaggagc ctccaagcaa atcatccatt gctcatccta ggaagacggg ttgagaatcc
1261 ctaatttgag ggtcagttcc tgcagaagtg cccttttgcct ccactcaatg cctcaatttg
1321 ttttctgcat gactgagagt ctcagtgttg gaacgggaca gtatttatgt atgagttttt
1381 cctatttatt ttgagtctgt gaggtcttct tgtcatgtga gtgtggttgt gaatgatttc
1441 ttttgaagat atattgtagt agatgttaca attttgtcgc caaactaaac ttgctgctta
1501 atgatttgct cacatctagt aaaacatgga gtatttgtaa aaaaaaaaaa aaa
```

Figure 2. SEQ ID NO. 870 (Mouse CD274/PD-L1 mRNA Sequence)

```
   1 gaaatcgtgg tccccaagcc tcatgccagg ctgcacttgc acgtcgcggg ccagtctcct
  61 cgcctgcaga tagttcccaa aacatgagga tatttgctgg cattatattc acagcctgct
 121 gtcacttgct acgggcgttt actatcacgg ctccaaagga cttgtacgtg gtggagtatg
 181 gcagcaacgt cacgatggag tgcagattcc ctgtagaacg ggagctggac ctgcttgcgt
 241 tagtggtgta ctgggaaaag gaagatgagc aagtgattca gtttgtggca ggagaggagg
 301 accttaagcc tcagcacagc aacttcaggg ggagagcctc gctgccaaag gaccgcttt
 361 tgaagggaaa tgctgccctt cagatcacac acgtcaagct gcaggacgca ggcgtttact
 421 gctgcataat cagctacggt ggtgcggact acaagcgaat cacgctgaaa gtcaatgccc
 481 catacccgca aatcaaccag agaatttccg tggatccagc cacttctgag catgaactaa
 541 tatgtcaggc cgagggttat ccagaagctg aggtaatctg acaaacagt gaccaccaac
 601 ccgtgagtgg gaagagaagt gtcaccactt cccggacaga ggggatgctt ctcaatgtga
 661 ccagcagtct gagggtcaac gccacagcga atgatgtttt ctactgtacg ttttggagat
 721 cacagccagg gcaaaaccac acagcggagc tgatcatccc agaactgcct gcaacacatc
 781 ctccacagaa caggactcac tgggtgcttc tgggatccat cctgttgttc ctcattgtag
 841 tgtccacggt cctcctcttc ttgagaaaac aagtgagaat gctagatgtg gagaaatgtg
 901 gcgttgaaga tacaagctca aaaaacgaa atgatacaca attcgaggag acgtaagcag
 961 tgttgaaccc tctgatcgtc gattggcagc ttgtggtctg tgaaagaaag ggccatggg
1021 acatgagtcc aaagactcaa gatggaacct gagggagaga accaagaaag tgttgggaga
1081 ggagcctgga acaacggaca ttttttccag ggagacactg ctaagcaagt tgcccatcag
1141 tcgtcttggg aaatggattg agggttcctg gcttagcagc tggtccttgc acagtgacct
1201 tttcctctgc tcagtgccgg gatgagagat ggagtcatga gtgttgaaga ataagtgcct
1261 tctatttatt ttgagtctgt gtgttctcac tttgggcatg taattatgac tggtgaattc
1321 tgacgacatg atagatctta agatgtagtc accaaactca actgctgctt agcatcctcc
1381 gtaactactg atacaagcag ggaacacaga ggtcacctgc ttggtttgac aggctcttgc
1441 tgtctgactc aaataatctt tattttcag tcctcaaggc tcttcgatag cagttgttct
1501 gtatcagcct tataggtgtc aggtatagca ctcaacatct catctcatta caatagcaac
1561 cctcatcacc atagcaacag ctaacctctg ttatcctcac ttcatagcca ggaagctgag
1621 cgactaagtc acttgcccac agagtatcag ctctcagatt tctgttcttc agccactgtc
1681 ctttcaggat agaatttgtc gttaagaaat taatttaaaa actgattatt gagtagcatt
1741 gtatatcaat cacaacatgc cttgtgcact gtgctggcct ctgagcataa agatgtacgc
1801 cggagtaccg gtcggacatg tttatgtgtg ttaaatactc agagaaatgt tcattaacaa
1861 ggagcttgca ttttagagac actggaaagt aactccagtt cattgtctag cattacattt
1921 acctcatttg ctatccttgc catacagtct cttgttctcc atgaagtgtc atgaatcttg
1981 ttgaatagtt cttttatttt ttaaatgttt ctatttaaat gatattgaca tctgaggcga
2041 tagctcagtt ggtaaaaccc tttcctcaca agtgtgaaac cctgagtctt atccctagaa
2101 cccacataaa aaacagttgc gtatctttgt gcatgctttt gatcccagca ctagggaggc
2161 agaggcaggc agatcctgag ctctcattga ccacccagcc tagcctacat ggttagctcc
2221 aggcctacag gagctggcag agcctgaaaa acgatgccta gacacacaca cacacacaca
2281 cacacacaca cacacacaca cacaccatgt actcatagac ctaagtgcac cctcctacac
2341 atgcacacac atacaattca aacacaaatc aacaggaat tgtctcagaa tggtcccaa
2401 gacaaagaag aagaaaaaca ccaaaccagc tctattccct cagcctatcc tctctactcc
2461 ttcctagaag caactactat tgttttgta tataaattta cccaacgaca gttaatatgt
2521 agaatatata ttaaagtgtc tgtcaatata tattatctct ttctttcttt cttccttct
2581 ttctttcttt ctttcttct ttctttcttt ctttcttct ttcttcctt cttccttcct
2641 tccttccttc cttccttcct ttctttcttt ctttctttct ttctgtctat ctgtacctaa
2701 atggttgctc actatgcatt ttctgtgctc ttcgcccttt ttatttaatg tatggatatt
2761 tatgctgctt ccagaatgga tctaaagctc tttgtttcta gttttctcc cccatccttc
2821 taggcatctc tcacactgtc taggccagac accatgtctg ctgctgaat ctgtagacac
2881 catttataaa gcacgtactc accgagtttg tatttggctt gttctgtgtc tgattaaagg
2941 gagaccatga gtccccaggg tacactgagt tacccagta caaggggga gccttgtttg
3001 tgtctccatg gcagaagcag gcctggagcc attttggttt cttccttgac ttctctcaaa
3061 cacagacgcc tcacttgctc attacaggtt ctcctttggg aatgtcagca ttgctccttg
3121 actgctggct gccctggaag gagcccatta gctctgtgtg agcccttgac agctactgcc
3181 tctccttacc acaggggcct ctaagatact gttacctaga ggtcttgagg atctgtgttc
```

```
3241 tctgggggga ggaaaggagg aggaacccag aactttctta cagtttcct tgttctgtca
3301 catgtcaaga ctgaaggaac aggctgggct acgtagtgag atcctgtctc aaaggaaaga
3361 cgagcatagc cgaaccccg gtggaaccc ctctgttacc tgttcacaca agcttattga
3421 tgagtctcat gttaatgtct tgtttgtatg aagtttaaga aatatcggg ttgggcaaca
3481 cattctattt attcatttta tttgaaatct taatgccatc tcatggtgtt ggattggtgt
3541 ggcactttat tcttttgtgt tgtgtataac cataaatttt attttgcatc agattgtcaa
3601 tgtattgcat taatttaata aatattttta tttattaaaa aaaaaaaaa aaa
```

Figure 2, continued

Figure 3. SEQ ID NO. 871 (Rat CD274/PD-L1 mRNA Sequence; isoform 1)

```
   1 atgaggatat ttgctgtcct tatagtcaca gcctgcagtc acgtgctagc ggcatttacc
  61 atcacagctc caaaggacct gtacgtggtg gagtatggca gcaatgtcac gatggaatgc
 121 agattcccag tagaacagaa attggacctg cttgccttag tggtgtactg ggaaaaggaa
 181 gacaaggaag ttattcagtt tgtggaggga gaggaggacc tgaagcctca acacagcagc
 241 ttcaggggga gagccttctt gccaaaggac cagcttttga aggggaacgc ggtgcttcag
 301 atcacagatg tcaagctgca ggacgcaggt gtctactgct gcatgatcag ctatgctgga
 361 gcggactaca agcgaatcac attgaaagtc aacgctccat accgcaaaat caaccaaaga
 421 atttccatgg atccagccac ttctgagcat gaactaatgt gccaggctga gggttaccca
 481 gaagccgaag tgatctggac aaacagtgac caccagtccc tgagtgggga aacaactgtc
 541 accacttccc agactgagga gaagcttctc aacgtgacca gcgttctgag ggtcaacgca
 601 acagctaatg atgttttcca ctgtacgttc tggagagtac actcagggga gaaccacacg
 661 gctgaactga tcatcccaga actgcctgta ccacgtctcc cacataacag gacacactgg
 721 gtactcctgg gatccgtcct tttgttcctc atcgtgggt tcaccgtctt cttctgcttg
 781 agaaaacaag tgagaatgct agatgtggaa aaatgcggct tcgaagatag aaattcaaag
 841 aaccgaaatg ttcgaggaga cgtaagcagt gttgaaccct ctgagcctcg aggcgggatt
 901 ggcagcttgt ggtctgtgaa agaaagggcc cgtgggacat gggtccaggg actcaaaaat
 961 ggaaccggag aggagaagag aacaaagaaa gtgttggaag aggagcctgg gacgaaagac
1021 atttctacag gagacactgc taagcaagtt acccatcagt catctcgggc aataagttga
```

Figure 4. SEQ ID NO. 872 (Rat CD274/PD-L1 mRNA Sequence, isoform 2)

```
   1 atgaggatat tgctgtcct tatagtcaca gcctgcagtc acgtgctagc ggcatttacc
  61 atcacagctc caaaggacct gtacgtggtg gagtatggca gcaatgtcac gatggaatgc
 121 agattcccag tagaacagaa attggacctg cttgccttag tggtgtactg ggaaaaggaa
 181 gacaaggaag ttattcagtt tgtggaggga gaggaggacc tgaagcctca acacagcagc
 241 ttcaggggga gagccttctt gccaaaggac cagcttttga aggggaacgc ggtgcttcag
 301 atcacagatg tcaagctgca ggacgcaggt gtctactgct gcatgatcag ctatggtgga
 361 gcggactaca agcgaatcac attgaaagtc aacgctccat accgcaaaat caaccaaaga
 421 atttccatgg atccagccac ttctgagcat gaactaatgt gccaggctga gggttaccca
 481 gaagccgaag tgatctggac aaacagtgac caccagtccc tgagtgggga acaactgtc
 541 accacttccc agactgagga gaagcttctc aacgtgacca gcgttctgag ggtcaacgca
 601 acagctaatg atgttttcca ctgtacgttc tggagagtac actcagggga gaaccacacg
 661 gctgaactga tcatcccaga actgcctgta ccacgtctcc cacataacag gacacactgg
 721 gtactcctgg gatccgtcct tttgttcctc atcgtggggt tcaccgtctt cttctgcttg
 781 agaaaacaag tgagaatgct agatgtggaa aaatgcggct tcgaagatag aaattcaaag
 841 aaccgaaatg ttcgaggaga cgtaagcagt gttgaaccct ctgagcctcg aggcgggatt
 901 ggcagcttgt ggtctgtgaa agaaagggcc cgtgggacat gggtccaggg actcaaaaat
 961 ggaaccggag aggagaagag aacaaagaaa gtgttggaag aggagcctgg gacgaaagac
1021 atttctacag gagacactgc taagcaagtt acccatcagt catctcgggc aataagttga
```

5A

5B

COMPOSITIONS AND METHODS FOR INHIBITING EXPRESSION OF CD274/PD-L1 GENE

CROSS-REFERENCE TO RELATED APPLICATIONS

This application claims benefit under 35 U.S.C. §119(e) of U.S. Provisional Patent Application Ser. No. 61/321,263 filed on 6 Apr. 2010, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 20, 2011, is named 051058US.txt and is 272,119 bytes in size.

FIELD OF THE INVENTION

The invention relates to the specific inhibition of the expression of the CD274/PD-L1 gene.

BACKGROUND OF THE INVENTION

CD274 or PD-L1 is a 290 amino acid type I transmembrane protein encoded by the CD274 gene on mouse chromosome 19 and human chromosome 9. CD274/PD-L1 expression is implicated in evasion of immune responses involved in chronic infection, e.g., by viruses (including, for example, HIV, HBV, HCV and HTLV, among others), by bacteria (including, for example, *Helicobacter pylori*, among others) and by parasites (including, for example, *Schistosoma mansoni*).

CD274/PD-L1 expression is also implicated in suppression of anti-tumor immune activity. Tumors express antigens that can be recognized by host T cells, but immunologic clearance of tumors is rare. Part of this failure is due to immune suppression by the tumor microenvironment. PD-L1 expression on many tumors is a component of this suppressive milieu and may act in concert with other immunosuppressive signals. PD-L1 expression has been shown in situ on a wide variety of solid tumors including breast, lung, colon, ovarian, melanoma, bladder, liver, salivary, stomach, gliomas, thyroid, thymic epithelial, head, and neck (Brown J A et al., 2003. J. Immunol. 170:1257-66; Dong H et al. 2002. Nat. Med. 8:793-800; Hamanishi J, et al. 2007. Proc. Natl. Acad. Sci. USA 104:3360-65; Strome S E et al. 2003. Cancer Res. 63:6501-5; Inman B A et al. 2007. Cancer 109:1499-505; Konishi J et al. 2004. Clin. Cancer Res. 10:5094-100; Nakanishi J et al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, PD-1 expression is upregulated on tumor infiltrating lymphocytes, and this may also contribute to tumor immunosuppression (Blank C et al. 2003. J. Immunol. 171:4574-81). In ovarian cancer, PD-L1 expression is inversely correlated with intraepithelial, but not stromal, infiltrating CD8 T cells, suggesting that PD-L1 inhibits the intratumor migration of CD8 T cells (Hamanishi J et al. 2007. Proc. Natl. Acad. Sci. USA 104:3360-65). Translation of PD-L1 mRNA is enhanced by loss of PTEN and the ensuing activation of Akt, a common event in tumorigenesis (Parsa A T et al. 2007. Nat. Med. 13:84-88). Most importantly, studies relating PD-L1 expression on tumors to disease outcome show that PD-L1 expression strongly correlates with unfavorable prognosis in kidney, ovarian, bladder, breast, gastric, and pancreatic cancer (Hamanishi J et al. 2007. Proc. Natl. Acad. Sci. USA 104:3360-65; Inman B A et al. 2007. Cancer 109:1499-505; Konishi J et al. 2004. Clin. Cancer Res. 10:5094-100; Nakanishi J et al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, these studies suggest that higher levels of PD-L1 expression on tumors may facilitate advancement of tumor stage and invasion into deeper tissue structures.

The PD-1 pathway can also play a role in hematologic malignancies. PD-L1 is expressed on multiple myeloma cells but not on normal plasma cells (Liu J et al. 2007.Blood 110:296-304). PD-L1 is expressed on some primary T cell lymphomas, particularly anaplastic large cell T lymphomas (Brown J A et al., 2003. J. Immunol. 170:1257-66). PD-1 is highly expressed on the T cells of angioimmunoblastic lymphomas, and PD-L1 is expressed on the associated follicular dendritic cell network (Dorfman D M et al. 2006. Am. J. Surg. Pathol. 30:802-10). In nodular lymphocyte-predominant Hodgkin lymphoma, the T cells associated with lymphocytic and/or histiocytic (L&H) cells express PD-1. Microarray analysis using a readout of genes induced by PD-1 ligation suggests that tumor-associated T cells are responding to PD-1 signals in situ in Hodgkin lymphoma (Chemnitz J M et al. 2007. *Blood* 110:3226-33). PD-1 and PD-L1 are expressed on CD4 T cells in HTLV-1-mediated adult T cell leukemia and lymphoma (Shimauchi T et al. 2007. *Int. J. Cancer* 121: 2585-90). These tumor cells are hyporesponsive to TCR signals.

Studies in animal models demonstrate that PD-L1 on tumors inhibits T cell activation and lysis of tumor cells and in some cases leads to increased tumor-specific T cell death (Dong H et al. 2002. *Nat. Med.* 8:793-800; Hirano F et al. 2005. *Cancer Res.* 65:1089-96). Tumor-associated APCs can also utilize the PD-1:PD-L pathway to control antitumor T cell responses. PD-L1 expression on a population of tumor-associated myeloid DCs is upregulated by tumor environmental factors (Curiel T J et al. 2003. *Nat. Med.* 9:562-67). Plasmacytoid dendritic cells (DCs) in the tumor-draining lymph node of B16 melanoma express IDO, which strongly activates the suppressive activity of regulatory T cells. The suppressive activity of IDO-treated regulatory T cells required cell contact with IDO-expressing DCs (Sharma M D et al. 2007. *J. Clin. Invest.* 117:2570-82).

SUMMARY OF THE INVENTION

Described herein are compositions and methods that effect the RNA-induced silencing complex (RISC)-mediated cleavage of RNA transcripts of the CD274/PD-L1 gene, such as in a cell or mammal. Also described are compositions and methods for treating pathological conditions and diseases caused by the expression of a CD274/PD-L1 gene, such as a tumor or hematological malignancy (e.g., ovarian cancer or melanoma), or an infectious disease (e.g., viral hepatitis).

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of CD274/PD-L1 expression in a cell or mammal. Alternatively, in another embodiment, an iRNA as described herein activates CD274/PD-L1 expression in a cell or mammal.

The iRNAs included in the compositions featured herein encompass a dsRNA having an RNA strand (the antisense strand) having a region that is 30 nucleotides or less, generally 19-24 nucleotides in length, that is substantially complementary to at least part of an mRNA transcript of a CD274/PD-L1 gene. In one embodiment, the dsRNA comprises a region of at least 15 contiguous nucleotides.

In one embodiment, an iRNA for inhibiting expression of a CD274/PD-L1 gene includes at least two sequences that are complementary to each other. The iRNA includes a sense strand having a first sequence and an antisense strand having a second sequence. The antisense strand includes a nucleotide sequence that is substantially complementary to at least part of an mRNA encoding CD274/PD-L1, and the region of complementarity is 30 nucleotides or less, and at least 15 nucleotides in length. Generally, the iRNA is 19 to 24, e.g., 19 to 21 nucleotides in length. In some embodiments the iRNA is from about 15 to about 25 nucleotides in length, and in other embodiments the iRNA is from about 25 to about 30 nucleotides in length. The iRNA, upon contacting with a cell expressing CD274/PD-L1, inhibits the expression of a CD274/PD-L1 gene by at least 10%, at least 20%, at least 25%, at least 30%, at least 35% or at least 40% or more, such as when assayed by a method as described herein. In one embodiment, the CD274/PD-L1iRNA is formulated in a stable nucleic acid lipid particle (SNALP).

In one embodiment, an iRNA featured herein includes a first sequence of a dsRNA that is selected from the group consisting of the sense sequences of Table 2, Table 3, and Table 5, and a second sequence that is selected from the group consisting of the corresponding antisense sequences of Table 2, Table 3, and Table 5. The iRNA molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such a modified sequence will be based on a first sequence of said iRNA selected from the group consisting of the sense sequences of Table 2, Table 3, and Table 5, and a second sequence selected from the group consisting of the corresponding antisense sequences of Table 2, Table 3, and Table 5.

In one embodiment, an iRNA as described herein targets a wildtype CD274/PD-L1 RNA transcript, and in another embodiment, the iRNA targets a mutant transcript (e.g., a CD274/PD-L1 RNA carrying an allelic variant). For example, an iRNA of the invention can target a polymorphic variant, such as a single nucleotide polymorphism (SNP), of CD274/PD-L1. In another embodiment, the iRNA targets both a wildtype and a mutant CD274/PD-L1 transcript. In yet another embodiment, the iRNA targets a transcript variant of CD274/PD-L1.

In one embodiment, an iRNA featured in the invention targets a non-coding region of a CD274/PD-L1 RNA transcript, such as the 5' or 3' untranslated region.

In one aspect, embodiments of the invention provide a cell containing at least one of the iRNAs featured in the invention. The cell is generally a mammalian cell, such as a human cell. In some embodiments, the cell is a cancer or tumor cell. In some embodiments, the cell is an immune cell.

In another aspect, embodiments of the invention provide a pharmaceutical composition for inhibiting the expression of CD274/PD-L1 gene in an organism, generally a human subject. The composition typically includes one or more of the iRNAs described herein and a pharmaceutically acceptable carrier or delivery vehicle. In one embodiment, the composition is used for treating a cancer or malignancy, such as a myeloma. In one embodiment, the composition is used for treating an infectious disease, such as a viral hepatitis infection.

In another embodiment, the pharmaceutical composition is formulated for administration of a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, one year, or five years, or ten years, or longer, including the remaining lifetime of a subject.

In another embodiment, a composition containing an iRNA described herein, e.g., a dsRNA targeting CD274/PD-L1, is administered with a non-iRNA therapeutic agent, such as an agent known to treat a cancer, or a symptom of a cancer. In another embodiment, a composition containing an iRNA featured in the invention, e.g., a dsRNA targeting CD274/PD-L1, is administered along with a non-iRNA therapeutic regimen, such as immunotherapy. For example, an iRNA featured in the invention can be administered along with vaccination against a tumor peptide antigen agent for treatment of tumor or other malignancy. In another example, an iRNA featured in the invention can be administered along with depletion of a cell population, such as CD4 cells.

In another embodiment, a CD274/PD-L1iRNA is administered to a patient, and then the non-iRNA agent or therapeutic regimen is administered to the patient (or vice versa). In another embodiment, a CD274/PD-L1 iRNA and the non-iRNA therapeutic agent or therapeutic regimen are administered at the same time. In one embodiment, the therapeutic agent is, for example, a tumor peptide antigen agent, such as a myeloma peptide that increases melanoma-specific T cell responses. In another embodiment, the therapeutic regimen includes the depletion of CD4 cells from the patient.

In another aspect, provided herein is a method for inhibiting the expression of a CD274/PD-L1 gene in a cell by performing the following steps:
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding CD274/PD-L1, and where the region of complementarity is 30 nucleotides or less, i.e., 15-30 nucleotides in length, and generally 19-24 nucleotides in length, and where the dsRNA, upon contact with a cell expressing CD274/PD-L1, inhibits expression of a CD274/PD-L1 gene by at least 10%, preferably at least 20%, at least 30%, at least 40% or more; and
(b) maintaining the cell produced in step (a) for a time sufficient to obtain degradation of the mRNA transcript of the CD274/PD-L1 gene, thereby inhibiting expression of a CD274/PD-L1 gene in the cell.

In another aspect, the invention provides methods and compositions useful for activating expression of a CD274/PD-L1 gene in a cell or mammal.

In another aspect, the invention provides a method for modulating the expression of a CD274/PD-L1 gene in a cell by performing the following steps:
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding CD274/PD-L1, and where the region of complementarity is 30 nucleotides or less, i.e., 15-30 nucleotides in length, and generally 19-24 nucleotides in length, and where the dsRNA, upon contact with a cell expressing CD274/PD-L1, modulates expression of a CD274/PD-L1 gene by at least 10%, preferably at least 20%, at least 30%, at least 40% or more; and
(b) maintaining the cell produced in step (a) for a time sufficient to obtain degradation or increased expression of the mRNA transcript of the CD274/PD-L1 gene, thereby modulating expression of a CD274/PD-L1 gene in the cell.

In one embodiment, the method is for inhibiting gene expression in an antigen-presenting cell, a macrophage, a T cell, an NK cell, an NKT cell, a myeloid dendritic cell, a B cell, an epithelial cell, a vascular endothelial cell, or any combination thereof.

In another embodiment, the method is for inhibiting gene expression in a tumor cell, or a lymphoma cell.

In other aspects, the invention provides methods for treating, preventing, reversing, or managing pathological processes mediated by CD274/PD-L1 expression, such as a tumor or other malignancy. In one embodiment, the method includes administering to a patient in need of such treatment, prevention, reversal, or management a therapeutically or prophylactically effective amount of one or more of the iRNAs featured in the invention. In one embodiment, the patient has a tumor or a hematological malignancy. In another embodiment, administration of the iRNA targeting CD274/PD-L1 alleviates or relieves the severity of at least one symptom of a CD274/PD-L1-mediated disorder in the patient, such as high tumor burden, development of metastasis, or tumor or lymphoma cell proliferation.

In one aspect, the invention provides a vector for inhibiting the expression of a CD274/PD-L1 gene in a cell. In one embodiment, the vector includes at least one regulatory sequence operably linked to a nucleotide sequence that encodes at least one strand of an iRNA as described herein. In another such aspect, the invention provides a vector encoding a dsRNA that targets a CD274/PD-L1 mRNA for cleavage, the dsRNA comprising on one strand a region of complementarity to said CD274/PD-L1 mRNA, the region of complementarity providing a double-stranded region of said dsRNA of 30 base pairs or less in length.

In another aspect, the invention provides a cell containing a vector for inhibiting the expression of a CD274/PD-L1 gene in a cell. The vector includes a regulatory sequence operably linked to a nucleotide sequence that encodes at least one strand of one of the iRNAs as described herein.

In yet another aspect, the invention provides a composition containing a CD274/PD-L1 iRNA, in combination with a second iRNA targeting a second gene involved in a pathological disease, and useful for treating the disease, e.g., a tumor or a hematological malignancy. For example, the second gene can be the gene encoding PD-1, i.e., PDCD1.

The details of various embodiments of the invention are set forth in the description below. Other features, objects, and advantages of the invention will be apparent from the description and the drawings, and from the claims.

DESCRIPTION OF THE DRAWINGS

FIG. 1 is the sequence of human CD274/PD-L1 mRNA (Ref. Seq. NM_014143.2, SEQ ID NO: 869).

FIG. 2 is a sequence of mouse CD274/PD-L1 mRNA (Ref. Seq. NM_021893.2; SEQ ID NO: 870).

FIG. 3 is a sequence of rat CD274/PD-L1 mRNA, isoform 1 (Ref. Seq. XM_001079572.1; SEQ ID NO: 871).

FIG. 4 is a sequence of rat CD274/PD-L1 mRNA, isoform 2 (Ref. Seq. XM_574652.2; SEQ ID NO: 872).

DETAILED DESCRIPTION OF THE INVENTION

Figure 5A:
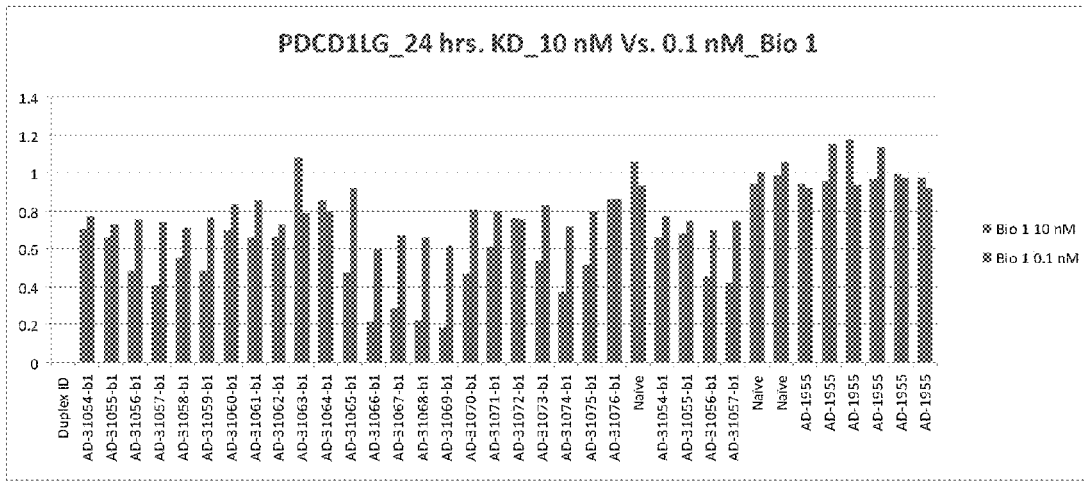
FIGS. 5A-5B depict representative experimental expression data using the various inhibitory duplexes of Table 5 (SEQ ID NOs: 877-924), comparing 0.1 nM and 10 nM concentrations.
Figure 5B:
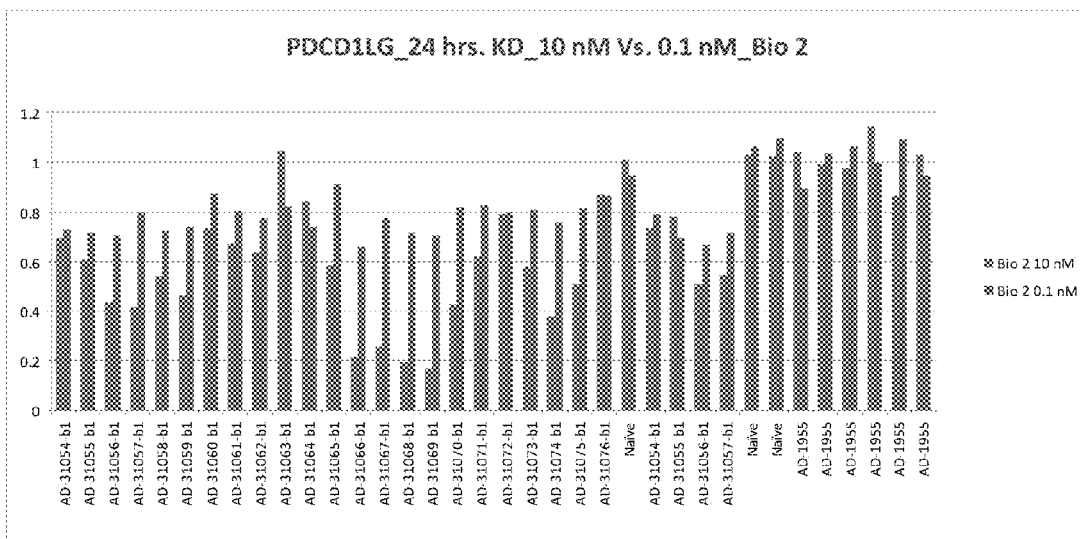

Described herein are iRNAs and methods of using them for inhibiting the expression of a CD274/PD-L1 gene in a cell or a mammal where the iRNA targets a CD274/PD-L1 gene. Also provided are compositions and methods for treating pathological conditions and diseases, such as a cancer or infectious disease, in a mammal caused by or modulated by the expression of a CD274/PD-L1 gene. iRNA directs the sequence-specific degradation of mRNA through a process known as RNA interference (RNAi). In one embodiment, the iRNA activates the expression of a CD274/PD-L1 gene in a cell or mammal, where the iRNA targets a CD274/PD-L1 gene.

CD274/PD-L1

CD274/PD-L1 comprises seven exons, the first of which is noncoding and contains the 5'UTR. The next three exons contain the signal sequence, IgV-like domain, and IgC-like domains, respectively. The transmembrane domain and the intracellular domains are contained in the next two exons (exons 5 and 6). The last exon contains intracellular domain residues plus the 3'UTR. The intracellular domain of CD274/PD-L1 is short, only about 30 aa, and highly conserved in all reported species. There is no known function for the intracellular tail of CD274/PD-L1. There is one reported splice variant of CD274/PD-L1 in humans consisting of a sequence lacking the IgV-like domain encoded in exon 2. This mutant should not be able to bind PD-1, although the function of this splice variant has not yet been reported. No splice variants have been identified for mouse CD274/PD-L1. The binding interface of CD274/PD-L1 to one of its known ligands, PD-1, is via its IgV-like domain (Keir M E et al., 2008. Annu Rev Immunol. 26:677-704).

CD274/PD-L1 has been shown to be constitutively expressed on mouse T and B cells, DCs, macrophages, mesenchymal stem cells, and bone marrow-derived mast cells. CD274/PD-L1 expression is also found on a wide range of nonhematopoietic cells and is upregulated on a number of cell types after activation. Upon IFN-γ stimulation, PD-L1 is expressed on T cells, NK cells, macrophages, myeloid DCs, B cells, epithelial cells, and vascular endothelial cells (Flies D B and Chen L 2007: J Immunother. 30 (3): 251-60). PD-L1 is notably expressed on macrophages. In the mouse, it has been shown that classically activated macrophages (induced by type I helper T cells or a combination of LPS and interferon-gamma) greatly upregulate PD-L1 (Loke P and Allison JP, 2003: Proc. Natl. Acad. Sci. U.S.A. 100 (9): 5336-41). Alternatively, macrophages activated by IL-4 (alternative macrophages), slightly upregulate PD-L1, while greatly upregulating PD-L2. It has been shown by STAT1-deficient knockout mice that STAT1 is mostly responsible for upregulation of PD-L1 on macrophages by LPS or interferon-gamma, but is not at all responsible for its constitutive expression before activation in these mice. Both type I and type II interferons (IFNs) upregulate PD-L1. Analyses of the human CD274/PD-L1 promoter demonstrate that both constitutive and inducible CD274/PD-L1 expression are dependent on two IFN regulatory factor-1 (IRF-1) binding sites that are between 200 and 320 by upstream of the transcriptional start site, and these IRF-1 binding sites are also found in mouse. Several studies have examined which signaling pathways are required for PD-L1 expression by using pharmacological inhibitors. PD-L1 expression in cell lines is decreased when MyD88, TRAF6, and MEK are inhibited. JAK2 has also been implicated in PD-L1 induction. Loss or inhibition of phosphatase and tensin homolog (PTEN), a cellular phosphatase that modifies phosphatidylinositol 3-kinase (PI3K) and Akt signaling, increases post-transcriptional PD-L1 expression in cancers (Keir M E et al., 2008. Annu Rev Immunol. 26:677-704).

PD-L1 can influence immune responses by engaging PD-1 or B7-1 (CD80) and modifying TCR or BCR signaling, but can also deliver signals into PD-L1 expressing cells, i.e., reverse signaling through PD-L1. Surface plasmon resonance studies demonstrate specific and unique interaction between both PD-L1 and B7-1, with an affinity of 1.7 µM, and an affinity of 0.5 µM for the interaction between PD-L1 and PD-1. Chemical cross-linking studies indicate that PD-L1 and B7-1, like PD-L1 and PD-1, can also interact through their IgV-like domains. The PD-L1:B7-1 interface overlaps at least partially with the putative PD-L1:PD-1 interface. B7-1:PD-L1 interactions can induce an inhibitory signal into T cells. Ligation of PD-L1 on CD4 T cells by B7-1, or ligation of B7-1 on CD4 T cells by PD-L1, delivers a functionally significant, inhibitory signal. Because both PD-L1 and B7-1 are expressed on T cells, B cells, DCs, and macrophages, there is the potential for bidirectional interactions between B7-1 and PD-L1 on these cell types. In addition, PD-L1 on nonhematopoietic cells may interact with B7-1 as well as PD-1 on T cells to regulate cells (Keir M E et al., 2008. Annu Rev Immunol. 26:677-704).

PD-1 and its ligands have important roles in regulating immune defenses against microbes that cause acute and chronic infections. The PD-1:PD-L pathway appears to be a key determinant of the outcome of infection, regulating the delicate balance between effective antimicrobial immune defenses and immune-mediated tissue damage.

A number of microorganisms that cause chronic infection appear to have exploited the PD-1:PD-L pathway to evade the immune responses and establish persistent infection. Studies in the lymphocytic choriomeningitis virus (LCMV) model of chronic viral infection were the first to show a role for the PD-1:PD-L pathway during chronic infection (Barber D L et al. 2006. Nature 439:682-87). Viruses that cause chronic infections can render virus-specific T cells nonfunctional and thereby silence the antiviral T cell response (Wherry E J and Ahmed R. 2004. J. Virol. 78:5535-45). Functional dysregulation, or exhaustion, of CD8 T cells is an important reason for ineffective viral control during chronic infections and is characteristic of chronic LCMV infection in mice, as well as of HIV, HBV, HCV, and HTLV infection in humans and SIV infection in primates.

In chronic viral infections in humans, several groups have shown that PD-1 expression is high on HIV-specific (Petrovas C et al. 2006. J. Exp. Med. 203:2281-92; Day C L et al. 2006. Nature 443:350-54; Trautmann L et al. 2006. Nat. Med. 12:1198-202), HBV-specific (Boettler T et al. 2006. J. Virol. 80:3532-40; Boni C et al. 2007. J. Virol. 81:4215-25), and HCV-specific T cells (Urbani S et al. 2006. J. Virol. 80:11398-403). PD-L1 is also upregulated on peripheral blood CD14+ monocytes and myeloid DCs in patients with chronic HBV infection (Chen L et al. 2007. J. Immunol. 178:6634-41; Geng L et al. 2006. J. Viral Hepat. 13:725-33), and on CD14+ cells and T cells in HIV patients (Trabattoni D et al. 2003. Blood 101:2514-20). Blocking PD-1:PD-L interactions in vitro reverses the exhaustion of HIV-specific, HBV-specific (Boni C et al. 2007. J. Virol. 81:4215-25), HCV-specific, and SIV-specific (Velu V et al. 2007. J. Virol. 81:5819-28) CD8 and CD4 T cells and restores proliferation and cytokine production (Petrovas C et al. 2006. J. Exp. Med. 203:2281-92; Day C L et al. 2006. Nature 443:350-54; Trautmann L et al. 2006. Nat. Med. 12:1198-202; Urbani S et al. 2006. J. Virol. 80:11398-403). Recent work shows that the HCV core, a nucleocapsid protein, can upregulate PD-1 and PD-L1 expression on healthy donor T cells and that upregulation of PD-1 is mediated by interaction of the HCV core with the complement receptor C1QBP (Yao Z Q et al. 2007. Viral Immunol. 20:276-87).

The PD-1:PD-L pathway also may play a key role in the chronicity of bacterial infections. *Helicobacter pylori* causes chronic gastritis and gastroduodenal ulcers and is a risk factor for development of gastric cancer. During *H. pylori* infection, T cell responses are insufficient to clear infection, leading to persistent infection. Gastric epithelial cells express MHC class II molecules and are thought to have important APC (antigen-presenting cell) function during *H. pylori* infection. Following exposure to *H. pylori* in vitro or in vivo, PD-L1 also is upregulated on human gastric epithelial cells. Anti-PD-L1 blocking antibodies enhance T cell proliferation and IL-2 production in cultures of gastric epithelial cells exposed to *H. pylori* and CD4 T cells, suggesting that PD-L1 may play an important role in inhibiting T cell responses during *H. pylori* infection (Das S et al. 2006. J. Immunol. 176:3000-9). PD-L1 is upregulated in gastric mucosal biopsies from *H. pylori*-infected individuals, who show a marked increase in the $CD4^+CD25^{hi}FoxP3^+$ cell population. Naive T cells cultured with *H. pylori*-exposed gastric epithelial cells can develop into functional $CD4^+CD25^{hi}FoxP3^+$ regulatory T cells (Beswick E J, et al. 2007. Infect. Immun. 75:4334-41).

Parasitic worms also have exploited the PD-1:PD-L pathway to induce macrophages with strong suppressive function. During *Taenia crassiceps* infection in mice, PD-L1 and PD-L2 are upregulated on activated macrophages, and a high percentage of CD4 T cells express PD-1. Blockade of PD-L1, PD-L2, or PD-1 significantly decreased suppression of in vitro T cell proliferation by macrophages from *Taenia*-infected mice (Terrazas L I et al. 2005. Int. J. Parasitol. 35:1349-58). Similarly, during *Schistosoma mansoni* infection in mice, macrophages express high levels of PD-L1 and more modest levels of PD-L2. Anti-PD-L1 completely abrogated the ability of these macrophages to suppress T cell proliferation in vitro, whereas anti-PD-L2 had no effect. PD-L1 expression on macrophages from infected mice declines after 12 weeks of infection, correlating with a break in T cell anergy (Smith P et al. 2004. J. Immunol. 173:1240-48). Thus, an emerging theme is that PD-L1 and PD-L2 can mediate the suppressive functions of macrophages during parasite infections.

PD-L1 and PD-L2 have distinct roles in the immune response to the protozoan parasite *Leishmania mexicana*. Cd274−/− 129Sv mice showed resistance to *L. mexicana*, whereas Pdcd1lg2−/− mice developed exacerbated disease with increased parasite burdens. Cd274−/− mice exhibited a diminished Th2 response, which may explain the increased resistance of Cd274−/− mice. Pdcd1lg2−/− mice exhibited a marked increase in *L. mexicana*-specific IgM and IgG2a, which may contribute to the exacerbated disease observed in Pdcd1lg2−/− mice. Increased parasite-specific IgG production may suppress the healing response through FcγR ligation on macrophages.

Studies point to a role for PD-L1 in limiting immunopathology. Following infection with LCMV clone 13, WT mice develop a chronic infection, whereas Cd274−/− mice die (Barber D L et al. 2006. *Nature* 439:682-87). Bone marrow chimera studies point to an important role for PD-L1 on non-bone marrow-derived cells in limiting effector T cell responses and immunopathology.

The expression of PD-L1 on vascular endothelial cells has led to the hypothesis that PD-L1 on endothelial cells may regulate the activation of T cells that contact the vessel wall, the extravasation of T cells into tissue, and/or limit detrimental consequences of immunopathology. Cd274−/− Pdcd1lg2−/− mice developed severely increased atherosclerotic lesion burden, suggesting that PD-L1 also may play a significant role in inflammatory diseases in which vascular endothelium and T cells are important for pathogenesis (Gotsman I et al. 2007. *J. Clin. Invest.* 117:2974-82).

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

The iRNAs of the compositions described herein include an RNA strand (the antisense strand) having a region which is 30 nucleotides or less in length, i.e., 15-30 nucleotides in length, generally 19-24 nucleotides in length, which region is substantially complementary to at least part of an mRNA transcript of a CD274/PD-L1 gene. The use of these iRNAs enables the targeted degradation of mRNAs of genes that are implicated in pathologies associated with CD274/PD-L1 expression in mammals. Very low dosages of CD274/PD-L1 iRNAs in particular can specifically and efficiently mediate RNAi, resulting in significant inhibition of expression of a CD274/PD-L1 gene. Using cell-based assays, the present inventors have demonstrated that iRNAs targeting CD274/PD-L1 can specifically and efficiently mediate RNAi, resulting in significant inhibition of expression of a CD274/PD-L1 gene. Thus, methods and compositions including these iRNAs are useful for treating pathological processes that can be mediated by down regulating CD274/PD-L1, such as in the treatment of a cancer, hematological malignancy, or infectious disease, e.g., breast cancer or hepatitis B. The following detailed description discloses how to make and use compositions containing iRNAs to inhibit the expression of a CD274/PD-L1 gene, as well as compositions and methods for treating diseases and disorders caused by or modulated by the expression of this gene.

Embodiments of the pharmaceutical compositions featured in the invention include an iRNA having an antisense strand comprising a region which is 30 nucleotides or less in length, generally 19-24 nucleotides in length, which region is substantially complementary to at least part of an RNA transcript of a CD274/PD-L1 gene, together with a pharmaceutically acceptable carrier. Embodiments of compositions featured in the invention also include an iRNA having an antisense strand having a region of complementarity which is 30 nucleotides or less in length, generally 19-24 nucleotides in length, and is substantially complementary to at least part of an RNA transcript of a CD274/PD-L1 gene.

Accordingly, in some aspects, pharmaceutical compositions containing a CD274/PD-L1 iRNA and a pharmaceutically acceptable carrier, methods of using the compositions to inhibit expression of a CD274/PD-L1 gene, and methods of using the pharmaceutical compositions to treat diseases caused by expression of a CD274/PD-L1 gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, "Programmed Death Ligand-1" ("PD-L1") or "cluster of differentiation 274" ("CD274") refers to a particular polypeptide expressed in a cell. PD-L1 is also known as CD274, B7-H1, PDCD1L1, PDCD1LG1, and PDL1. The sequence of a human CD274/PD-L1 mRNA transcript can be found at NM_014143.2 (SEQ ID NO: 869). The sequence of mouse CD274/PD-L1 mRNA can be found at NM_021893 (SEQ ID NO: 870), and the sequence of rat CD274/PD-L1 mRNA can be found at XM_001079572.1 (SEQ ID NO: 871) or XM_574652.2; (SEQ ID NO: 872).

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of CD274/PD-L1 expression. Alternatively, in another embodiment, an iRNA as described herein activates CD274/PD-L1 expression.

As used herein, "target sequence" refers to a contiguous portion of the nucleotide sequence of an mRNA molecule formed during the transcription of a CD274/PD-L1 gene, including messenger RNA (mRNA) that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all sub-ranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs (bp), while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (an mRNA) refers to a polynucleotide that is substantially complementary to a contiguous portion of the mRNA of interest (e.g., an mRNA encoding CD274/PD-L1). For example, a polynucleotide is complementary to at least a part of a CD274/PD-L1mRNA if the sequence is substantially complementary to a non-interrupted portion of an mRNA encoding CD274/PD-L1.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker" The term "siRNA" is also used herein to refer to a dsRNA as described above.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

In one aspect, a modified ribonucleoside includes a deoxyribonucleoside. In such an instance, an iRNA agent can comprise one or more deoxynucleosides, including, for example, a deoxynucleoside overhang(s), or one or more deoxynucleosides within the double stranded portion of a dsRNA. However, it is self evident that under no circumstances is a double stranded DNA molecule encompassed by the term "iRNA."

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, in one embodiment, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety. Examples of "SNALP" formulations are described elsewhere herein.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA can also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781, which are hereby incorporated by reference in their entirety. In vitro introduction into a cell includes methods known in the art such as electroporation and lipofection. Further approaches are described herein below or are known in the art.

As used herein, the term "modulate the expression of," refers to at an least partial "inhibition" or partial "activation" of CD274/PD-L1 gene expression in a cell treated with an iRNA composition as described herein compared to the expression of CD274/PD-L1 in an untreated cell.

The terms "activate," "enhance," "up-regulate the expression of," "increase the expression of," and the like, in so far as they refer to a CD274/PD-L1 gene, herein refer to the at least partial activation of the expression of a CD274/PD-L1 gene, as manifested by an increase in the amount of CD274/PD-L1 mRNA, which may be isolated from or detected in a first cell or group of cells in which a CD274/PD-L1 gene is transcribed and which has or have been treated such that the expression of a CD274/PD-L1 gene is increased, as compared to a second cell or group of cells substantially identical to the first cell or group of cells but which has or have not been so treated (control cells).

In one embodiment, expression of a CD274/PD-L1 gene is activated by at least about 10%, 15%, 20%, 25%, 30%, 35%, 40%, 45%, or 50% by administration of an iRNA as described herein. In some embodiments, a CD274/PD-L1 gene is activated by at least about 60%, 70%, or 80% by administration of an iRNA featured in the invention. In some embodiments, expression of a CD274/PD-L1 gene is activated by at least about 85%, 90%, or 95% or more by administration of an iRNA as described herein. In some embodiments, the CD274/PD-L1 gene expression is increased by at least 1-fold, at least 2-fold, at least 5-fold, at least 10-fold, at least 50-fold, at least 100-fold, at least 500-fold, at least 1000 fold or more in cells treated with an iRNA as described herein compared to the expression in an untreated cell. Activation of expression by small dsRNAs is described, for example, in Li et al., 2006 Proc. Natl. Acad. Sci. U.S.A. 103:17337-42, and in US20070111963 and US2005226848, each of which is incorporated herein by reference.

The terms "silence," "inhibit the expression of," "down-regulate the expression of," "suppress the expression of," and the like, in so far as they refer to a CD274/PD-L1 gene, herein refer to the at least partial suppression of the expression of a CD274/PD-L1 gene, as manifested by a reduction of the amount of CD274/PD-L1 mRNA which may be isolated from or detected in a first cell or group of cells in which a CD274/PD-L1 gene is transcribed and which has or have been treated such that the expression of a CD274/PD-L1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to CD274/PD-L1 gene expression, e.g., the amount of protein encoded by a CD274/PD-L1 gene, or the number of cells displaying a certain phenotype, e.g., lack of or decreased cytokine production. In principle, CD274/PD-L1 gene silencing may be determined in any cell expressing CD274/PD-L1, either constitutively or by genomic engineering, and by any appropriate assay. However, when a reference is needed in order to determine whether a given iRNA inhibits the expression of the CD274/PD-L1 gene by a certain degree and therefore is encompassed by the instant invention, the assays provided in the Examples below shall serve as such reference.

For example, in certain instances, expression of a CD274/PD-L1 gene is suppressed by at least about 10%, 15%, 20%, 25%, 30%, 35%, 40%, 45%, or 50% by administration of an iRNA featured in the invention. In some embodiments, a CD274/PD-L1 gene is suppressed by at least about 60%, 70%, or 80% by administration of an iRNA described herein. In some embodiments, a CD274/PD-L1 gene is suppressed by at least about 85%, 90%, 95%, 98%, 99%, or more by administration of an iRNA as described herein.

As used herein in the context of CD274/PD-L1 expression, the terms "treat," "treatment," and the like, refer to relief from or alleviation of pathological processes mediated by CD274/PD-L1 expression. In the context of the present invention insofar as it relates to any of the other conditions recited herein below (other than pathological processes mediated by CD274/PD-L1 expression), the terms "treat," "treatment," and the like mean to relieve or alleviate at least one symptom associated with such condition, or to slow or reverse the progression or anticipated progression of such condition, such as slowing the progression of a malignancy or cancer, or increasing the clearance of an infectious organism to alleviate/reduce the symptoms caused by the infection, e.g., hepatitis caused by infection with a hepatitis virus.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes mediated by CD274/PD-L1 expression or an overt symptom of pathological processes mediated by CD274/PD-L1 expression. The specific amount that is therapeutically effective can be readily determined by an ordinary medical practitioner, and can vary depending on factors known in the art, such as, for example, the type of pathological processes mediated by CD274/PD-L1 expression, the patient's history and age, the stage of pathological processes mediated by CD274/PD-L1 expression, and the administration of other agents that inhibit pathological processes mediated by CD274/PD-L1 expression.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an iRNA targeting CD274/PD-L1 can reduce CD274/PD-L1 protein levels by at least 10%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

As used herein, a "subject" is a mammal, e.g. a dog, horse, cat, and other non-human primates. In a preferred embodiment, a subject is a human.

As used herein, the term "LNPXX", wherein the "XX" are numerals, is also referred to as "AFXX" herein. For example, LNP09 is also referred to AF09 and LNP12 is also known as or referred to as AF12.

As used herein, the term "comprising" or "comprises" is used in reference to compositions, methods, and respective component(s) thereof, that are essential to the invention, yet open to the inclusion of unspecified elements, whether essential or not.

As used herein, the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

II. Double-Stranded Ribonucleic Acid (dsRNA)

Described herein are iRNA agents that inhibit the expression of the CD274/PD-L1 gene. In one embodiment, the iRNA agent includes double-stranded ribonucleic acid (dsRNA) molecules for inhibiting the expression of a CD274/PD-L1 gene in a cell or mammal, e.g., in a human having a cancer or infectious disease, where the dsRNA includes an antisense strand having a region of complementarity which is complementary to at least a part of an mRNA formed in the expression of a CD274/PD-L1 gene, and where the region of complementarity is 30 nucleotides or less in length, generally 19-24 nucleotides in length, and where the dsRNA, upon contact with a cell expressing the CD274/PD-L1 gene, inhibits the expression of the CD274/PD-L1 gene by at least 10% as assayed by, for example, a PCR or branched DNA (bDNA)-based method, or by a protein-based method, such as by Western blot. In one embodiment, the iRNA agent activates the expression of a CD274/PD-L1 gene in a cell or mammal. Expression of a CD274/PD-L1 gene in cell culture, such as in COS cells, HeLa cells, primary hepatocytes, HepG2 cells, primary cultured cells or in a biological sample from a subject can be assayed by measuring CD274/PD-L1 mRNA levels, such as by bDNA or TaqMan assay, or by measuring protein levels, such as by immunofluorescence analysis, using, for example, Western blotting or flow cytometric techniques.

A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a CD274/PD-L1 gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, an miRNA is a dsRNA. In another embodiment, a dsRNA is not a naturally occurring miRNA. In another embodiment, an iRNA agent useful to target CD274/PD-L1 expression is not generated in the target cell by cleavage of a larger dsRNA.

A dsRNA as described herein can further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, a CD274/PD-L1 gene is a human CD274/PD-L1 gene. In another embodiment the CD274/PD-L1 gene is a mouse or a rat CD274/PD-L1 gene. In specific embodiments, the first sequence is a sense strand of a dsRNA that includes a sense sequence from Table 2 (SEQ ID NO: 5-SEQ ID NO: 436), Table 3 (SEQ ID NO: 437-SEQ ID NO: 868), and Table 5 (SEQ ID NO: 877-SEQ ID NO: 924), and the second sequence is selected from the group consisting of the corresponding antisense sequences of Table 2 (SEQ ID NO: 5-SEQ ID NO: 436), Table 3 (SEQ ID NO: 437-SEQ ID NO: 868), and Table 5 (SEQ ID NO: 877-SEQ ID NO: 924). Alternative dsRNA agents that target elsewhere in the target sequence provided in Table 2, Table 3, and Table 5 can readily be determined using the target sequence and the flanking CD274/PD-L1 sequence.

In one aspect, a dsRNA will include at least nucleotide sequences, whereby the sense strand is selected from the groups of sense sequences provided in Table 2, Table 3, and Table 5, and the corresponding antisense strand of the sense strand selected from Table 2, Table 3, and Table 5. In this aspect, one of the two sequences is complementary to the other of the two sequences, with one of the sequences being substantially complementary to a sequence of an mRNA generated in the expression of a CD274/PD-L1 gene. As such, in this aspect, a dsRNA will include two oligonucleotides, where one oligonucleotide is described as the sense strand in Table 2, Table 3, and Table 5, and the second oligonucleotide is described as the corresponding antisense strand of the sense strand from Table 2, Table 3, and Table 5. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, by virtue of the nature of the oligonucleotide sequences provided in Table 2, Table 3, and Table 5, dsRNAs described herein can include at least one strand of a length of minimally 21 nt. It can be reasonably expected that shorter duplexes having one of the sequences of Table 2, Table 3, and Table 5, minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Table 2, Table 3, and Table 5, and differing in their ability to inhibit the expression of a CD274/PD-L1 gene by not more than 5, 10, 15, 20, 25, or 30% inhibition from a dsRNA comprising the full sequence, are contemplated according to the invention.

In addition, the RNAs provided in Table 2, Table 3, and Table 5 identify a site in a CD274/PD-L1 transcript that is susceptible to RISC-mediated cleavage. As such, the present invention further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides from one of the sequences provided in Table 2, Table 3, and Table 5, coupled to additional nucleotide sequences taken from the region contiguous to the selected sequence in a CD274/PD-L1 gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in Table 2, Table 3, and Table 5 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., i Table 2, Table 3, and Table 5, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a CD274/PD-L1 gene, the RNA strand generally does not contain any mismatch within the central 13 nucleotides. The methods described herein or methods known in the art can be used to determine whether an iRNA containing a mismatch to a target sequence is effective in inhibiting the expression of a CD274/PD-L1 gene. Consideration of the efficacy of iRNAs with mismatches in inhibiting expression of a CD274/PD-L1 gene is important, especially if the particular region of complementarity in a CD274/PD-L1 gene is known to have polymorphic sequence variation within the population.

In one embodiment, at least one end of a dsRNA has a single-stranded nucleotide overhang of 1 to 4, generally 1 or 2 nucleotides. dsRNAs having at least one nucleotide overhang have unexpectedly superior inhibitory properties relative to their blunt-ended counterparts. In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6, 239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O—(2-methoxyethyl) or 2'-MIE) (Martin et al., *Helv. Chim. Acta,* 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamin-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. Chem. Biol. 11, 713-723.). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. Polymers Adv. Technol. 13, 992-999; Kakudo, Chaki, T., S. et al. (2004). Transferrin-Modified Liposomes Equipped with a pH-Sensitive Fusogenic Peptide: An Artificial Viral-like Delivery System. Biochemistry 436, 5618-5628; Yessine, M. A. and Leroux, J. C. (2004). Membrane-destabilizing polyanions: interaction with lipid bilayers and endosomal escape of biomacromolecules. Adv. Drug Deliv. Rev. 56, 999-1021; Oliveira, S., van Rooy, I. et al. (2007). Fusogenic peptides enhance endosomal escape improving iRNA-induced silencing of oncogenes. Int. J. Pharm. 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs is described in Biochim. Biophys. Acta 1559, 56-68).

In certain embodiments, the endosomolytic components of the present invention can be polyanionic peptides or peptidomimetics which show pH-dependent membrane activity and/or fusogenicity. A peptidomimetic can be a small protein-like chain designed to mimic a peptide. A peptidomimetic can arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Libraries of compounds can be screened for their differential membrane activity at endosomal pH versus neutral pH using a hemolysis assay. Promising candidates isolated by this method may be used as components of the modular compositions of the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GAL4 peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component can contain a chemical group (e.g., an amino acid) which will undergo a change in charge or protonation in response to a change in pH. The endosomolytic component may be linear or branched. Exemplary primary sequences of endosomolytic components include ***H2N-(AALEALAEALEALAEALEALAE-AAAAGGC)-CO2H (SEQ ID NO: 873); H2N-(AALAE-ALAEALAEALAEALAAAAGGC)-CO2H (SEQ ID NO: 874); and H2N-(ALEALAEALEALAEA)-CONH2 (SEQ ID NO: 875).

In certain embodiments, more than one endosomolytic component can be incorporated into the iRNA agent of the invention. In some embodiments, this will entail incorporating more than one of the same endosomolytic component into the iRNA agent. In other embodiments, this will entail incorporating two or more different endosomolytic components into iRNA agent.

These endosomolytic components can mediate endosomal escape by, for example, changing conformation at endosomal pH. In certain embodiments, the endosomolytic components can exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4). "Fusogenic activity," as used herein, is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

In addition to hemolysis assays, as described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an iRNA agent described herein is constructed using one or more test or putative fusogenic agents. The iRNA agent can be labeled for easy visualization. The ability of the endosomolytic component to promote endosomal escape, once the iRNA agent is taken up by the cell, can be evaluated, e.g., by preparation of an endosome preparation, or by microscopy techniques, which enable visualization of the labeled iRNA agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition.

A two-step assay can also be performed, wherein a first assay evaluates the ability of a test compound alone to respond to changes in pH, and a second assay evaluates the ability of a modular composition that includes the test compound to respond to changes in pH.

Lipid Conjugates

In one embodiment of the aspects described herein, a ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Cell Permeation Peptides

Peptides suitable for use with the present invention can be a natural peptide, e.g., tat or antennopedia peptide, a synthetic peptide, or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:1). An RFGF analogue (e.g., amino acid sequence AALLPVLLAAP (SEQ ID NO:2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:3)) and the *Drosophila Antennapedia* protein (RQIKIWFQNRRMKWKK (SEQ ID NO: 4)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an dsRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver a iRNA agent to a tumor cell expressing $\alpha_v\beta_3$ (Haubner et al., Jour. Nucl. Med., 42:326-336, 2001).

Peptides that target markers enriched in proliferating cells can be used, e.g., RGD containing peptides and peptidomimetics can target cancer cells, in particular cells that exhibit an $\alpha v\beta 3$ integrin. Thus, one could use RGD peptides, cyclic peptides containing RGD, RGD peptides that include D-amino acids, as well as synthetic RGD mimics. In addition to RGD, one can use other moieties that target the $\alpha v\beta 3$ integrin ligand. Generally, such ligands can be used to control proliferating cells and angiogenesis.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Carbohydrate Conjugates

In some embodiments, the iRNA oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

In one embodiment, the carbohydrate conjugate is selected from the group consisting of:

Formula II
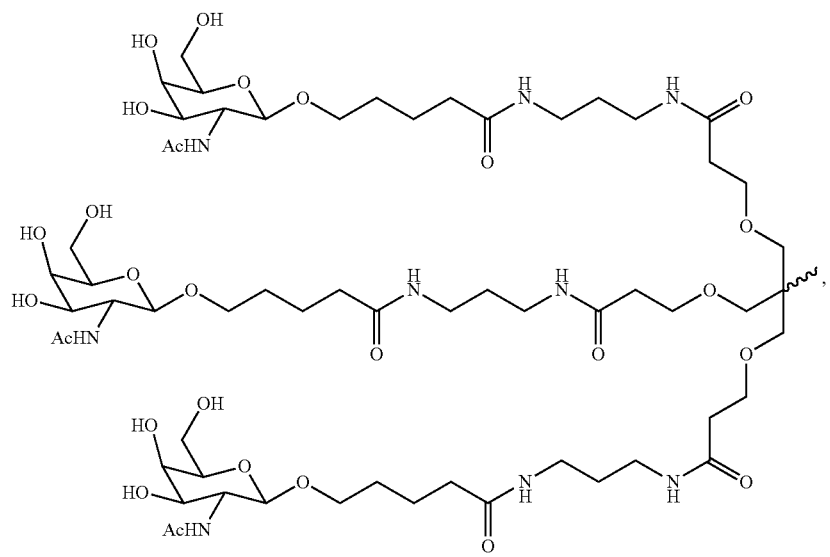
Formula III
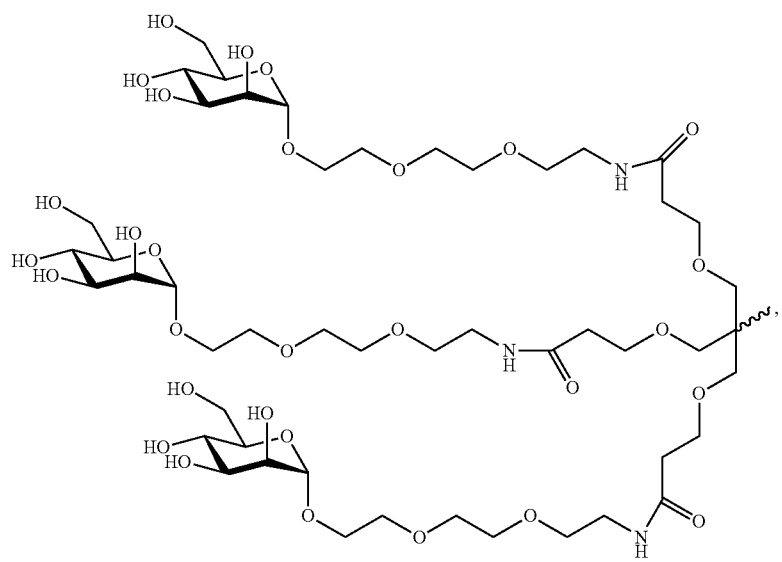
Formula IV
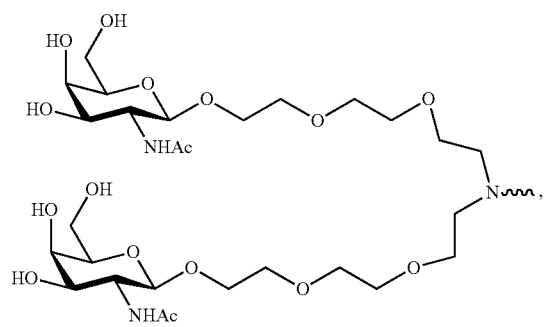
Formula V
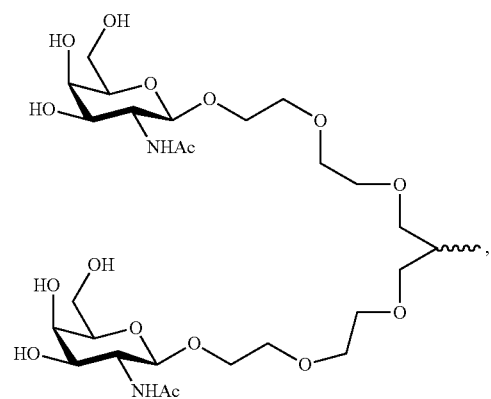

-continued
Formula VI
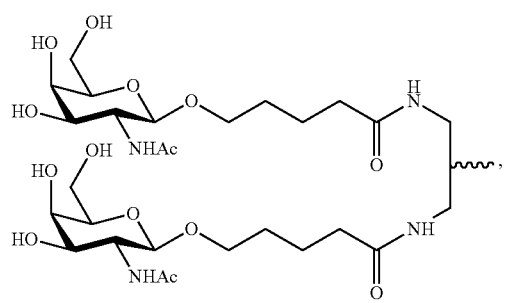
Formula VII
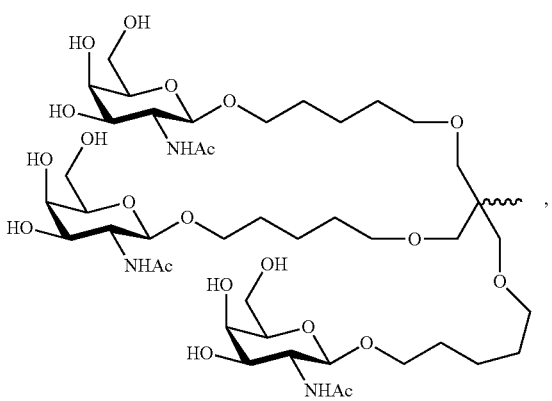
Formula VIII
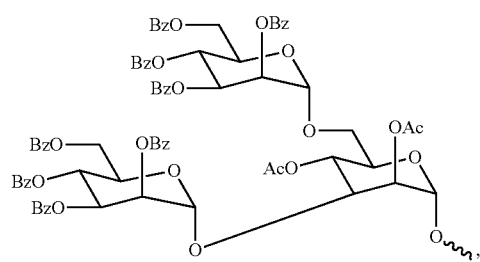
Formula IX
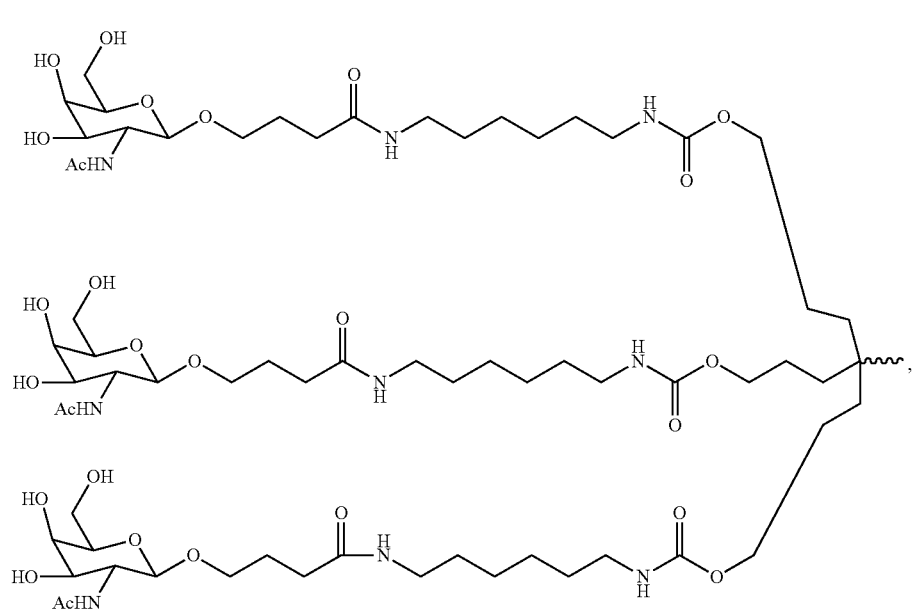

Formula X
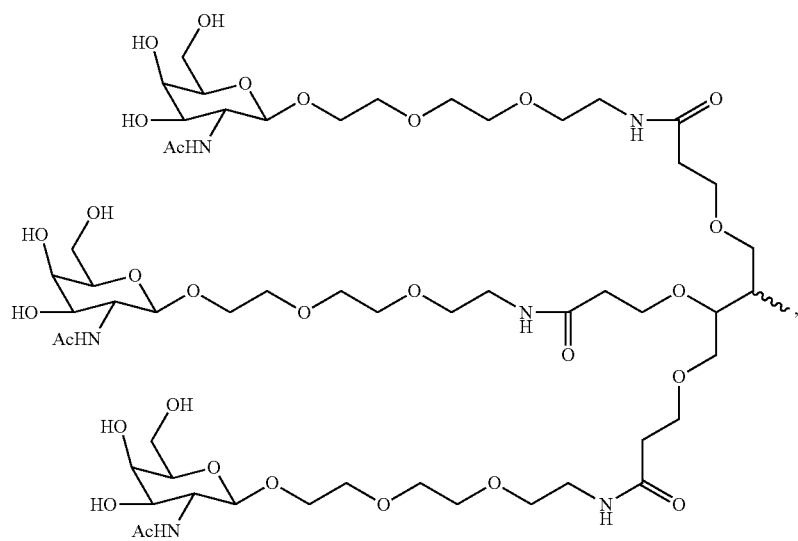
Formula XI
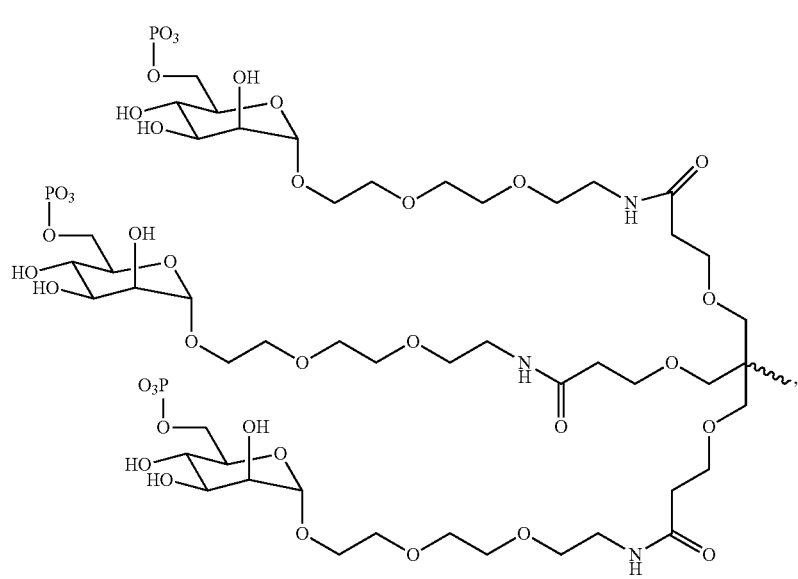

-continued
Formula XII
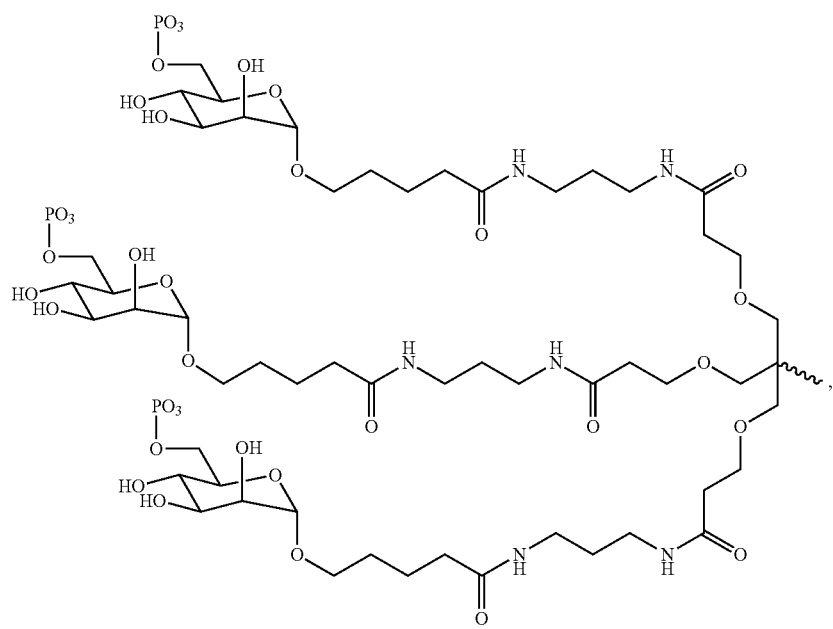
Formula XIII
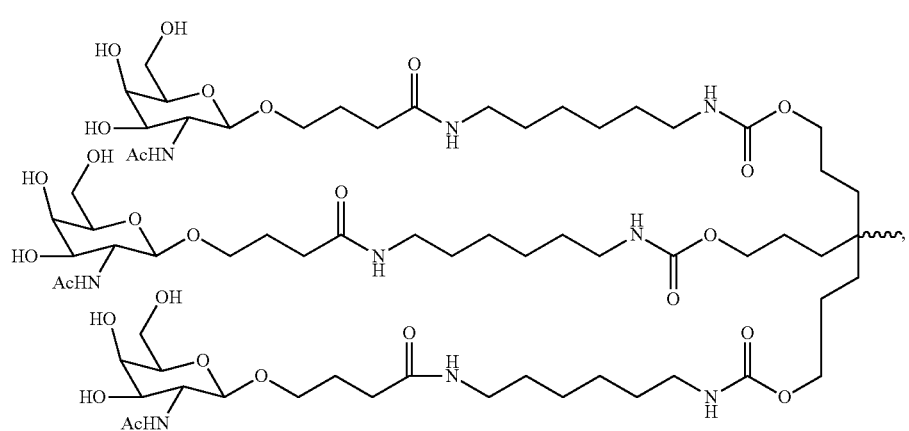
Formula XIV
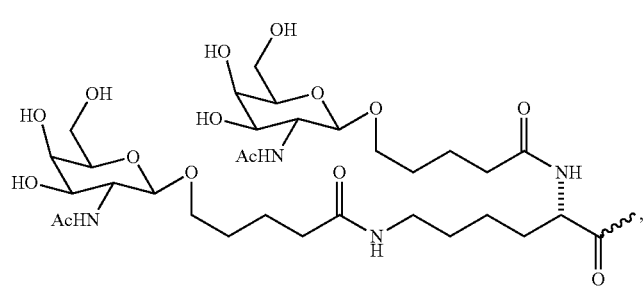
Formula XV
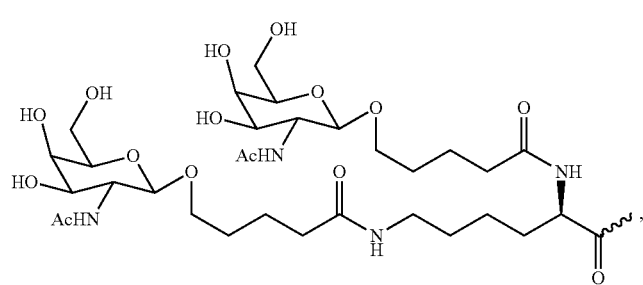

-continued
Formula XVI
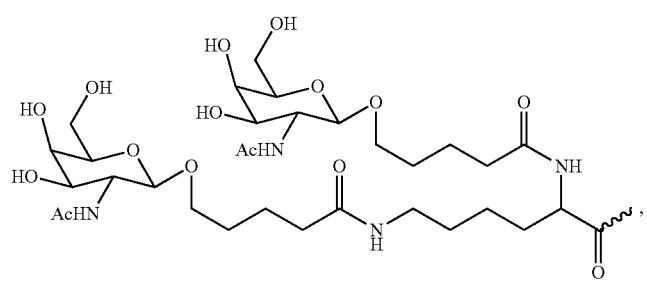
Formula XVII
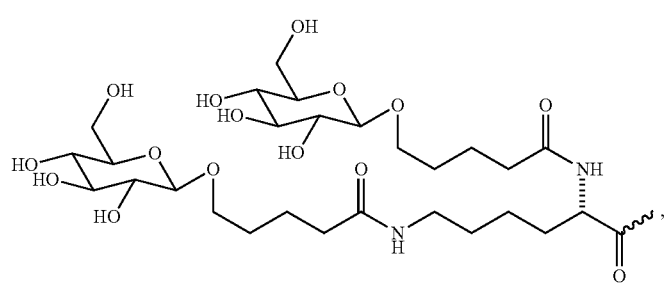
Formula XVIII
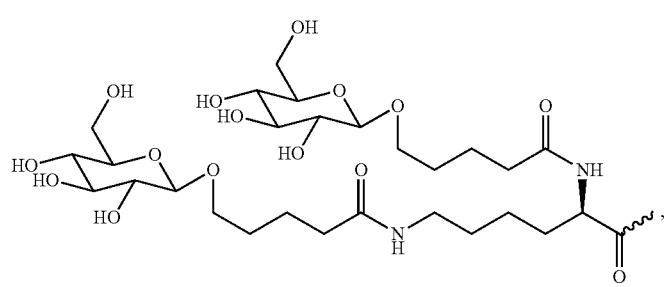
Formula XIX
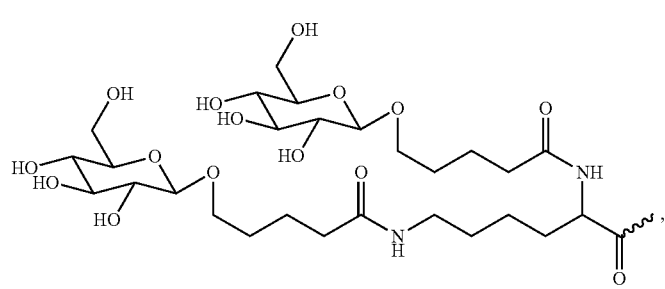
Formula XX
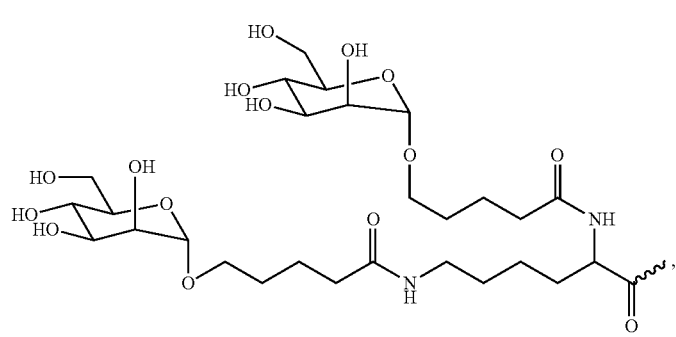

Formula XXI
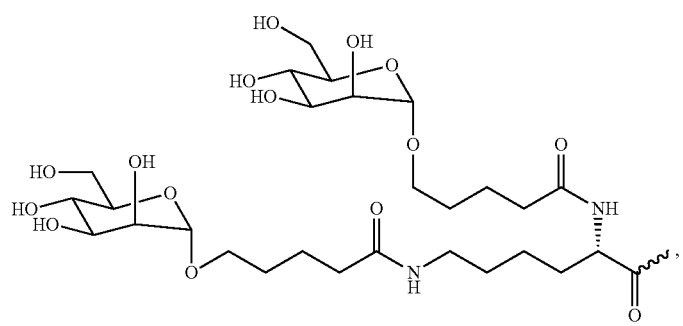
Formula XXII
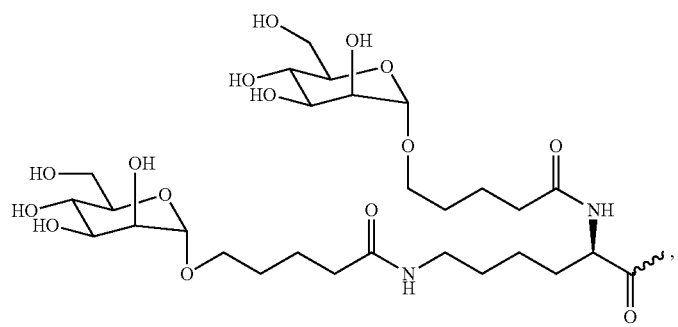
i.e., Formula II-Formula XXII.
Another representative carbohydrate conjugate for use in the embodiments described herein includes, but is not limited to,
(Formula XXIII)
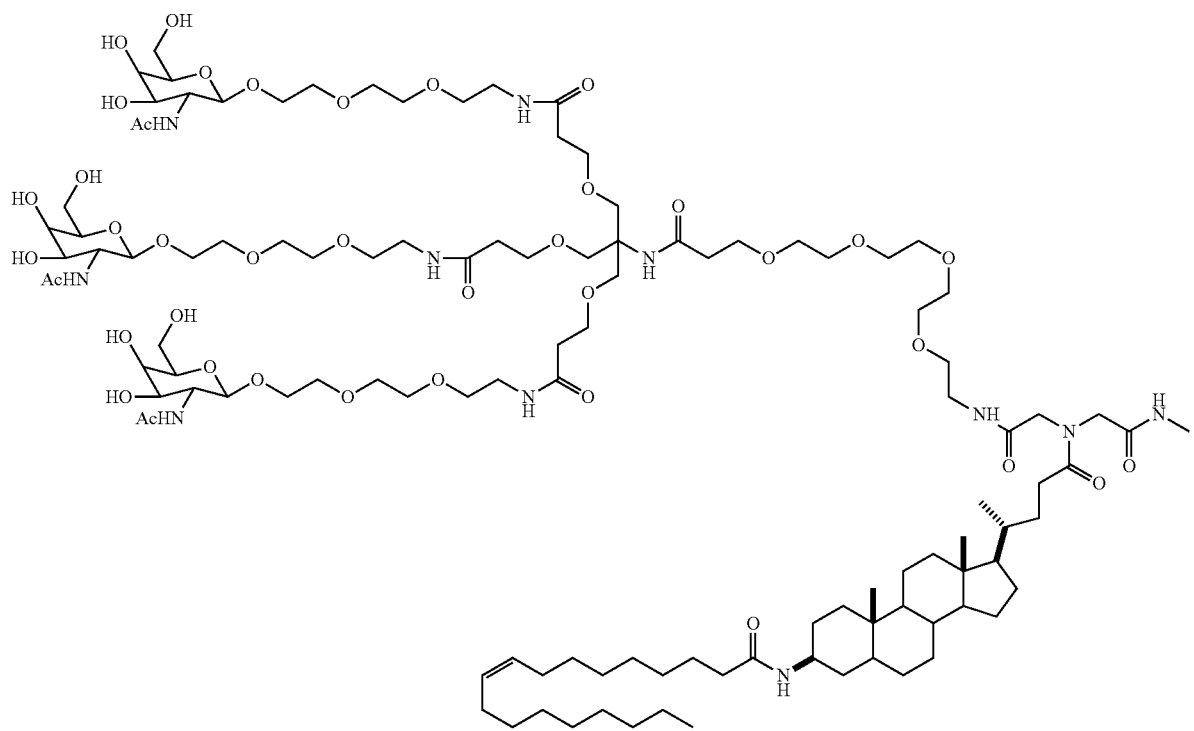

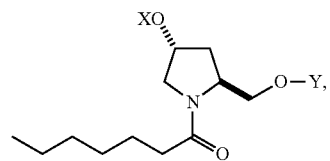

when one of X or Y is an oligonucleotide, the other is a hydrogen.

In some embodiments, the carbohydrate conjugate further comprises other ligand such as, but not limited to, PK modulator, endosomolytic ligand, and cell permeation peptide.

Linkers

In some embodiments, the conjugates described herein can be attached to the iRNA oligonucleotide with various linkers that can be cleavable or non cleavable.

The term "linker" or "linking group" means an organic moiety that connects two parts of a compound. Linkers typically comprise a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation.

An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=N,N—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula -NHCHR$^A$C(O)NH-CHR$^B$C(O), where R$^A$ and R$^B$ are the R groups of the two adjacent amino acids. These candidates can be evaluated using methods analogous to those described above.

Representative carbohydrate conjugates with linkers include, but are not limited to, (Formula XXIV)

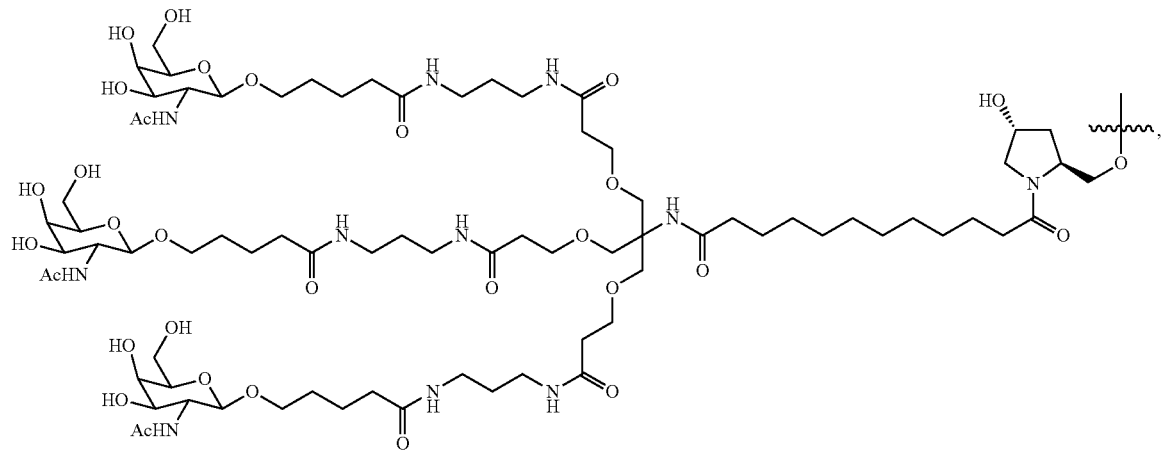

-continued
(Formula XXV)
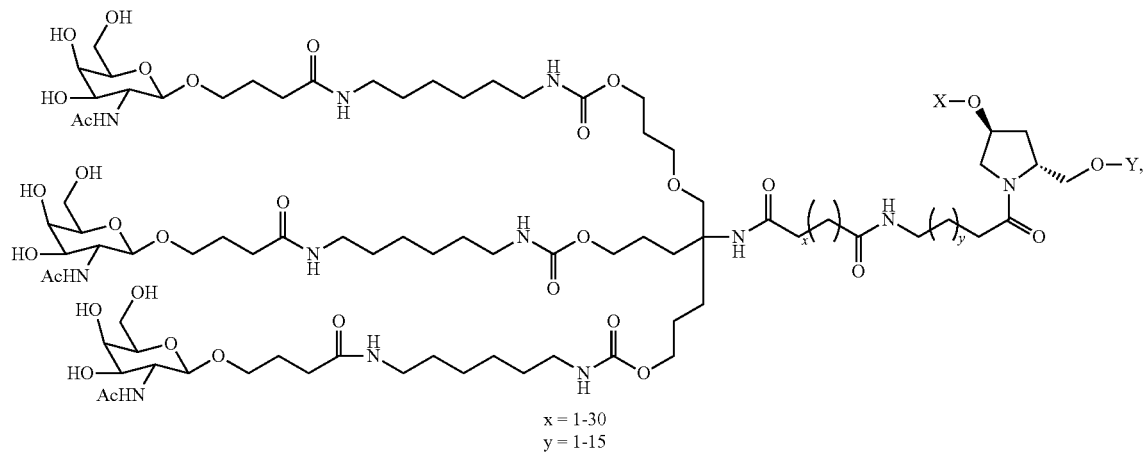
x = 1-30
y = 1-15
(Formula XXVI)
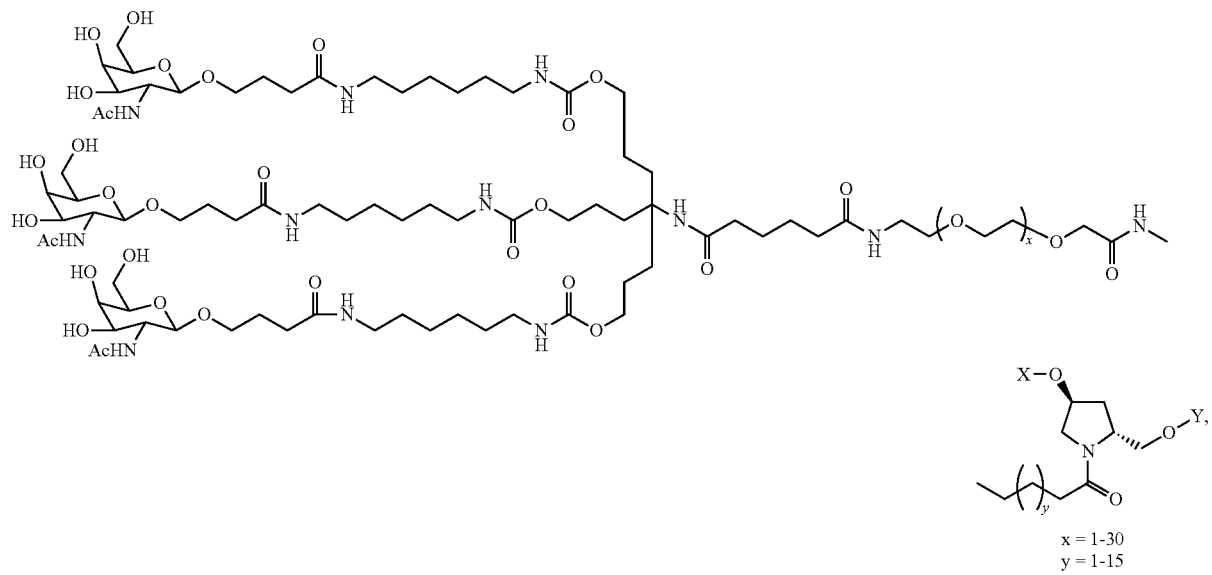
x = 1-30
y = 1-15
(Formula XXVII)
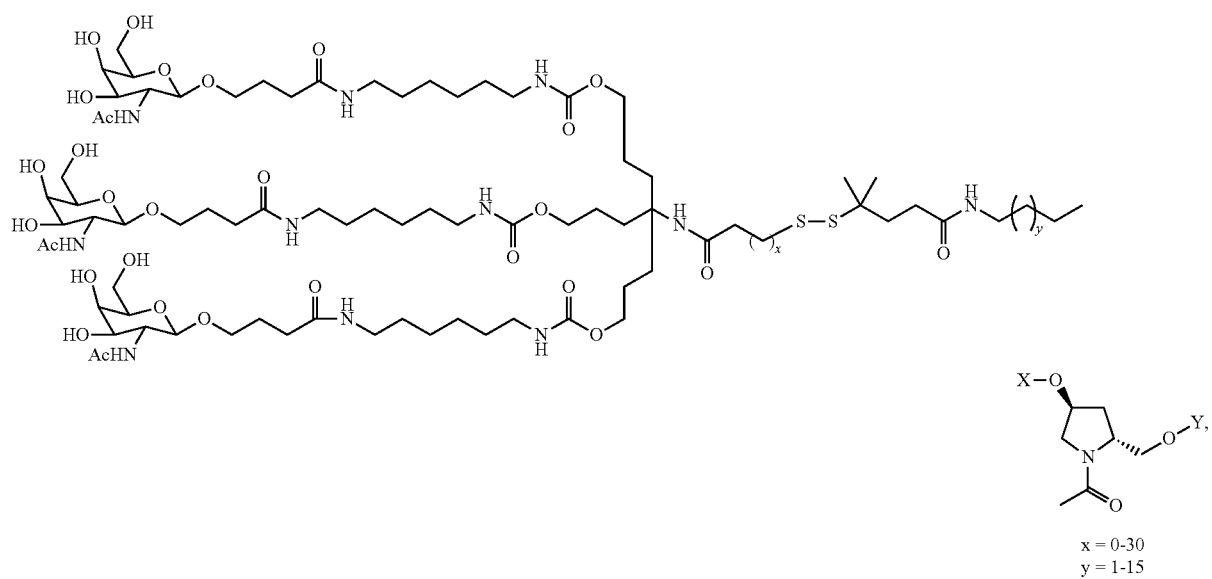
x = 0-30
y = 1-15

-continued
(Formula XXVIII)
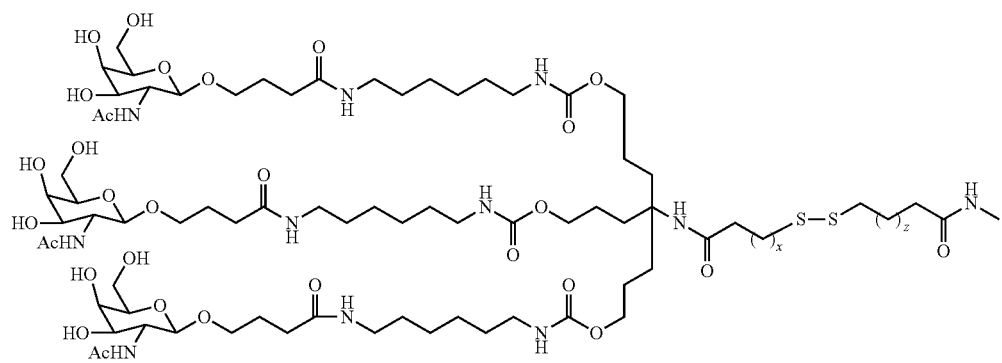
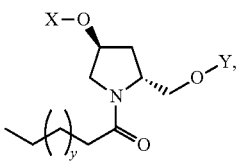
x = 0-30
y = 1-15
z = 1-20
(Formula XXIX)
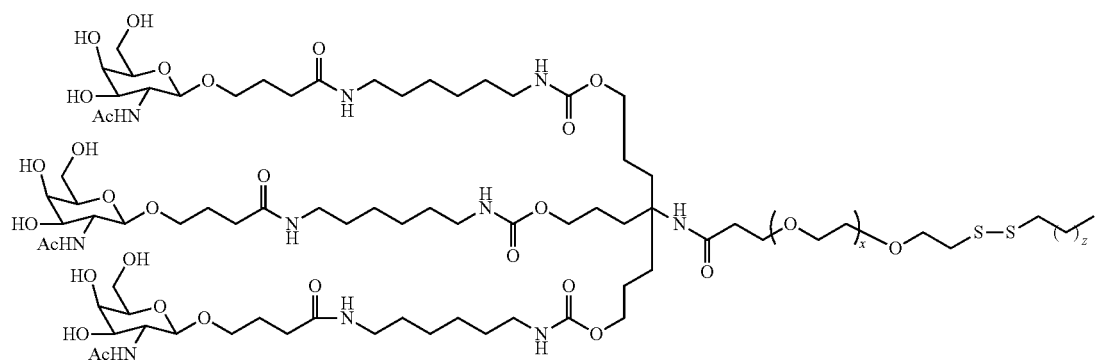
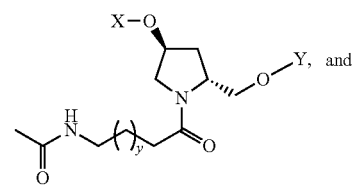 and
x = 1-30
y = 1-15
z = 1-20
(Formula XXX)
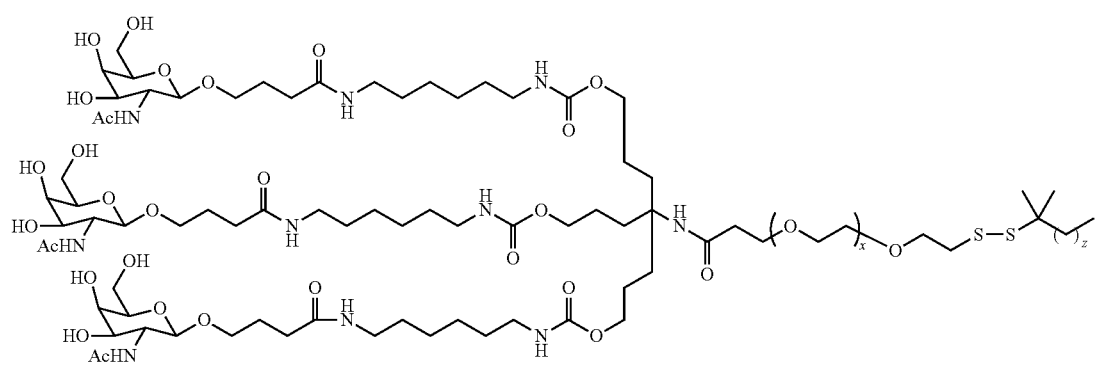

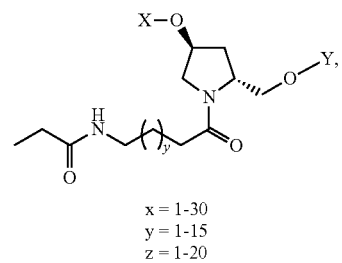

x = 1-30
y = 1-15
z = 1-20 when one of X or Y is an oligonucleotide, the other is a hydrogen.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds. "Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero- 3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamin-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an amino linker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

Delivery of iRNA

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA.

Delivery of an iRNA Composition

In general, any method of delivering a nucleic acid molecule can be adapted for use with an iRNA (see e.g., Akhtar S, and Julian R L. (1992) Trends Cell. Biol. 2(5):139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; L1, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129: 521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol. 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded dsRNAs

In another aspect, iRNA targeting the CD274/PD-L1 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmaceutical Compositions Containing iRNA

In one embodiment, provided herein are pharmaceutical compositions containing an iRNA and a pharmaceutically acceptable carrier. The pharmaceutical composition containing the iRNA is useful for treating a disease or disorder associated with the expression or activity of a CD274/PD-L1 gene, such as pathological processes mediated by CD274/PD-L1 expression. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions featured herein are administered in dosages sufficient to inhibit expression of CD274/PD-L1 genes. In general, a suitable dose of iRNA will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the iRNA may be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on CD274/PD-L1 levels can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by CD274/PD-L1 expression. Such models can be used for in vivo testing of iRNA, as well as for determining a therapeutically effective dose. A suitable mouse model is, for example, a mouse containing a transgene expressing human CD274/PD-L1.

The present invention also includes pharmaceutical compositions and formulations that include the iRNA compounds featured in the invention. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al.

(U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a CD274/PD-L1 dsRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid can be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3- morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application Ser. No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidyletanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4HCl (MW 1487) (see U.S. patent application Ser. No. 12/056,230, filed Mar. 26, 2008, which is herein incorporated by reference in its entirety), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula I

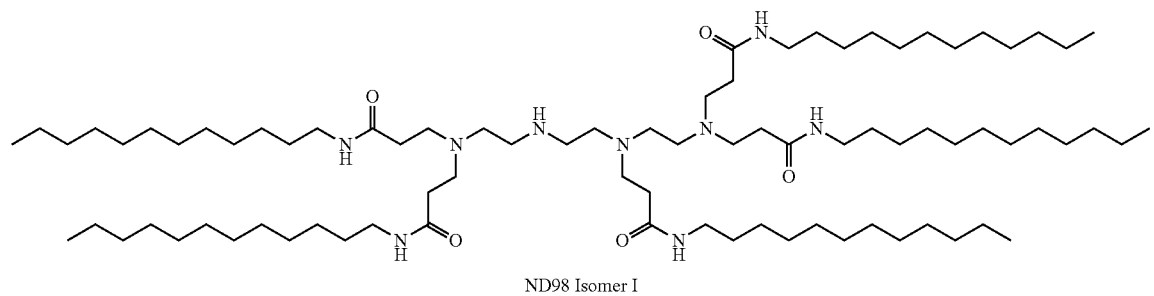

ND98 Isomer I

LNP01 formulations are described, e.g., in International Application Publication No. WO 2008/042973, which is hereby incorporated by reference.

Additional exemplary lipid-dsRNA formulations are as follows:

| | Cationic Lipid | cationic lipid/non-cationic lipid/cholesterol/PEG-lipid conjugate Lipid:siRNA ratio |
|---|---|---|
| SNALP | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| S-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200) | C12-200/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/239,686, filed Sep. 3, 2009, which is hereby incorporated by reference.

MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US2010/28224, filed Jun. 10, 2010 which are hereby incorporated by reference in their entireties.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009, and International Application No. PCT/US2010/33777, filed May 5, 2010, which are hereby incorporated by reference in their entireties.

Synthesis of Cationic Lipids.

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, $OR^x$, —$NR^xR^y$, —$NR^xC(═O)R^y$, —$NR^xSO_2R^y$, —C(═O)$R^x$, —C(═O)$OR^x$, —C(═O)$NR^xR^y$, —$SO_nR^x$ and —$SO_nNR^xR^y$, wherein n is 0, 1 or 2, $R^x$ and $R^y$ are the same or different and independently hydrogen, alkyl or heterocycle, and each of said alkyl and heterocycle substituents may be further substituted with one or more of oxo, halogen, —OH, —CN, alkyl, —$OR^x$, heterocycle, —$NR^xR^y$, —$NR^xC(═O)R^y$, —$NR^xSO_2R^y$, —C(═O)$R^x$, —C(═O)$OR^x$, —C(═O)$NR^xR^y$, —$SO_nR^x$ and —$SO_nNR^xR^y$.

"Halogen" means fluoro, chloro, bromo and iodo.

In some embodiments, the methods of the invention can require the use of protecting groups. Protecting group methodology is well known to those skilled in the art (see, for example, PROTECTIVE GROUPS IN ORGANIC SYNTHESIS, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

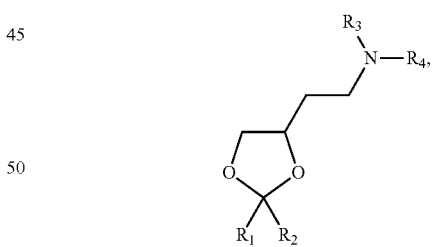

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

Scheme 1

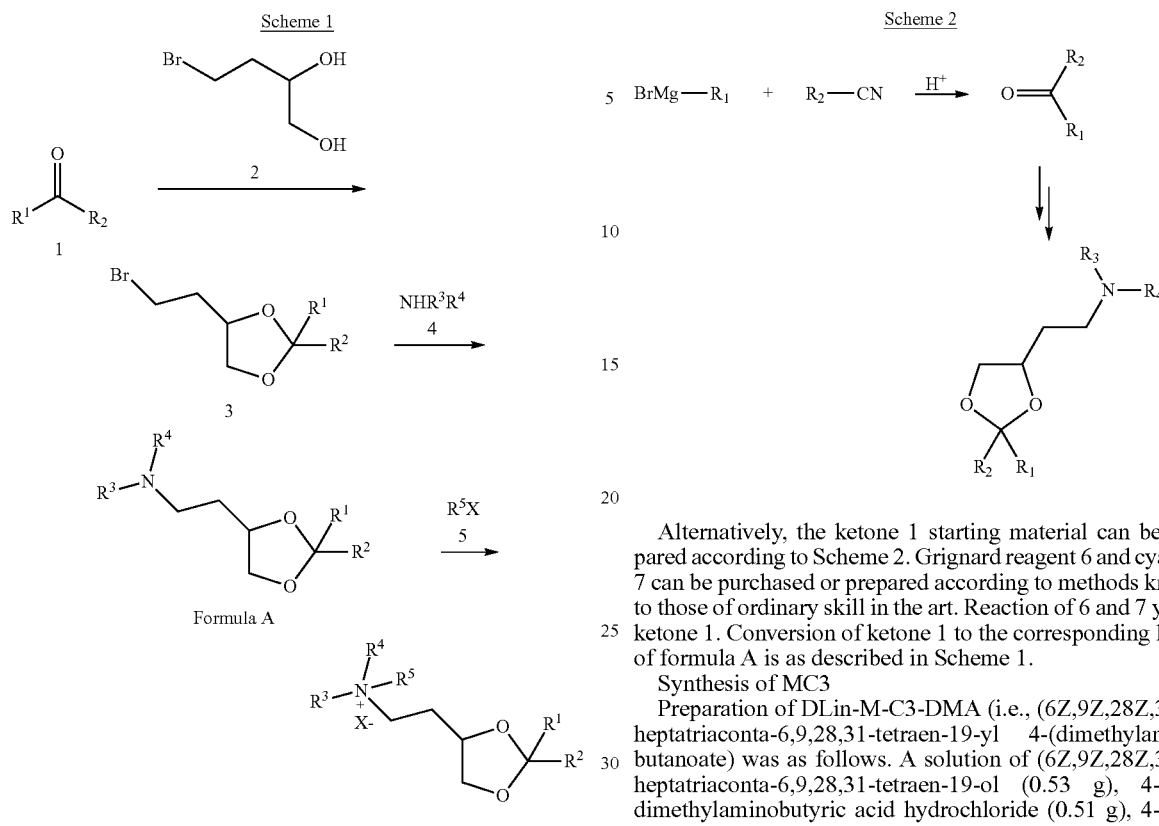

Lipid A, where $R_1$ and $R_2$ are independently alkyl, alkenyl or alkynyl, each can be optionally substituted, and $R_3$ and $R_4$ are independently lower alkyl or $R_3$ and $R_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

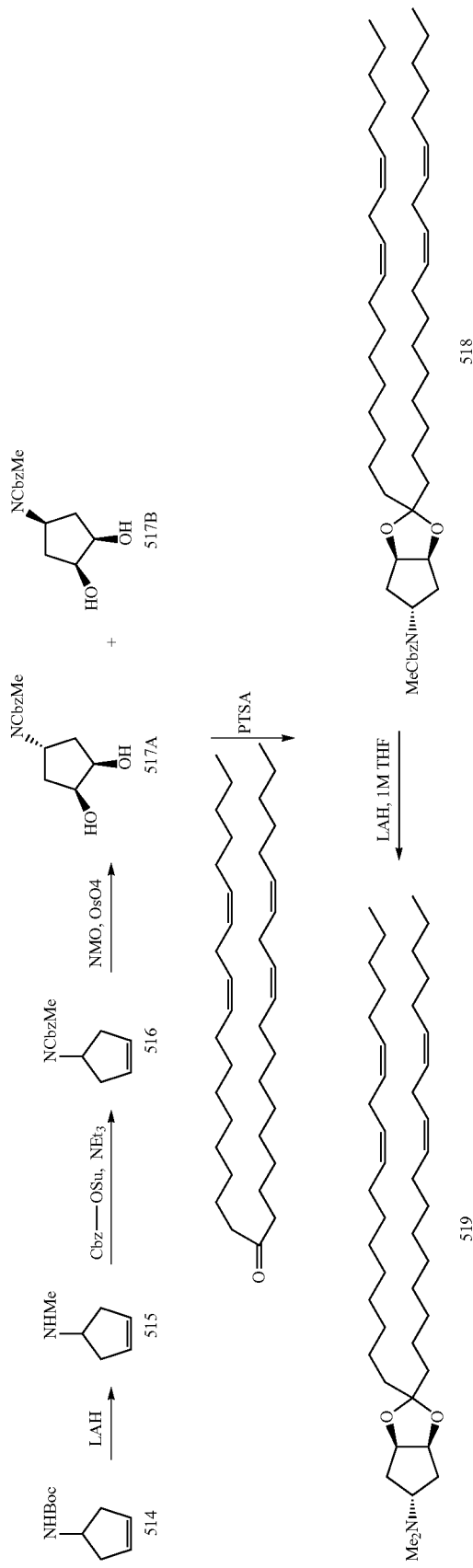

Synthesis of 515:

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): $\delta$=9.34 (broad, 2H), 5.68 (s, 2H), 3.74 (m, 1H), 2.66-2.60 (m, 2H), 2.50-2.45 (m, 5H).

Synthesis of 516:

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl$_3$, 400 MHz): $\delta$=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B:

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an Na2SO4 and solvent was removed in vacuum. Silica gel column chromatographic purification of the crude material was afforded a mixture of diastereomers, which were separated by prep HPLC. Yield: —6g crude 517A-Peak-1 (white solid), 5.13 g (96%). 1H-NMR (DMSO, 400 MHz): $\delta$=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]—266.3, [M+NH4+]-283.5 present, HPLC-97.86%. Stereochemistry confirmed by X-ray.

Synthesis of 518:

Using a procedure analogous to that described for the synthesis of compound 505, compound 518 (1.2 g, 41%) was obtained as a colorless oil. 1H-NMR (CDCl$_3$, 400 MHz): $\delta$=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519:

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR $\square$=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6. Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium taur-24,25-dihydr-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Additional Formulations
Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel HC., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of iRNAs and nucleic acids are formulated as microemulsions. A microemulsion may be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention may also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly iRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono-and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydr-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000® (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invivogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano- stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention can additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances that increase the viscosity of the suspension including, for example, sodium carboxymethylcellulose, sorbitol and/or dextran. The suspension may also contain stabilizers.

In some embodiments, pharmaceutical compositions featured in the invention include (a) one or more iRNA compounds and (b) one or more biologic agents which function by a non-RNAi mechanism. Examples of such biologics include, biologics that target one or more of PD-1, PD-L1, or B7-H1 (CD80) (e.g., monoclonal antibodies against PD-1, PD-L1, or B7-H1), or one or more recombinant cytokines (e.g., IL6, IFN-γ, and TNF).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the iRNAs described herein can be administered in combination with other known agents effective in treatment of pathological processes mediated by CD274/PD-L1 expression. In any event, the administering physician can adjust the amount and timing of iRNA administration on the basis of results observed using standard measures of efficacy known in the art or described herein.

Methods for Treating Diseases Caused by Expression of a CD274/PD-L1 Gene

The invention relates in particular to the use of an iRNA targeting CD274/PD-L1 and compositions containing at least one such iRNA for the treatment of a CD274/PD-L1-mediated disorder or disease. For example, a composition containing an iRNA targeting a CD274/PD-L1 gene is used for treatment of a cancer. As used herein, cancer refers to any of various malignant neoplasms characterized by the proliferation of anaplastic cells that tend to invade surrounding tissue and metastasize to new body sites and also refers to the pathological condition characterized by such malignant neoplastic growths. A cancer can be a tumor or hematological malignancy, and includes but is not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

Leukemias, or cancers of the blood or bone marrow that are characterized by an abnormal proliferation of white blood cells i.e., leukocytes, can be divided into four major classifications including Acute lymphoblastic leukemia (ALL), Chronic lymphocytic leukemia (CLL), Acute myelogenous leukemia or acute myeloid leukemia (AML) (AML with translocations between chromosome 10 and 11 [t(10, 11)], chromosome 8 and 21 [t(8;21)], chromosome 15 and 17 [t(15; 17)], and inversions in chromosome 16 [inv(16)]; AML with multilineage dysplasia, which includes patients who have had a prior myelodysplastic syndrome (MDS) or myeloproliferative disease that transforms into AML; AML and myelodysplastic syndrome (MDS), therapy-related, which category includes patients who have had prior chemotherapy and/or radiation and subsequently develop AML or MDS; d) AML not otherwise categorized, which includes subtypes of AML that do not fall into the above categories; and e) Acute leukemias of ambiguous lineage, which occur when the leukemic cells can not be classified as either myeloid or lymphoid cells, or where both types of cells are present); and Chronic myelogenous leukemia (CML).

The types of carcinomas include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

The types of sarcomas include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

The invention further relates to the use of an iRNA or a pharmaceutical composition thereof, e.g., for treating a cancer, in combination with other pharmaceuticals and/or other therapeutic methods, e.g., with known pharmaceuticals and/or known therapeutic methods, such as, for example, those which are currently employed for treating these disorders. For example, the iRNA or pharmaceutical composition thereof can also be administered in conjunction with one or more additional anti-cancer treatments, such as biological, chemotherapy and radiotherapy. Accordingly, a treatment can include, for example, imatinib (Gleevac), all-trans-retinoic acid, a monoclonal antibody treatment (gemtuzumab, ozogamicin), chemotherapy (for example, chlorambucil, prednisone, prednisolone, vincristine, cytarabine, clofarabine, farnesyl transferase inhibitors, decitabine, inhibitors of MDR1), rituximab, interferon-α, anthracycline drugs (such as daunorubicin or idarubicin), L-asparaginase, doxorubicin, cyclophosphamide, doxorubicin, bleomycin, fludarabine, etoposide, pentostatin, or cladribine), bone marrow transplant, stem cell transplant, radiation therapy, anti-metabolite drugs (methotrexate and 6-mercaptopurine), or any combination thereof.

Radiation therapy (also called radiotherapy, X-ray therapy, or irradiation) is the use of ionizing radiation to kill cancer cells and shrink tumors. Radiation therapy can be administered externally via external beam radiotherapy (EBRT) or internally via brachytherapy. The effects of radiation therapy are localised and confined to the region being treated. Radiation therapy may be used to treat almost every type of solid tumor, including cancers of the brain, breast, cervix, larynx, lung, pancreas, prostate, skin, stomach, uterus, or soft tissue sarcomas. Radiation is also used to treat leukemia and lymphoma.

Chemotherapy is the treatment of cancer with drugs that can destroy cancer cells. In current usage, the term "chemotherapy" usually refers to cytotoxic drugs which affect rapidly dividing cells in general, in contrast with targeted therapy. Chemotherapy drugs interfere with cell division in various possible ways, e.g. with the duplication of DNA or the separation of newly formed chromosomes. Most forms of chemotherapy target all rapidly dividing cells and are not specific to cancer cells, although some degree of specificity may come from the inability of many cancer cells to repair DNA damage, while normal cells generally can. Most chemotherapy regimens are given in combination. Exemplary chemotherapeutic agents include, but are not limited to, 5-FU Enhancer, 9-AC, AG2037, AG3340, Aggrecanase Inhibitor, Aminoglutethimide, Amsacrine (m-AMSA), Asparaginase, Azacitidine, Batimastat (BB94), BAY 12-9566, BCH-4556, Bis-Naphtalimide, Busulfan, Capecitabine, Carboplatin, Carmustaine+Polifepr Osan, cdk4/cdk2 inhibitors, Chlorombucil, CI-994, Cisplatin, Cladribine, CS-682, Cytarabine HCl, D2163, Dactinomycin, Daunorubicin HCl, DepoCyt, Dexifosamide, Docetaxel, Dolastain, Doxifluridine, Doxorubicin, DX8951f, E 7070, EGFR, Epirubicin, Erythropoietin, Estramustine phosphate sodium, Etoposide (VP16-213), Farnesyl Transferase Inhibitor, FK 317, Flavopiridol, Floxuridine, Fludarabine, Fluorouracil (5-FU), Flutamide, Fragyline, Gemcitabine, Hexamethylmelamine (HMM), Hydroxyurea (hydroxycarbamide), Ifosfamide, Interferon Alfa-2a, Interferon Alfa-2b, Interleukin-2, Irinotecan, ISI 641, Krestin, Lemonal DP 2202, Leuprolide acetate (LHRH-releasing factor analogue), Levamisole, LiGLA (lithium-gamma linolenate), Lodine Seeds, Lometexol, Lomustine (CCNU), Marimistat, Mechlorethamine HCl (nitrogen mustard), Megestrol acetate, Meglamine GLA, Mercaptopurine, Mesna, Mitoguazone (methyl-GAG; methyl glyoxal bis-guanylhydrazone; MGBG), Mitotane (o.p'-DDD), Mitoxantrone, Mitoxantrone HCl, MMI 270, MMP, MTA/LY 231514, Octreotide, ODN 698, OK-432, Oral Platinum, Oral Taxoid, Paclitaxel (TAXOL®), PARP Inhibitors, PD 183805, Pentostatin (2' deoxycoformycin), PKC 412, Plicamycin, Procarbazine HCl, PSC 833, Ralitrexed, RAS Farnesyl Transferase Inhibitor, RAS Oncogene Inhibitor, Semustine (methyl-CCNU), Streptozocin, Suramin, Tamoxifen citrate, Taxane Analog, Temozolomide, Teniposide (VM-26), Thioguanine, Thiotepa, Topotecan, Tyrosine Kinase, UFT (Tegafur/Uracil), Valrubicin, Vinblastine sulfate, Vindesine sulfate, VX-710, VX-853, YM 116, ZD 0101, ZD 0473/Anormed, ZD 1839, ZD 9331.

Biological therapies use the body's immune system, either directly or indirectly, to fight cancer or to lessen the side effects that may be caused by some cancer treatments. In one sense, targeting CD274/PD-L1 can be considered in this group of therapies in that it can stimulate immune system action against a tumor, for example. However, this approach can also be considered with other such biological approaches, e.g., immune response modifying therapies such as the administration of interferons, interleukins, colony-stimulating factors, monoclonal antibodies, vaccines, gene therapy, and nonspecific immunomodulating agents are also envisioned as anti-cancer therapies to be combined with the inhibition of CD274/PD-L1. Small molecule targeted therapy drugs are generally inhibitors of enzymatic domains on mutated, overexpressed, or otherwise critical proteins within the cancer cell, such as tyrosine kinase inhibitors imatinib (Gleevec/Glivec) and gefitinib (Iressa). Examples of monoclonal antibody therapies that can be used with an iRNA or pharmaceutical composition thereof include, but are not limited to, the anti-HER2/neu antibody trastuzumab (Herceptin) used in breast cancer, and the anti-CD20 antibody rituximab, used in a variety of B-cell malignancies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

Cancer immunotherapy refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, and the use of Sipuleucel-T for prostate cancer, in which dendritic cells from the patient are loaded with prostatic acid phosphatase peptides to induce a specific immune response against prostate-derived cells.

In some embodiments, an iRNA targeting CD274/PD-L1 is administered in combination with an angiogenesis inhibitor. In some embodiments, the angiogenesis inhibitors for use in the methods described herein include, but are not limited to, monoclonal antibody therapies directed against specific pro-angiogenic growth factors and/or their receptors. Examples of these are: bevacizumab (Avastin®), cetuximab (Erbitux®), panitumumab (Vectibix™), and trastuzumab (Herceptin®). In some embodiments, the angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (Tarceva®), sorafenib (Nexavar®), and sunitinib (Sutent®). In some embodiments, the angiogenesis inhibitors for use in the methods described herein include but are not limited to inhibitors of mTOR (mammalian target of rapamycin) such as temsirolimus (Toricel™), bortezomib (Velcade®), thalidomide (Thalomid®), and Doxycyclin, In other embodiments, the angiogenesis inhibitors for use in the methods described herein include one or more drugs that target the VEGF pathway, including, but not limited to, Bevacizumab (Avastin®), sunitinib (Sutent®), and sorafenib (Nexavar®). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (AEterna Zentaris Inc; Quebec City, Calif.), ZM323881 (CalBiochem. CA, USA), pegaptanib (Macugen) (Eyetech Pharmaceuticals), an anti-VEGF aptamer and combinations thereof.

In other embodiments, the angiogenesis inhibitors for use in the methods described herein include anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C—X—C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronectin (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16kD fragment, proliferin-related protein (PRP), retinoids, tetrahydrocortisol-S transforming growth factor-beta (TGF-b), vasculostatin, and vasostatin (calreticulin fragment).pamidronate thalidomide, TNP470, the bisphosphonate family such as amino-bisphosphonate zoledronic acid, bombesin/gastrin-releasing peptide (GRP) antagonists such as RC-3095 and RC-3940-II (Bajol AM, et. al., British Journal of Cancer (2004) 90, 245-252), anti-VEGF peptide RRKRRR (Drk6) (SEQ ID NO: 925) (Seung-Ah Yoo, J.Immuno, 2005, 174: 5846-5855).

Efficacy of treatment, prevention, or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of an iRNA targeting CD274/PD-L1 or pharmaceutical composition thereof, "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

The invention relates in particular to the use of an iRNA targeting CD274/PD-L1 and compositions containing at least one such iRNA for the treatment of a CD274/PD-L1-mediated disorder or disease. For example, a composition containing an iRNA targeting a CD274/PD-L1 gene is used for treatment of an infectious disease or disorder, for example, in a subject having an infection. In some preferred embodiments the subject has an infection or is at risk of having an infection. An "infection" as used herein refers to a disease or condition attributable to the presence in a host of a foreign organism or agent that reproduces within the host. Infections typically involve breach of a normal mucosal or other tissue barrier by an infectious organism or agent. A subject that has an infection is a subject having objectively measurable infectious organisms or agents present in the subject's body. A subject at risk of having an infection is a subject that is predisposed to develop an infection. Such a subject can include, for example, a subject with a known or suspected exposure to an infectious organism or agent. A subject at risk of having an infection also can include a subject with a condition associated with impaired ability to mount an immune response to an infectious organism or agent, e.g., a subject with a congenital or acquired immunodeficiency, a subject undergoing radiation therapy or chemotherapy, a subject with a burn injury, a subject with a traumatic injury, a subject undergoing surgery or other invasive medical or dental procedure.

Infections are broadly classified as bacterial, viral, fungal, or parasitic based on the category of infectious organism or agent involved. Other less common types of infection are also known in the art, including, e.g., infections involving rickettsiae, mycoplasmas, and agents causing scrapie, bovine spongiform encephalopthy (B SE), and prion diseases (e.g., kuru and Creutzfeldt-Jacob disease). Examples of bacteria, viruses, fungi, and parasites which cause infection are well known in the art. An infection can be acute, subacute, chronic, or latent, and it can be localized or systemic. As defined herein, a "chronic infection" refers to those infections that are not cleared by the normal actions of the innate or adaptive immune responses and persist in the subject for a long duration of time, on the order of weeks, months, and years. A chronic infection may reflect latency of the infectious agent, and may be include periods in which no infectious symptoms are present, i.e., asymptomatic periods. Examples of chronic infections include, but are not limited to, HIV infection and herpesvirus infections. Furthermore, an infection can be predominantly intracellular or extracellular during at least one phase of the infectious organism's or agent's life cycle in the host.

Exemplary viruses include, but are not limited to: Retroviridae (e.g., human immunodeficiency viruses, such as HIV-1 (also referred to as HTLV-III), HIV-2, LAV or HTLV-III/LAV, or HIV-III, and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); adenovirus; Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses, i.e., Rotavirus A, Rotavirus B. Rotavirus C); Birnaviridae; Hepadnaviridae (Hepatitis A and B viruses); Parvoviridae (parvoviruses); Papovaviridae (papilloma viruses, polyoma viruses); Adenoviridae (most adenoviruses); Herpesviridae (herpes simplex virus (HSV) 1 and 2, Human herpes virus 6, Human herpes virus 7, Human herpes virus 8, varicella zoster virus, cytomegalovirus (CMV), herpes virus; Epstein-Barr virus; Rous sarcoma virus; West Nile virus; Japanese equine encephalitis, Norwalk, papilloma virus, parvovirus B 19; Poxyiridae (variola viruses, vaccinia viruses, pox viruses); and Iridoviridae (e.g., African swine fever virus); Hepatitis D virus, Hepatitis E virus, and unclassified viruses (e.g., the etiological agents of Spongiform encephalopathies, the agent of delta hepatitis (thought to be a defective satellite of hepatitis B virus), the agents of non-A, non-B hepatitis (class 1=enterally transmitted; class 2=parenterally transmitted (i.e., Hepatitis C); Norwalk and related viruses, and astroviruses).

Bacteria include both Gram negative and Gram positive bacteria. Examples of Gram positive bacteria include, but are not limited to *Pasteurella* species, *Staphylococci* species, and *Streptococcus* species. Examples of Gram negative bacteria include, but are not limited to, *Escherichia coli*, *Pseudomonas* species, and *Salmonella* species. Specific examples of infectious bacteria include but are not limited to: *Helicobacter pyloris*, *Borrelia burgdorferi*, *Legionella pneumophilia*, *Mycobacteria* spp. (e.g., *M. tuberculosis*, *M. avium*, *M. intracellulare*, *M. kansasii*, *M. gordonae*, *M. leprae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic spp.), *Streptococcus pneumoniae*, pathogenic *Campylobacter* spp., *Enterococcus* spp., *Haemophilus influenzae* (*Hemophilus influenza* B, and *Hemophilus influenza* nontypable), *Bacillus anthracia, Corynebacterium diphtheriae, Corynebacterium* spp., *Erysipelothrix rhusiopathiae, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia, Actinomyces israelii, meningococcus, pertussis, pneumococcus, shigella, tetanus, Vibrio cholerae, yersinia, Pseudomonas* species, *Clostridia* species, *Salmonella typhi, Shigella dysenteriae, Yersinia pestis, Brucella* species, *Legionella pneumophila, Rickettsiae, Chlamydia, Clostridium perfringens, Clostridium botulinum, Staphylococcus aureus, Pseudomonas aeruginosa, Cryptosporidium parvum, Streptococcus pneumoniae*, and *Bordetella pertussis.*

Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavus, Blastomyces dermatitidis, Aspergillus clavatus, Cryptococcus neoformans, Chlamydia trachomatis, Coccidioides immitis, Cryptococcus laurentii, Cryptococcus albidus, Cryptococcus gattii, Nocardia* spp, *Histoplasma capsulatum, Pneumocystis jirovecii* (or *Pneumocystis carinii*), *Stachybotrys chartarum*, and any combination thereof.

Exemplary parasites include, but are not limited to: *Entamoeba histolytica; Plasmodium* species (*Plasmodium falciparum, Plasmodium malariae, Plasmodium ovale, Plasmodium vivax*), *Leishmania* species (*Leishmania tropica, Leishmania braziliensis, Leishmania donovani*), Toxoplasmosis (*Toxoplasma gondii*), *Trypanosoma gambiense, Trypanosoma rhodesiense* (African sleeping sickness), *Trypanosoma cruzi* (Chagas' disease), Helminths (flat worms, round worms), *Babesia microti, Babesia divergens, Giardia lamblia*, and any combination thereof.

The invention further relates to the use of an iRNA targeting CD274/PD-L1 and compositions containing at least one such iRNA for the treatment of an infectious disease, such as hepatitis B or a chronic bacterial infection, in combination with other pharmaceuticals and/or other therapeutic methods, e.g., with known pharmaceuticals and/or known therapeutic methods, such as, for example, those which are currently employed for treating such infectious diseases or disorders (e.g., antibiotics, anti-viral agents). For example, in certain embodiments, administration of a dsRNA targeting CD274/PD-L1 is administered in combination with an antibacterial agent. Examples of anti-bacterial agents useful for the methods described herein include, but are not limited to, natural penicillins, semi-synthetic penicillins, clavulanic acid, cephalolsporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, eurtreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Inipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

In other embodiments, administration of a dsRNA targeting CD274/PD-L1 is performed in combination with an antiviral medicament or agent. Exemplary antiviral agents useful for the methods described herein include, but are not limited to, immunoglobulins, amantadine, interferon, nucleoside analogues, and protease inhibitors. Specific examples of antiviral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

In other embodiments, administration of a dsRNA targeting CD274/PD-L1 is performed in combination with an antifungal medicament or agent. An "antifungal medicament" is an agent that kills or inhibits the growth or function of infective fungi. Anti-fungal medicaments are sometimes classified by their mechanism of action. Some anti-fungal agents function as cell wall inhibitors by inhibiting glucose synthase, other antifungal agents function by destabilizing membrane integrity, and other antifungal agents function by breaking down chitin (e.g., chitinase) or immunosuppression (501 cream). Thus, exemplary antifungal medicaments useful for the methods described herein include, but are not limited to, imidazoles, 501 cream, and Acrisorcin, Ambruticin, Amorolfine, Amphotericin B, Azaconazole, Azaserine, Basifungin, BAY 38-9502, Bifonazole, Biphenamine Hydrochloride, Bispyrithione Magsulfex, Butenafine, Butoconazole Nitrate, Calcium Undecylenate, Candicidin, Carbol-Fuchsin, Chitinase, Chlordantoin, Ciclopirox, Ciclopirox Olamine, Cilofungin, Cisconazole, Clotrimazole, Cuprimyxin, Denofungin, Dipyrithione, Doconazole, Econazole, Econazole Nitrate, Enilconazole, Ethonam Nitrate, Fenticonazole Nitrate, Filipin, FK 463, Fluconazole, Flucytosine, Fungimycin, Griseofulvin, Hamycin, Isoconazole, Itraconazole, Kalafungin, Ketoconazole, Lomofungin, Lydimycin, Mepartricin, Miconazole, Miconazole Nitrate, MK 991, Monensin, Monensin Sodium, Naftifine Hydrochloride, Neomycin Undecylenate, Nifuratel, Nifurmerone, Nitralamine Hydrochloride, Nystatin, Octanoic Acid, Orconazole Nitrate, Oxiconazole Nitrate, Oxifungin Hydrochloride, Parconazole Hydrochloride, Partricin, Potassium Iodide, Pradimicin, Proclonol, Pyrithione Zinc, Pyrrolnitrin, Rutamycin, Sanguinarium Chloride, Saperconazole, Scopafungin, Selenium Sulfide, Sertaconazole, Sinefungin, Sulconazole Nitrate, Terbinafine, Terconazole, Thiram, Ticlatone, Tioconazole, Tolciclate, Tolindate, Tolnaftate, Triacetin, Triafungin, UK 292, Undecylenic Acid, Viridofulvin, Voriconazole, Zinc Undecylenate, and Zinoconazole Hydrochloride.

In further embodiments, administration of a dsRNA targeting CD274/PD-L1 is administered in combination with an anti-parasitic medicament or agent. An "antiparasitic medicament" refers to an agent that kills or inhibits the growth or function of infective parasites. Examples of antiparasitic medicaments, also referred to as parasiticides, useful for the methods described herein include, but are not limited to, albendazole, amphotericin B, benznidazole, bithionol, chloroquine HCl, chloroquine phosphate, clindamycin, dehydroemetine, diethylcarbamazine, diloxanide furoate, doxycycline, eflomithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, thiabendazole, timidazole, trimethoprim-sulfamethoxazole, and tryparsamide, some of which are used alone or in combination with others.

The iRNA and an additional therapeutic agent can be administered in combination in the same composition, e.g., parenterally, or the additional therapeutic agent can be administered as part of a separate composition or by another method described herein.

Patients can be administered a therapeutic amount of iRNA, such as 0.01 mg/kg, 0.05 mg/kg, 0.1 mg/kg, 0.5 mg/kg, 1.0 mg/kg, 1.5 mg/kg, 2.0 mg/kg, or 2.5 mg/kg dsRNA. The iRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA can reduce CD274/PD-L1 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA, patients can be administered a smaller dose, such as a 5% infusion reaction, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels.

Genetic predisposition plays a role in the development of some cancers and hematological malignancies. Therefore, a patient in need of a CD274/PD-L1 iRNA may be identified by taking a family history, or, for example, screening for one or more genetic markers or variants. A healthcare provider, such as a doctor, nurse, or family member, can take a family history before prescribing or administering a CD274/PD-L1 dsRNA. For example, certain variants in the BRCA1 and BRCA2 genes are known to cause an increased risk for breast and ovarian cancers. A DNA test may also be performed on the patient to identify a mutation in the CD274/PD-L1 gene, before a CD274/PD-L1 dsRNA is administered to the patient.

Owing to the inhibitory effects on CD274/PD-L1 expression, a composition according to the invention or a pharmaceutical composition prepared therefrom can enhance the quality of life.

Methods for Modulating Expression of a CD274/PD-L1 Gene

In yet another aspect, the invention provides a method for modulating (e.g., inhibiting or activating) the expression of a CD274/PD-L1 gene in a mammal.

In one embodiment, the method includes administering a composition featured in the invention to the mammal such that expression or activity of the target CD274/PD-L1 gene is decreased, such as for an extended duration, e.g., at least two, three, four days or more, e.g., one week, two weeks, three weeks, or four weeks or longer. In some embodiments, CD274/PD-L1 expression or activity is decreased by at least 10%, at least 15%, at least 20%, at least 25%, at least 30%, at least 40%, at least 50%, or at least 60%, or more, as compared to pretreatment levels.

In another embodiment, the method includes administering a composition as described herein to a mammal such that expression or activity of the target CD274/PD-L1 gene is increased by e.g., at least 10% compared to an untreated animal. In some embodiments, the activation of CD274/PD-L1 occurs over an extended duration, e.g., at least two, three, four days or more, e.g., one week, two weeks, three weeks, four weeks, or more. Without wishing to be bound by theory, an iRNA can activate CD274/PD-L1 expression by stabilizing the CD274/PD-L1 mRNA transcript, interacting with a promoter in the genome, and/or inhibiting an inhibitor of CD274/PD-L1 expression.

Preferably, the iRNAs useful for the methods and compositions featured in the invention specifically target RNAs (primary or processed) of the target CD274/PD-L1 gene. Compositions and methods for inhibiting the expression of these CD274/PD-L1 genes using iRNAs can be prepared and performed as described elsewhere herein.

In one embodiment, the method includes administering a composition containing an iRNA, where the iRNA includes a nucleotide sequence that is complementary to at least a part of an RNA transcript of the CD274/PD-L1 gene of the mammal to be treated. When the organism to be treated is a mammal such as a human, the composition may be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 iRNA Synthesis

Source of Reagents

Where the source of a reagent is not specifically given herein, such reagent may be obtained from any supplier of reagents for molecular biology at a quality/purity standard for application in molecular biology.

Oligonucleotide Synthesis.

Applicants have used several different methods to generate the iRNA molecules described herein. This Example describes one approach that has been used. The ordinarily skilled artisan can use any method known in the art to prepare iRNAs as described herein.

Oligonucleotides are synthesized on an AKTA oligopilot synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O-N,N'-diisopropyl-2-cyanoethylphosphoramidite, 5'-O-dimethoxytrityl-N4-acetyl-2'-t-butyldimethylsilyl-cytidine-3'-O-N,N'-diisopropyl-2-cyanoethylphosphoramidite, 5'-O-dimethoxytrityl-N2-isobutryl-2'-t-butyldimethylsilyl-guanosine-3'-O-N,N'-diisopropyl-2-cyanoethylphosphoramidite, and 5'-O-dimethoxytrityl-2'-t-butyldimethylsilyl-uridine-3'-O-N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluoro-cytidine-3'-O-N,N'-diisopropyl-2-cyanoethyl-phosphoramidite and 5'-O-dimethoxytrityl-2'-fluoro-uridine-3'-O-N,N'-diisopropyl-2-cyanoethyl-phosphoramidite are purchased from (Promega). All phosphoramidites are used at a concentration of 0.2M in acetonitrile ($CH_3CN$) except for guanosine which is used at 0.2M concentration in 10% THF/ANC (v/v). Coupling/recycling time of 16 minutes is used. The activator is 5-ethyl thiotetrazole (0.75M, American International Chemicals); for the PO-oxidation iodine/water/pyridine is used and for the PS-oxidation PADS (2%) in 2,6-lutidine/ACN (1:1 v/v) is used.

3'-ligand conjugated strands are synthesized using solid support containing the corresponding ligand. For example, the introduction of cholesterol unit in the sequence is performed from a hydroxyprolinol-cholesterol phosphoramidite. Cholesterol is tethered to trans-4-hydroxyprolinol via a 6-aminohexanoate linkage to obtain a hydroxyprolinol-cholesterol moiety. 5'-end Cy-3 and Cy-5.5 (fluorophore) labeled iRNAs are synthesized from the corresponding Quasar-570 (Cy-3) phosphoramidite are purchased from Biosearch Technologies. Conjugation of ligands to 5'-end and or internal position is achieved by using appropriately protected ligand-phosphoramidite building block. An extended 15 min coupling of 0.1 M solution of phosphoramidite in anhydrous $CH_3CN$ in the presence of 5-(ethylthio)-1H-tetrazole activator to a solid-support-bound oligonucleotide. Oxidation of the internucleotide phosphite to the phosphate is carried out using standard iodine-water as reported (1) or by treatment with tert-butyl hydroperoxide/acetonitrile/water (10:87:3) with 10 min oxidation wait time conjugated oligonucleotide. Phosphorothioate is introduced by the oxidation of phosphite to phosphorothioate by using a sulfur transfer reagent such as DDTT (purchased from AM Chemicals), PADS and or Beaucage reagent. The cholesterol phosphoramidite is synthesized in house and used at a concentration of 0.1 M in dichloromethane. Coupling time for the cholesterol phosphoramidite is 16 minutes.

Deprotection I (Nucleobase Deprotection)

After completion of synthesis, the support is transferred to a 100 mL glass bottle (VWR). The oligonucleotide is cleaved from the support with simultaneous deprotection of base and phosphate groups with 80 mL of a mixture of ethanolic ammonia [ammonia:ethanol (3:1)] for 6.5 h at 55° C. The bottle is cooled briefly on ice and then the ethanolic ammonia mixture is filtered into a new 250-mL bottle. The CPG is washed with 2×40 mL portions of ethanol/water (1:1 v/v). The volume of the mixture is then reduced to ~30 mL by roto-vap. The mixture is then frozen on dry ice and dried under vacuum on a speed vac.

Deprotection II (Removal of 2'-TBDMS Group)

The dried residue is resuspended in 26 mL of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction is then quenched with 50 mL of 20 mM sodium acetate and the pH is adjusted to 6.5. Oligonucleotide is stored in a freezer until purification.

Analysis

The oligonucleotides are analyzed by high-performance liquid chromatography (HPLC) prior to purification and selection of buffer and column depends on nature of the sequence and or conjugated ligand.

HPLC Purification

The ligand-conjugated oligonucleotides are purified by reverse-phase preparative HPLC. The unconjugated oligonucleotides are purified by anion-exchange HPLC on a TSK gel column packed in house. The buffers are 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides are pooled, desalted, and lyophilized. Approximately 0.15 OD of desalted oligonucleotides are diluted in water to 150 µL and then pipetted into special vials for CGE and LC/MS analysis. Compounds are then analyzed by LC-ESMS and CGE.

iRNA Preparation

For the general preparation of iRNA, equimolar amounts of sense and antisense strand are heated in 1×PBS at 95° C. for 5 min and slowly cooled to room temperature. Integrity of the duplex is confirmed by HPLC analysis.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | adenosine |
| C | cytidine |
| G | guanosine |
| T | thymidine |
| U | uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

Example 2

CD274/PD-L1 siRNA Design and Synthesis

Transcripts

Oligonucleotide design was carried out to identify siRNAs targeting the gene encoding the human "CD274 molecule" (NCBI human symbol CD274) and the orthologous sequences from mice (*Mus musculus*) and rat (*Rattus norvegicus*). The design process used the CD274 transcripts NM_014143.2 from human (NCBI GeneId 29126; SEQ ID NO: 869, FIG. 1), NM_021893.2 from mouse (NCBI GeneId 60533; SEQ ID NO: 870, FIG. 2), and both XM_001079572.1 and XM_574652.2 from rat (NCBI GeneId 499342; SEQ ID NO: 871, FIG. 3 and SEQ ID NO: 872, FIG. 4 respectively). All sequences were obtained from the NCBI Refseq collection.

Two sets of oligos were designed: a human-specific set of oligos with 100% identity to human CD274, but less than 100% identity in mouse or rat, and a second set of siRNAs with 100% identity to the single mouse and both rat CD274 transcripts. All siRNA duplexes were designed with 100% identity to their respective CD274 transcripts.

A total of 456 sense human CD274/PD-L1 derived siRNA oligos were synthesized and formed into duplexes. The sense and corresponding antisense oligos are presented in Table 2 (SEQ ID NO: 5-SEQ ID NO: 436), Table 3 (SEQ ID NO: 437-SEQ ID NO: 868), and Table 5 (SEQ ID NO: 877-SEQ ID NO: 924) (human CD274/PD-L1, SEQ ID NO: 869) for use in the various aspects and embodiments described herein. In Tables 2 and 3, corresponding sense and antisense sequences have been designated or assigned adjacent sequence identifiers, e.g., SEQ ID NO: 5 (sense) and SEQ ID NO: 6 (antisense). In Table 5, corresponding sense and antisense sequences have not been designated adjacent sequence identifiers, but are found at the same row. In Table 5, sense oligonucleotide sequence identifiers are found at column 3 and the sense oligonucleotide sequences at column 5, and the antisense oligonucleotide sequence identifiers are found at column 6 and the antisense oligonucleotide sequences at column 8. For example, the corresponding antisense sequence for sense sequence SEQ ID NO.: 878 is SEQ ID NO: 902, at the same row.

siRNA Design and Specificity Prediction

The specificity of the 19mer oligo sets was predicted from each sequence. The CD274 siRNAs were used in a comprehensive search against their respective human, or mouse and rat transcriptomes (defined as the set of NM_ and XM_ records within the NCBI Refseq set) using the FASTA algorithm. The Python script 'offtargetFasta.py' was then used to parse the alignments and generate a score based on the position and number of mismatches between the siRNA and any potential 'off-target' transcript. The off-target score is weighted to emphasize differences in the 'seed' region of siRNAs, in positions 2-9 from the 5' end of the molecule. The off-target score is calculated as follows: mismatches between the oligo and the transcript are given penalties. A mismatch in the seed region in positions 2-9 of the oligo is given a penalty of 2.8; mismatches in the putative cleavage sites 10 and 11 are given a penalty of 1.2, and all other mismatches a penalty of 1. The off-target score for each oligo-transcript pair is then calculated by summing the mismatch penalties. The lowest off-target score from all the oligo-transcript pairs is then determined and used in subsequent sorting of oligos. Both siRNAs strands were assigned to a category of specificity according to the calculated scores: a score above 3 qualifies as highly specific, equal to 3 as specific and between 2.2 and 2.8 as moderate specific. In picking which oligos to synthesize, we sorted from high to low by the off-target score of the antisense strand and took the best (lowest off-target score) oligo pairs.

Synthesis of CD274 Sequences

CD274 sequences were synthesized on a MerMade 192 synthesizer at 1 µmol scale.

For all the sequences in the list, 'endolight' chemistry was applied as detailed below.

- All pyrimidines (cytosine and uridine) in the sense strand contained 2'-O-Methyl bases (2' O-Methyl C and 2'-O-Methyl U)
- In the antisense strand, pyrimidines adjacent to (towards 5' position) ribo A nucleoside were replaced with their corresponding 2-O-Methyl nucleosides
- A two base dTsdT extension at 3' end of both sense and antisense sequences was introduced The sequence file was converted to a text file to make it compatible for loading in the MerMade 192 synthesis software Synthesis, Cleavage and Deprotection:

The synthesis of CD274 sequences used solid supported oligonucleotide synthesis using phosphoramidite chemistry.

The synthesis of the above sequences was performed at 1 um scale in 96 well plates. The amidite solutions were prepared at 0.1M concentration and ethyl thio tetrazole (0.6M in Acetonitrile) was used as activator.

The synthesized sequences were cleaved and deprotected in 96 well plates, using methylamine in the first step and fluoride reagent in the second step. The crude sequences were precipitated using acetone:ethanol (80:20) mix and the pellet were re-suspended in 0.02M sodium acetate buffer. Samples from each sequence were analyzed by LC-MS to confirm the identity, UV for quantification and a selected set of samples by IEX chromatography to determine purity.

Purification and Desalting:

CD274 sequences were purified on AKTA explorer purification system using Source 15Q column. A column temperature of 65 C was maintained during purification. Sample injection and collection was performed in 96 well (1.8 mL -deep well) plates. A single peak corresponding to the full length sequence was collected in the eluent. The purified sequences were desalted on a Sephadex G25 column using AKTA purifier. The desalted CD274 sequences were analyzed for concentration (by UV measurement at A260) and purity (by ion exchange HPLC). The single strands were then submitted for annealing.

In Vitro Screening:

Cell Culture and Transfections:

RKO or Hep3B (ATCC, Manassas, Va.) cells were grown to near confluence at 37° C. in an atmosphere of 5% $CO_2$ in McCoy's or EMEM (respectively) (ATCC) supplemented with 10% FBS, streptomycin, and glutamine (ATCC) before being released from the plate by trypsinization. Reverse transfection was carried out by adding 5 µl of Opti-MEM to 5 µl of siRNA duplexes per well into a 96-well plate along with 10 µl of Opti-MEM plus 0.2 µl of Lipofectamine RNAiMax per well (Invitrogen, Carlsbad Calif. cat #13778-150) and incubated at room temperature for 15 minutes. 80 µl of complete growth media without antibiotic containing $2.0 \times 10^4$ Hela cells were then added. Cells were incubated for 24 hours prior to RNA purification. Experiments were performed at 0.1 or 10 nM final duplex concentration for single dose screens with each of the CD274 duplexes. A subset of 16 duplexes that showed robust silencing in the 10 nM and 0.1 nM screens were assayed over a range of concentrations from 10 nM to 10 fM using serial dilutions to determine their IC50.

Total RNA Isolation Using MagMAX-96 Total RNA Isolation Kit (Applied Biosystem, Forer City Calif., Part #: AM1830):

Cells were harvested and lysed in 140 µl of Lysis/Binding Solution then mixed for 1 minute at 850 rpm using and Eppendorf Thermomixer (the mixing speed was the same throughout the process). Twenty micro liters of magnetic beads and Lysis/Binding Enhancer mixture were added into cell-lysate and mixed for 5 minutes. Magnetic beads were captured using magnetic stand and the supernatant was removed without disturbing the beads. After removing supernatant, magnetic beads were washed with Wash Solution 1 (isopropanol added) and mixed for 1 minute. Beads were capture again and supernatant removed. Beads were then washed with 150 µl Wash Solution 2 (Ethanol added), captured and supernatant was removed. 50 µl of DNase mixture (MagMax turbo DNase Buffer and Turbo DNase) was then added to the beads and they were mixed for 10 to 15 minutes. After mixing, 100 µl of RNA Rebinding Solution was added and mixed for 3 minutes. Supernatant was removed and magnetic beads were washed again with 150 µl Wash Solution 2 and mixed for 1 minute and supernatant was removed completely. The magnetic beads were mixed for 2 minutes to dry before RNA was eluted with 50 µl of water.

cDNA Synthesis Using ABI High Capacity cDNA Reverse Transcription kit (Applied Biosystems, Foster City, Calif., Cat #4368813):

A master mix of 2 µl 10× Buffer, 0.8 µl 25×dNTPs, 2 µl Random primers, 1 µl Reverse Transcriptase, 1 µl RNase inhibitor and 3.2 µl of H2O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µl of cDNA were added to a master mix containing 0.5 µl GAPDH TaqMan Probe (Applied Biosystems Cat #4326317E), 0.5 µl CD274 (PD-L1) TaqMan probe (Applied Biosystems cat #Hs01125301_m1) and 5 µl Roche Probes Master Mix (Roche Cat #04887301001) in a total of 10 µl per well in a LightCycler 480 384 well plate (Roche cat #0472974001). Real time PCR was done in a LightCycler 480 Real Time PCR machine (Roche). Each duplex was tested in at least two independent transfections. For those siRNAs that were tested in RKO and Hep3B cells, at least three transfections were performed. Each transfection was assayed by qPCR in duplicate.

Real time data were analyzed using the ΔΔCt method. Each sample was normalized to GAPDH expression and knockdown was assessed relative to cells transfected with the non-targeting duplex AD-1955. IC50s were defined using a 4 parameter fit model in XLfit.

In the experiments described herein, IC50 values were determined for a set of exemplary inhibitory duplex sequences in duplicate experiments. For example, IC50 values for inhibitory duplex AD-31066-b1 (SEQ ID NO: 890 and SEQ ID NO: 914), were 0.456978463 nM and 0.817398666 nM; for inhibitory duplex AD-31067-b1 (SEQ ID NO: 891 and SEQ ID NO: 915), 0.612976729 nM and 2.901972117 nM; for inhibitory duplex AD-31068-b1 (SEQ ID NO: 892 and SEQ ID NO: 915), 0.762691728 nM and 0.46079339 nM; and for inhibitory duplex AD-31069-b1 (SEQ ID NO: 893 and SEQ ID NO: 915), 0.30630503 nM and 0.261020215 nM.

Other embodiments are in the claims.

TABLE 2

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 5 | S | 415 | CGACUACAAGCGAAUUACU |
| 6 | AS | 415 | AGUAAUUCGCUUGUAGUCG |
| 7 | S | 1236 | UCCUAGGAAGACGGGUUGA |
| 8 | AS | 1236 | UCAACCCGUCUUCCUAGGA |
| 9 | S | 411 | GUGCCGACUACAAGCGAAU |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 10 | AS | 411 | AUUCGCUUGUAGUCGGCAC |
| 11 | S | 414 | CCGACUACAAGCGAAUUAC |
| 12 | AS | 414 | GUAAUUCGCUUGUAGUCGG |
| 13 | S | 413 | GCCGACUACAAGCGAAUUA |
| 14 | AS | 413 | UAAUUCGCUUGUAGUCGGC |
| 15 | S | 973 | GUUUAGGGGUUCAUCGGGG |
| 16 | AS | 973 | CCCCGAUGAACCCCUAAAC |
| 17 | S | 1462 | GAUGUUACAAUUUUGUCGC |
| 18 | AS | 1462 | GCGACAAAAUUGUAACAUC |
| 19 | S | 104 | GCAUUUACUGUCACGGUUC |
| 20 | AS | 104 | GAACCGUGACAGUAAAUGC |
| 21 | S | 786 | GAGCCAUCUUAUUAUGCCU |
| 22 | AS | 786 | AGGCAUAAUAAGAUGGCUC |
| 23 | S | 1338 | AGUCUCAGUGUUGGAACGG |
| 24 | AS | 1338 | CCGUUCCAACACUGAGACU |
| 25 | S | 681 | CUUUUAGGAGAUUAGAUCC |
| 26 | AS | 681 | GGAUCUAAUCUCCUAAAAG |
| 27 | S | 1067 | AUGGAACCUGGCGAAAGCA |
| 28 | AS | 1067 | UGCUUUCGCCAGGUUCCAU |
| 29 | S | 529 | CUACCCCAAGGCCGAAGUC |
| 30 | AS | 529 | GACUUCGGCCUUGGGGUAG |
| 31 | S | 1068 | UGGAACCUGGCGAAAGCAG |
| 32 | AS | 1068 | CUGCUUUCGCCAGGUUCCA |
| 33 | S | 134 | UAUGUGGUAGAGUAUGGUA |
| 34 | AS | 134 | UACCAUACUCUACCACAUA |
| 35 | S | 723 | UGGUCAUCCCAGAACUACC |
| 36 | AS | 723 | GGUAGUUCUGGGAUGACCA |
| 37 | S | 105 | CAUUUACUGUCACGGUUCC |
| 38 | AS | 105 | GGAACCGUGACAGUAAAUG |
| 39 | S | 785 | GGAGCCAUCUUAUUAUGCC |
| 40 | AS | 785 | GGCAUAAUAAGAUGGCUCC |
| 41 | S | 416 | GACUACAAGCGAAUUACUG |
| 42 | AS | 416 | CAGUAAUUCGCUUGUAGUC |
| 43 | S | 710 | CAUACAGCUGAAUUGGUCA |
| 44 | AS | 710 | UGACCAAUUCAGCUGUAUG |
| 45 | S | 206 | GCACUAAUUGUCUAUUGGG |
| 46 | AS | 206 | CCCAAUAGACAAUUAGUGC |
| 47 | S | 974 | UUUAGGGGUUCAUCGGGGC |
| 48 | AS | 974 | GCCCCGAUGAACCCCUAAA |
| 49 | S | 962 | CUCAACCUGUGGUUUAGGG |
| 50 | AS | 962 | CCCUAAACCACAGGUUGAG |
| 51 | S | 1260 | CCUAAUUUGAGGGUCAGUU |
| 52 | AS | 1260 | AACUGACCCUCAAAUUAGG |
| 53 | S | 961 | UCUCAACCUGUGGUUUAGG |
| 54 | AS | 961 | CCUAAACCACAGGUUGAGA |
| 55 | S | 683 | UUUAGGAGAUUAGAUCCUG |
| 56 | AS | 683 | CAGGAUCUAAUCUCCUAAA |
| 57 | S | 1226 | CCAUUGCUCAUCCUAGGAA |
| 58 | AS | 1226 | UUCCUAGGAUGAGCAAUGG |
| 59 | S | 122 | CCCAAGGACCUAUAUGUGG |
| 60 | AS | 122 | CCACAUAUAGGUCCUUGGG |
| 61 | S | 1245 | GACGGGUUGAGAAUCCCUA |
| 62 | AS | 1245 | UAGGGAUUCUCAACCCGUC |
| 63 | S | 203 | GCUGCACUAAUUGUCUAUU |
| 64 | AS | 203 | AAUAGACAAUUAGUGCAGC |
| 65 | S | 108 | UUACUGUCACGGUUCCCAA |
| 66 | AS | 108 | UUGGGAACCGUGACAGUAA |
| 67 | S | 722 | UUGGUCAUCCCAGAACUAC |
| 68 | AS | 722 | GUAGUUCUGGGAUGACCAA |
| 69 | S | 408 | GUGGUGCCGACUACAAGCG |
| 70 | AS | 408 | CGCUUGUAGUCGGCACCAC |
| 71 | S | 1020 | CCGUGGGAUGCAGGCAAUG |
| 72 | AS | 1020 | CAUUGCCUGCAUCCCACGG |
| 73 | S | 789 | CCAUCUUAUUAUGCCUUGG |
| 74 | AS | 789 | CCAAGGCAUAAUAAGAUGG |
| 75 | S | 99 | UGAACGCAUUUACUGUCAC |
| 76 | AS | 99 | GUGACAGUAAAUGCGUUCA |
| 77 | S | 806 | GGUGUAGCACUGACAUUCA |
| 78 | AS | 806 | UGAAUGUCAGUGCUACACC |
| 79 | S | 98 | CUGAACGCAUUUACUGUCA |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 80 | AS | 98 | UGACAGUAAAUGCGUUCAG |
| 81 | S | 124 | CAAGGACCUAUAUGUGGUA |
| 82 | AS | 124 | UACCACAUAUAGGUCCUUG |
| 83 | S | 1132 | GAGACCUUGAUACUUUCAA |
| 84 | AS | 1132 | UUGAAAGUAUCAAGGUCUC |
| 85 | S | 989 | GGGCUGAGCGUGACAAGAG |
| 86 | AS | 989 | CUCUUGUCACGCUCAGCCC |
| 87 | S | 404 | UAUGGUGGUGCCGACUACA |
| 88 | AS | 404 | UGUAGUCGGCACCACCAUA |
| 89 | S | 275 | AAGGUUCAGCAUAGUAGCU |
| 90 | AS | 275 | AGCUACUAUGCUGAACCUU |
| 91 | S | 1235 | AUCCUAGGAAGACGGGUUG |
| 92 | AS | 1235 | CAACCCGUCUUCCUAGGAU |
| 93 | S | 1463 | AUGUUACAAUUUUGUCGCC |
| 94 | AS | 1463 | GGCGACAAAAUUGUAACAU |
| 95 | S | 106 | AUUUACUGUCACGGUUCCC |
| 96 | AS | 106 | GGGAACCGUGACAGUAAAU |
| 97 | S | 103 | CGCAUUUACUGUCACGGUU |
| 98 | AS | 103 | AACCGUGACAGUAAAUGCG |
| 99 | S | 276 | AGGUUCAGCAUAGUAGCUA |
| 100 | AS | 276 | UAGCUACUAUGCUGAACCU |
| 101 | S | 11 | CACCAGCCGCGCUUCUGUC |
| 102 | AS | 11 | GACAGAAGCGCGGCUGGUG |
| 103 | S | 18 | CGCGCUUCUGUCCGCCUGC |
| 104 | AS | 18 | GCAGGCGGACAGAAGCGCG |
| 105 | S | 50 | AAGAUGAGGAUAUUUGCUG |
| 106 | AS | 50 | CAGCAAAUAUCCUCAUCUU |
| 107 | S | 70 | CUUUAUAUUCAUGACCUAC |
| 108 | AS | 70 | GUAGGUCAUGAAUAUAAAG |
| 109 | S | 76 | AUUCAUGACCUACUGGCAU |
| 110 | AS | 76 | AUGCCAGUAGGUCAUGAAU |
| 111 | S | 78 | UCAUGACCUACUGGCAUUU |
| 112 | AS | 78 | AAAUGCCAGUAGGUCAUGA |
| 113 | S | 86 | UACUGGCAUUUGCUGAACG |
| 114 | AS | 86 | CGUUCAGCAAAUGCCAGUA |
| 115 | S | 88 | CUGGCAUUUGCUGAACGCA |
| 116 | AS | 88 | UGCGUUCAGCAAAUGCCAG |
| 117 | S | 93 | AUUUGCUGAACGCAUUUAC |
| 118 | AS | 93 | GUAAAUGCGUUCAGCAAAU |
| 119 | S | 94 | UUUGCUGAACGCAUUUACU |
| 120 | AS | 94 | AGUAAAUGCGUUCAGCAAA |
| 121 | S | 97 | GCUGAACGCAUUUACUGUC |
| 122 | AS | 97 | GACAGUAAAUGCGUUCAGC |
| 123 | S | 107 | UUUACUGUCACGGUUCCCA |
| 124 | AS | 107 | UGGGAACCGUGACAGUAAA |
| 125 | S | 116 | ACGGUUCCCAAGGACCUAU |
| 126 | AS | 116 | AUAGGUCCUUGGGAACCGU |
| 127 | S | 117 | CGGUUCCCAAGGACCUAUA |
| 128 | AS | 117 | UAUAGGUCCUUGGGAACCG |
| 129 | S | 118 | GGUUCCCAAGGACCUAUAU |
| 130 | AS | 118 | AUAUAGGUCCUUGGGAACC |
| 131 | S | 119 | GUUCCCAAGGACCUAUAUG |
| 132 | AS | 119 | CAUAUAGGUCCUUGGGAAC |
| 133 | S | 128 | GACCUAUAUGUGGUAGAGU |
| 134 | AS | 128 | ACUCUACCACAUAUAGGUC |
| 135 | S | 138 | UGGUAGAGUAUGGUAGCAA |
| 136 | AS | 138 | UUGCUACCAUACUCUACCA |
| 137 | S | 145 | GUAUGGUAGCAAUAUGACA |
| 138 | AS | 145 | UGUCAUAUUGCUACCAUAC |
| 139 | S | 148 | UGGUAGCAAUAUGACAAUU |
| 140 | AS | 148 | AAUUGUCAUAUUGCUACCA |
| 141 | S | 149 | GGUAGCAAUAUGACAAUUG |
| 142 | AS | 149 | CAAUUGUCAUAUUGCUACC |
| 143 | S | 152 | AGCAAUAUGACAAUUGAAU |
| 144 | AS | 152 | AUUCAAUUGUCAUAUUGCU |
| 145 | S | 154 | CAAUAUGACAAUUGAAUGC |
| 146 | AS | 154 | GCAUUCAAUUGUCAUAUUG |
| 147 | S | 155 | AAUAUGACAAUUGAAUGCA |
| 148 | AS | 155 | UGCAUUCAAUUGUCAUAUU |
| 149 | S | 156 | AUAUGACAAUUGAAUGCAA |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 150 | AS | 156 | UUGCAUUCAAUUGUCAUAU |
| 151 | S | 162 | CAAUUGAAUGCAAAUUCCC |
| 152 | AS | 162 | GGGAAUUUGCAUUCAAUUG |
| 153 | S | 166 | UGAAUGCAAAUUCCCAGUA |
| 154 | AS | 166 | UACUGGGAAUUUGCAUUCA |
| 155 | S | 168 | AAUGCAAAUUCCCAGUAGA |
| 156 | AS | 168 | UCUACUGGGAAUUUGCAUU |
| 157 | S | 187 | AAAACAAUUAGACCUGGCU |
| 158 | AS | 187 | AGCCAGGUCUAAUUGUUUU |
| 159 | S | 188 | AAACAAUUAGACCUGGCUG |
| 160 | AS | 188 | CAGCCAGGUCUAAUUGUUU |
| 161 | S | 202 | GGCUGCACUAAUUGUCUAU |
| 162 | AS | 202 | AUAGACAAUUAGUGCAGCC |
| 163 | S | 205 | UGCACUAAUUGUCUAUUGG |
| 164 | AS | 205 | CCAAUAGACAAUUAGUGCA |
| 165 | S | 218 | UAUUGGGAAAUGGAGGAUA |
| 166 | AS | 218 | UAUCCUCCAUUUCCCAAUA |
| 167 | S | 248 | CAAUUUGUGCAUGGAGAGG |
| 168 | AS | 248 | CCUCUCCAUGCACAAAUUG |
| 169 | S | 271 | CCUGAAGGUUCAGCAUAGU |
| 170 | AS | 271 | ACUAUGCUGAACCUUCAGG |
| 171 | S | 273 | UGAAGGUUCAGCAUAGUAG |
| 172 | AS | 273 | CUACUAUGCUGAACCUUCA |
| 173 | S | 277 | GGUUCAGCAUAGUAGCUAC |
| 174 | AS | 277 | GUAGCUACUAUGCUGAACC |
| 175 | S | 278 | GUUCAGCAUAGUAGCUACA |
| 176 | AS | 278 | UGUAGCUACUAUGCUGAAC |
| 177 | S | 279 | UUCAGCAUAGUAGCUACAG |
| 178 | AS | 279 | CUGUAGCUACUAUGCUGAA |
| 179 | S | 284 | CAUAGUAGCUACAGACAGA |
| 180 | AS | 284 | UCUGUCUGUAGCUACUAUG |
| 181 | S | 285 | AUAGUAGCUACAGACAGAG |
| 182 | AS | 285 | CUCUGUCUGUAGCUACUAU |
| 183 | S | 292 | CUACAGACAGAGGGCCCGG |
| 184 | AS | 292 | CCGGGCCCUCUGUCUGUAG |
| 185 | S | 341 | GCUGCACUUCAGAUCACAG |
| 186 | AS | 341 | CUGUGAUCUGAAGUGCAGC |
| 187 | S | 342 | CUGCACUUCAGAUCACAGA |
| 188 | AS | 342 | UCUGUGAUCUGAAGUGCAG |
| 189 | S | 343 | UGCACUUCAGAUCACAGAU |
| 190 | AS | 343 | AUCUGUGAUCUGAAGUGCA |
| 191 | S | 344 | GCACUUCAGAUCACAGAUG |
| 192 | AS | 344 | CAUCUGUGAUCUGAAGUGC |
| 193 | S | 365 | AAAUGCAGGAUGCAGGGG |
| 194 | AS | 365 | CCCCUGCAUCCUGCAAUUU |
| 195 | S | 371 | CAGGAUGCAGGGGUGUACC |
| 196 | AS | 371 | GGUACACCCCUGCAUCCUG |
| 197 | S | 373 | GGAUGCAGGGGUGUACCGC |
| 198 | AS | 373 | GCGGUACACCCCUGCAUCC |
| 199 | S | 385 | GUACCGCUGCAUGAUCAGC |
| 200 | AS | 385 | GCUGAUCAUGCAGCGGUAC |
| 201 | S | 387 | ACCGCUGCAUGAUCAGCUA |
| 202 | AS | 387 | UAGCUGAUCAUGCAGCGGU |
| 203 | S | 395 | AUGAUCAGCUAUGGUGGUG |
| 204 | AS | 395 | CACCACCAUAGCUGAUCAU |
| 205 | S | 402 | GCUAUGGUGGUGCCGACUA |
| 206 | AS | 402 | UAGUCGGCACCACCAUAGC |
| 207 | S | 412 | UGCCGACUACAAGCGAAUU |
| 208 | AS | 412 | AAUUCGCUUGUAGUCGGCA |
| 209 | S | 423 | AGCGAAUUACUGUGAAAGU |
| 210 | AS | 423 | ACUUUCACAGUAAUUCGCU |
| 211 | S | 424 | GCGAAUUACUGUGAAAGUC |
| 212 | AS | 424 | GACUUUCACAGUAAUUCGC |
| 213 | S | 425 | CGAAUUACUGUGAAAGUCA |
| 214 | AS | 425 | UGACUUUCACAGUAAUUCG |
| 215 | S | 428 | AUUACUGUGAAAGUCAAUG |
| 216 | AS | 428 | CAUUGACUUUCACAGUAAU |
| 217 | S | 430 | UACUGUGAAAGUCAAUGCC |
| 218 | AS | 430 | GGCAUUGACUUUCACAGUA |
| 219 | S | 437 | AAAGUCAAUGCCCCAUACA |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 220 | AS | 437 | UGUAUGGGCAUUGACUUU |
| 221 | S | 440 | GUCAAUGCCCCAUACAACA |
| 222 | AS | 440 | UGUUGUAUGGGGCAUUGAC |
| 223 | S | 472 | AAUUUUGGUUGUGGAUCCA |
| 224 | AS | 472 | UGGAUCCACAACCAAAAUU |
| 225 | S | 473 | AUUUUGGUUGUGGAUCCAG |
| 226 | AS | 473 | CUGGAUCCACAACCAAAAU |
| 227 | S | 490 | AGUCACCUCUGAACAUGAA |
| 228 | AS | 490 | UUCAUGUUCAGAGGUGACU |
| 229 | S | 494 | ACCUCUGAACAUGAACUGA |
| 230 | AS | 494 | UCAGUUCAUGUUCAGAGGU |
| 231 | S | 495 | CCUCUGAACAUGAACUGAC |
| 232 | AS | 495 | GUCAGUUCAUGUUCAGAGG |
| 233 | S | 499 | UGAACAUGAACUGACAUGU |
| 234 | AS | 499 | ACAUGUCAGUUCAUGUUCA |
| 235 | S | 502 | ACAUGAACUGACAUGUCAG |
| 236 | AS | 502 | CUGACAUGUCAGUUCAUGU |
| 237 | S | 503 | CAUGAACUGACAUGUCAGG |
| 238 | AS | 503 | CCUGACAUGUCAGUUCAUG |
| 239 | S | 505 | UGAACUGACAUGUCAGGCU |
| 240 | AS | 505 | AGCCUGACAUGUCAGUUCA |
| 241 | S | 506 | GAACUGACAUGUCAGGCUG |
| 242 | AS | 506 | CAGCCUGACAUGUCAGUUC |
| 243 | S | 511 | GACAUGUCAGGCUGAGGGC |
| 244 | AS | 511 | GCCCUCAGCCUGACAUGUC |
| 245 | S | 515 | UGUCAGGCUGAGGGCUACC |
| 246 | AS | 515 | GGUAGCCCUCAGCCUGACA |
| 247 | S | 530 | UACCCCAAGGCCGAAGUCA |
| 248 | AS | 530 | UGACUUCGGCCUUGGGGUA |
| 249 | S | 536 | AAGGCCGAAGUCAUCUGGA |
| 250 | AS | 536 | UCCAGAUGACUUCGGCCUU |
| 251 | S | 541 | CGAAGUCAUCUGGACAAGC |
| 252 | AS | 541 | GCUUGUCCAGAUGACUUCG |
| 253 | S | 547 | CAUCUGGACAAGCAGUGAC |
| 254 | AS | 547 | GUCACUGCUUGUCCAGAUG |
| 255 | S | 557 | AGCAGUGACCAUCAAGUCC |
| 256 | AS | 557 | GGACUUGAUGGUCACUGCU |
| 257 | S | 568 | UCAAGUCCUGAGUGGUAAG |
| 258 | AS | 568 | CUUACCACUCAGGACUUGA |
| 259 | S | 645 | GAAUCAACACAACAACUAA |
| 260 | AS | 645 | UUAGUUGUUGUGUUGAUUC |
| 261 | S | 646 | AAUCAACACAACAACUAAU |
| 262 | AS | 646 | AUUAGUUGUUGUGUUGAUU |
| 263 | S | 671 | UUCUACUGCACUUUUAGGA |
| 264 | AS | 671 | UCCUAAAAGUGCAGUAGAA |
| 265 | S | 678 | GCACUUUUAGGAGAUUAGA |
| 266 | AS | 678 | UCUAAUCUCCUAAAAGUGC |
| 267 | S | 682 | UUUUAGGAGAUUAGAUCCU |
| 268 | AS | 682 | AGGAUCUAAUCUCCUAAAA |
| 269 | S | 684 | UUAGGAGAUUAGAUCCUGA |
| 270 | AS | 684 | UCAGGAUCUAAUCUCCUAA |
| 271 | S | 685 | UAGGAGAUUAGAUCCUGAG |
| 272 | AS | 685 | CUCAGGAUCUAAUCUCCUA |
| 273 | S | 686 | AGGAGAUUAGAUCCUGAGG |
| 274 | AS | 686 | CCUCAGGAUCUAAUCUCCU |
| 275 | S | 687 | GGAGAUUAGAUCCUGAGGA |
| 276 | AS | 687 | UCCUCAGGAUCUAAUCUCC |
| 277 | S | 706 | AAACCAUACAGCUGAAUUG |
| 278 | AS | 706 | CAAUUCAGCUGUAUGGUUU |
| 279 | S | 707 | AACCAUACAGCUGAAUUGG |
| 280 | AS | 707 | CCAAUUCAGCUGUAUGGUU |
| 281 | S | 709 | CCAUACAGCUGAAUUGGUC |
| 282 | AS | 709 | GACCAAUUCAGCUGUAUGG |
| 283 | S | 711 | AUACAGCUGAAUUGGUCAU |
| 284 | AS | 711 | AUGACCAAUUCAGCUGUAU |
| 285 | S | 716 | GCUGAAUUGGUCAUCCCAG |
| 286 | AS | 716 | CUGGGAUGACCAAUUCAGC |
| 287 | S | 724 | GGUCAUCCCAGAACUACCU |
| 288 | AS | 724 | AGGUAGUUCUGGGAUGACC |
| 289 | S | 744 | UGGCACAUCCUCCAAAUGA |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 290 | AS | 744 | UCAUUUGGAGGAUGUGCCA |
| 291 | S | 760 | UGAAAGGACUCACUUGGUA |
| 292 | AS | 760 | UACCAAGUGAGUCCUUUCA |
| 293 | S | 764 | AGGACUCACUUGGUAAUUC |
| 294 | AS | 764 | GAAUUACCAAGUGAGUCCU |
| 295 | S | 766 | GACUCACUUGGUAAUUCUG |
| 296 | AS | 766 | CAGAAUUACCAAGUGAGUC |
| 297 | S | 769 | UCACUUGGUAAUUCUGGGA |
| 298 | AS | 769 | UCCCAGAAUUACCAAGUGA |
| 299 | S | 775 | GGUAAUUCUGGGAGCCAUC |
| 300 | AS | 775 | GAUGGCUCCCAGAAUUACC |
| 301 | S | 776 | GUAAUUCUGGGAGCCAUCU |
| 302 | AS | 776 | AGAUGGCUCCCAGAAUUAC |
| 303 | S | 781 | UCUGGGAGCCAUCUUAUUA |
| 304 | AS | 781 | UAAUAAGAUGGCUCCCAGA |
| 305 | S | 782 | CUGGGAGCCAUCUUAUUAU |
| 306 | AS | 782 | AUAAUAAGAUGGCUCCCAG |
| 307 | S | 783 | UGGGAGCCAUCUUAUUAUG |
| 308 | AS | 783 | CAUAAUAAGAUGGCUCCCA |
| 309 | S | 784 | GGGAGCCAUCUUAUUAUGC |
| 310 | AS | 784 | GCAUAAUAAGAUGGCUCCC |
| 311 | S | 787 | AGCCAUCUUAUUAUGCCUU |
| 312 | AS | 787 | AAGGCAUAAUAAGAUGGCU |
| 313 | S | 791 | AUCUUAUUAUGCCUUGGUG |
| 314 | AS | 791 | CACCAAGGCAUAAUAAGAU |
| 315 | S | 795 | UAUUAUGCCUUGGUGUAGC |
| 316 | AS | 795 | GCUACACCAAGGCAUAAUA |
| 317 | S | 796 | AUUAUGCCUUGGUGUAGCA |
| 318 | AS | 796 | UGCUACACCAAGGCAUAAU |
| 319 | S | 800 | UGCCUUGGUGUAGCACUGA |
| 320 | AS | 800 | UCAGUGCUACACCAAGGCA |
| 321 | S | 805 | UGGUGUAGCACUGACAUUC |
| 322 | AS | 805 | GAAUGUCAGUGCUACACCA |
| 323 | S | 809 | GUAGCACUGACAUUCAUCU |
| 324 | AS | 809 | AGAUGAAUGUCAGUGCUAC |
| 325 | S | 815 | CUGACAUUCAUCUUCCGUU |
| 326 | AS | 815 | AACGGAAGAUGAAUGUCAG |
| 327 | S | 841 | AGGGAGAAUGAUGGAUGUG |
| 328 | AS | 841 | CACAUCCAUCAUUCUCCCU |
| 329 | S | 868 | UGGCAUCCAAGAUACAAAC |
| 330 | AS | 868 | GUUUGUAUCUUGGAUGCCA |
| 331 | S | 869 | GGCAUCCAAGAUACAAACU |
| 332 | AS | 869 | AGUUUGUAUCUUGGAUGCC |
| 333 | S | 870 | GCAUCCAAGAUACAAACUC |
| 334 | AS | 870 | GAGUUUGUAUCUUGGAUGC |
| 335 | S | 896 | CAAAGUGAUACACAUUUGG |
| 336 | AS | 896 | CCAAAUGUGUAUCACUUUG |
| 337 | S | 900 | GUGAUACACAUUUGGAGGA |
| 338 | AS | 900 | UCCUCCAAAUGUGUAUCAC |
| 339 | S | 905 | ACACAUUUGGAGGAGACGU |
| 340 | AS | 905 | ACGUCUCCUCCAAAUGUGU |
| 341 | S | 907 | ACAUUUGGAGGAGACGUAA |
| 342 | AS | 907 | UUACGUCUCCUCCAAAUGU |
| 343 | S | 908 | CAUUUGGAGGAGACGUAAU |
| 344 | AS | 908 | AUUACGUCUCCUCCAAAUG |
| 345 | S | 913 | GGAGGAGACGUAAUCCAGC |
| 346 | AS | 913 | GCUGGAUUACGUCUCCUCC |
| 347 | S | 920 | ACGUAAUCCAGCAUUGGAA |
| 348 | AS | 920 | UUCCAAUGCUGGAUUACGU |
| 349 | S | 965 | AACCUGUGGUUUAGGGGUU |
| 350 | AS | 965 | AACCCCUAAACCACAGGUU |
| 351 | S | 967 | CCUGUGGUUUAGGGGUUCA |
| 352 | AS | 967 | UGAACCCCUAAACCACAGG |
| 353 | S | 968 | CUGUGGUUUAGGGGUUCAU |
| 354 | AS | 968 | AUGAACCCCUAAACCACAG |
| 355 | S | 971 | UGGUUUAGGGGUUCAUCGG |
| 356 | AS | 971 | CCGAUGAACCCCUAAACCA |
| 357 | S | 972 | GGUUUAGGGGUUCAUCGGG |
| 358 | AS | 972 | CCCGAUGAACCCCUAAACC |
| 359 | S | 1031 | AGGCAAUGUGGGACUUAAA |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 360 | AS | 1031 | UUUAAGUCCCACAUUGCCU |
| 361 | S | 1032 | GGCAAUGUGGGACUUAAAA |
| 362 | AS | 1032 | UUUUAAGUCCCACAUUGCC |
| 363 | S | 1033 | GCAAUGUGGGACUUAAAAG |
| 364 | AS | 1033 | CUUUUAAGUCCCACAUUGC |
| 365 | S | 1062 | UGAAAAUGGAACCUGGCGA |
| 366 | AS | 1062 | UCGCCAGGUUCCAUUUUCA |
| 367 | S | 1064 | AAAAUGGAACCUGGCGAAA |
| 368 | AS | 1064 | UUUCGCCAGGUUCCAUUUU |
| 369 | S | 1128 | GAGGGAGACCUUGAUACUU |
| 370 | AS | 1128 | AAGUAUCAAGGUCUCCCUC |
| 371 | S | 1129 | AGGGAGACCUUGAUACUUU |
| 372 | AS | 1129 | AAAGUAUCAAGGUCUCCCU |
| 373 | S | 1133 | AGACCUUGAUACUUUCAAA |
| 374 | AS | 1133 | UUUGAAAGUAUCAAGGUCU |
| 375 | S | 1138 | UUGAUACUUUCAAAUGCCU |
| 376 | AS | 1138 | AGGCAUUUGAAAGUAUCAA |
| 377 | S | 1150 | AAUGCCUGAGGGGCUCAUC |
| 378 | AS | 1150 | GAUGAGCCCCUCAGGCAUU |
| 379 | S | 1152 | UGCCUGAGGGGCUCAUCGA |
| 380 | AS | 1152 | UCGAUGAGCCCCUCAGGCA |
| 381 | S | 1160 | GGGCUCAUCGACGCCUGUG |
| 382 | AS | 1160 | CACAGGCGUCGAUGAGCCC |
| 383 | S | 1161 | GGCUCAUCGACGCCUGUGA |
| 384 | AS | 1161 | UCACAGGCGUCGAUGAGCC |
| 385 | S | 1166 | AUCGACGCCUGUGACAGGG |
| 386 | AS | 1166 | CCCUGUCACAGGCGUCGAU |
| 387 | S | 1205 | AGGAGCCUCCAAGCAAAUC |
| 388 | AS | 1205 | GAUUUGCUUGGAGGCUCCU |
| 389 | S | 1224 | AUCCAUUGCUCAUCCUAGG |
| 390 | AS | 1224 | CCUAGGAUGAGCAAUGGAU |
| 391 | S | 1233 | UCAUCCUAGGAAGACGGGU |
| 392 | AS | 1233 | ACCCGUCUUCCUAGGAUGA |
| 393 | S | 1234 | CAUCCUAGGAAGACGGGUU |
| 394 | AS | 1234 | AACCCGUCUUCCUAGGAUG |
| 395 | S | 1238 | CUAGGAAGACGGGUUGAGA |
| 396 | AS | 1238 | UCUCAACCCGUCUUCCUAG |
| 397 | S | 1246 | ACGGGUUGAGAAUCCCUAA |
| 398 | AS | 1246 | UUAGGGAUUCUCAACCCGU |
| 399 | S | 1254 | AGAAUCCCUAAUUUGAGGG |
| 400 | AS | 1254 | CCCUCAAAUUAGGGAUUCU |
| 401 | S | 1256 | AAUCCCUAAUUUGAGGGUC |
| 402 | AS | 1256 | GACCCUCAAAUUAGGGAUU |
| 403 | S | 1259 | CCCUAAUUUGAGGGUCAGU |
| 404 | AS | 1259 | ACUGACCCUCAAAUUAGGG |
| 405 | S | 1302 | CACUCAAUGCCUCAAUUUG |
| 406 | AS | 1302 | CAAAUUGAGGCAUUGAGUG |
| 407 | S | 1303 | ACUCAAUGCCUCAAUUUGU |
| 408 | AS | 1303 | ACAAAUUGAGGCAUUGAGU |
| 409 | S | 1323 | UUCUGCAUGACUGAGAGUC |
| 410 | AS | 1323 | GACUCUCAGUCAUGCAGAA |
| 411 | S | 1324 | UCUGCAUGACUGAGAGUCU |
| 412 | AS | 1324 | AGACUCUCAGUCAUGCAGA |
| 413 | S | 1327 | GCAUGACUGAGAGUCUCAG |
| 414 | AS | 1327 | CUGAGACUCUCAGUCAUGC |
| 415 | S | 1331 | GACUGAGAGUCUCAGUGUU |
| 416 | AS | 1331 | AACACUGAGACUCUCAGUC |
| 417 | S | 1337 | GAGUCUCAGUGUUGGAACG |
| 418 | AS | 1337 | CGUUCCAACACUGAGACUC |
| 419 | S | 1341 | CUCAGUGUUGGAACGGGAC |
| 420 | AS | 1341 | GUCCCGUUCCAACACUGAG |
| 421 | S | 1386 | UUAUUUUGAGUCUGUGAGG |
| 422 | AS | 1386 | CCUCACAGACUCAAAAUAA |
| 423 | S | 1388 | AUUUUGAGUCUGUGAGGUC |
| 424 | AS | 1388 | GACCUCACAGACUCAAAAU |
| 425 | S | 1449 | AUAUAUUGUAGUAGAUGUU |
| 426 | AS | 1449 | AACAUCUACUACAAUAUAU |
| 427 | S | 1484 | ACUAAACUUGCUGCUUAAU |
| 428 | AS | 1484 | AUUAAGCAGCAAGUUUAGU |
| 429 | S | 1493 | GCUGCUUAAUGAUUUGCUC |

TABLE 2-continued

Human CD274/PD-L1 Single Strands and Duplex Sequences

| Seq ID No. | strand ID (S = sense; AS = antisense) | Position of 5' base on transcript NM_014143.2 (SEQ ID NO: 869) | Sequence (5' to 3') |
|---|---|---|---|
| 430 | AS | 1493 | GAGCAAAUCAUUAAGCAGC |
| 431 | S | 1498 | UUAAUGAUUUGCUCACAUC |
| 432 | AS | 1498 | GAUGUGAGCAAAUCAUUAA |
| 433 | S | 1511 | CACAUCUAGUAAAACAUGG |
| 434 | AS | 1511 | CCAUGUUUUACUAGAUGUG |
| 435 | S | 1516 | CUAGUAAAACAUGGAGUAU |
| 436 | AS | 1516 | AUACUCCAUGUUUUACUAG |

TABLE 3

Human CD274/PD-L1 Modified Single Strands and Duplex Sequences

| SEQ ID NO: | Duplex | Single strand | Sequence | Oligo design name |
|---|---|---|---|---|
| 437 | AD-22303.1 | A-43007.1 | cGAcuAcAAGcGAAuuAcudTsdT | NM_014143.2_415-433s |
| 438 | | A-43008.1 | AGuAAuUCGCUUGuAGUCGdTsdT | NM_014143.2_415-433s |
| 439 | AD-22304.1 | A-43009.1 | uccuAGGAAGAcGGGuuGAdTsdT | NM_014143.2_1236-1254s |
| 440 | | A-43010.1 | UcAACCCGUCUUCCuAGGAdTsdT | NM_014143.2_1236-1254s |
| 441 | AD-22305.1 | A-43011.1 | GuGccGAcuAcAAGcGAAudTsdT | NM_014143.2_411-429s |
| 442 | | A-43012.1 | AUUCGCUUGuAGUCGGcACdTsdT | NM_014143.2_411-429s |
| 443 | AD-22306.1 | A-43013.1 | ccGAcuAcAAGcGAAuuAcdTsdT | NM_014143.2_414-432s |
| 444 | | A-43014.1 | GuAAuUCGCUUGuAGUCGGdTsdT | NM_014143.2_414-432s |
| 445 | AD-22307.1 | A-43015.1 | GccGAcuAcAAGcGAAuuAdTsdT | NM_014143.2_413-431s |
| 446 | | A-43016.1 | uAAuUCGCUUGuAGUCGGcdTsdT | NM_014143.2_413-431s |
| 447 | AD-22308.1 | A-43017.1 | GuuuAGGGGuucAucGGGGdTsdT | NM_014143.2_973-991s |
| 448 | | A-43018.1 | CCCCGAUGAACCCuAAACdTsdT | NM_014143.2_973-991s |
| 449 | AD-22309.1 | A-43019.1 | GAuGuuAcAAuuuuGucGcdTsdT | NM_014143.2_1462-1480s |
| 450 | | A-43020.1 | GCGAcAAAAUUGuAAcAUCdTsdT | NM_014143.2_1462-1480s |
| 451 | AD-22310.1 | A-43021.1 | GcAuuuAcuGucAcGGuucdTsdT | NM_014143.2_104-122s |
| 452 | | A-43022.1 | GAACCGUGAcAGuAAAUGCdTsdT | NM_014143.2_104-122s |
| 453 | AD-22311.1 | A-43023.1 | GAGccAucuuAuuAuGccudTsdT | NM_014143.2_786-804s |
| 454 | | A-43024.1 | AGGcAuAAuAAGAUGGCUCdTsdT | NM_014143.2_786-804s |
| 455 | AD-22312.1 | A-43025.1 | AGucucAGuGuuGGAAcGGdTsdT | NM_014143.2_1338-1356s |
| 456 | | A-43026.1 | CCGUUCcAAcACUGAGACUdTsdT | NM_014143.2_1338-1356s |
| 457 | AD-22313.1 | A-43027.1 | cuuuuAGGAGAuuAGAuccdTsdT | NM_014143.2_681-699s |
| 458 | | A-43028.1 | GGAUCuAAUCUCCuAAAAGdTsdT | NM_014143.2_681-699s |
| 459 | AD-22314.1 | A-43029.1 | AuGGAAccuGGcGAAAGcAdTsdT | NM_014143.2_1067-1085s |
| 460 | | A-43030.1 | UGCUUUCGCcAGGUUCcAUdTsdT | NM_014143.2_1067-1085s |
| 461 | AD-22315.1 | A-43031.1 | cuAccccAAGGccGAAGucdTsdT | NM_014143.2_529-547s |
| 462 | | A-43032.1 | GACUUCGGCCUUGGGGuAGdTsdT | NM_014143.2_529-547s |
| 463 | AD-22316.1 | A-43033.1 | uGGAAccuGGcGAAAGcAGdTsdT | NM_014143.2_1068-1086s |
| 464 | | A-43034.1 | CUGCUUUCGCcAGGUUCcAdTsdT | NM_014143.2_1068-1086s |
| 465 | AD-22317.1 | A-43035.1 | uAuGuGGuAGAGuAuGGuAdTsdT | NM_014143.2_134-152s |
| 466 | | A-43036.1 | uACcAuACUCUcAccAcAudTsdT | NM_014143.2_134-152s |
| 467 | AD-22318.1 | A-43037.1 | uGGucAucccAGAcuAccdTsdT | NM_014143.2_723-741s |
| 468 | | A-43038.1 | GGuAGUUCUGGGAUGACcAdTsdT | NM_014143.2_723-741s |
| 469 | AD-22319.1 | A-43039.1 | cAuuuAcuGucAcGGuuccdTsdT | NM_014143.2_105-123s |
| 470 | | A-43040.1 | GGAACCGUGAcAGuAAAUGdTsdT | NM_014143.2_105-123s |

TABLE 3-continued

Human CD274/PD-L1 Modified Single Strands and Duplex Sequences

| SEQ ID NO: | Duplex | Single strand | Sequence | Oligo design name |
|---|---|---|---|---|
| 471 | AD-22320.1 | A-43041.1 | GGAGccAucuuAuuAuGccdTsdT | NM_014143.2_785-803s |
| 472 | | A-43042.1 | GGcAuAAuAAGAUGGCUCCdTsdT | NM_014143.2_785-803s |
| 473 | AD-22321.1 | A-43043.1 | GAcuAcAAGcGAAuuAcuGdTsdT | NM_014143.2_416-434s |
| 474 | | A-43044.1 | cAGuAAUUCGCUUGuAGUCdTsdT | NM_014143.2_416-434s |
| 475 | AD-22322.1 | A-43045.1 | cAuAcAGcuGAAuuGGucAdTsdT | NM_014143.2_710-728s |
| 476 | | A-43046.1 | UGACcAAUUcAGCUGuAUGdTsdT | NM_014143.2_710-728s |
| 477 | AD-22323.1 | A-43047.1 | GcAcuAAuuGucuAuuGGGdTsdT | NM_014143.2_206-224s |
| 478 | | A-43048.1 | CCCAAuAGAcAAUuAGUGCdTsdT | NM_014143.2_206-224s |
| 479 | AD-22324.1 | A-43049.1 | uuuAGGGGuucAucGGGGcdTsdT | NM_014143.2_974-992s |
| 480 | | A-43050.1 | GCCCCGAUGAACCCCuAAAdTsdT | NM_014143.2_974-992s |
| 481 | AD-22325.1 | A-43051.1 | cucAAccuGuGGuuuAGGGdTsdT | NM_014143.2_962-980s |
| 482 | | A-43052.1 | CCCuAAAACcAcAGGUUGAGdTsdT | NM_014143.2_962-980s |
| 483 | AD-22326.1 | A-43053.1 | ccuAAuuuGAGGGucAGuudTsdT | NM_014143.2_1260-1278s |
| 484 | | A-43054.1 | AACUGACCCUcAAAUuAGGdTsdT | NM_014143.2_1260-1278s |
| 485 | AD-22327.1 | A-43055.1 | ucucAAccuGuGGuuuAGGdTsdT | NM_014143.2_961-979s |
| 486 | | A-43056.1 | CCuAAAACcAcAGGUUGAGAdTsdT | NM_014143.2_961-979s |
| 487 | AD-22328.1 | A-43057.1 | uuuAGGAGAuuAGAuccuGdTsdT | NM_014143.2_683-701s |
| 488 | | A-43058.1 | cAGGAUCuAAUCUCCuAAAdTsdT | NM_014143.2_683-701s |
| 489 | AD-22329.1 | A-43059.1 | ccAuuGcucAuccuAGGAAdTsdT | NM_014143.2_1226-1244s |
| 490 | | A-43060.1 | UUCCuAGGAUGAGcAAUGGdTsdT | NM_014143.2_1226-1244s |
| 491 | AD-22330.1 | A-43061.1 | cccAAGGAccuAuAuGuGGdTsdT | NM_014143.2_122-140s |
| 492 | | A-43062.1 | CcAcAuAuAGGUCCUUGGGdTsdT | NM_014143.2_122-140s |
| 493 | AD-22331.1 | A-43063.1 | GAcGGGuuGAGAAucccuAdTsdT | NM_014143.2_1245-1263s |
| 494 | | A-43064.1 | uAGGGAUUCUcAACCCGUCdTsdT | NM_014143.2_1245-1263s |
| 495 | AD-22332.1 | A-43065.1 | GcuGcAcuAAuuGucuAuudTsdT | NM_014143.2_203-221s |
| 496 | | A-43066.1 | AAuAGAcAAUuAGUGcAGCdTsdT | NM_014143.2_203-221s |
| 497 | AD-22333.1 | A-43067.1 | uuAcuGucAcGGuucccAAdTsdT | NM_014143.2_108-126s |
| 498 | | A-43068.1 | UUGGGAACCGUGAcAGuAAdTsdT | NM_014143.2_108-126s |
| 499 | AD-22334.1 | A-43069.1 | uuGGucAucccAGAAcuAcdTsdT | NM_014143.2_722-740s |
| 500 | | A-43070.1 | GuAGUUCUGGGAUGACcAAdTsdT | NM_014143.2_722-740s |
| 501 | AD-22335.1 | A-43071.1 | GuGGuGccGAcuAcAAGcGdTsdT | NM_014143.2_408-426s |
| 502 | | A-43072.1 | CGCUUGuAGUCGGcAccACdTsdT | NM_014143.2_408-426s |
| 503 | AD-22336.1 | A-43073.1 | ccGuGGGAuGcAGGcAAuGdTsdT | NM_014143.2_1020-1038s |
| 504 | | A-43074.1 | cAUUGCCUGcAUCCcACGGdTsdT | NM_014143.2_1020-1038s |
| 505 | AD-22337.1 | A-43075.1 | ccAucuuAuuAuGccuuGGdTsdT | NM_014143.2_789-807s |
| 506 | | A-43076.1 | CcAAGGcAuAAuAAGAUGGdTsdT | NM_014143.2_789-807s |
| 507 | AD-22338.1 | A-43077.1 | uGAAcGcAuuuAcuGucAcdTsdT | NM_014143.2_99-117s |
| 508 | | A-43078.1 | GUGAcAGuAAAUGCGUUcAdTsdT | NM_014143.2_99-117s |
| 509 | AD-22339.1 | A-43079.1 | GGuGuAGcAcuGAcAuucAdTsdT | NM_014143.2_806-824s |
| 510 | | A-43080.1 | UGAAUGUcAGUGCuAcACCdTsdT | NM_014143.2_806-824s |
| 511 | AD-22340.1 | A-43081.1 | cuGAAcGcAuuuAcuGucAdTsdT | NM_014143.2_98-116s |
| 512 | | A-43082.1 | UGAcAGuAAAUGCGUUcAGdTsdT | NM_014143.2_98-116s |
| 513 | AD-22341.1 | A-43083.1 | cAAGGAccuAuAuGuGGuAdTsdT | NM_014143.2_124-142s |
| 514 | | A-43084.1 | uACcAcAuAuAGGUCCUUGdTsdT | NM_014143.2_124-142s |
| 515 | AD-22342.1 | A-43085.1 | GAGAccuuGAuAcuuucAAdTsdT | NM_014143.2_1132-1150s |
| 516 | | A-43086.1 | UUGAAAGuAUcAAGGUCUCdTsdT | NM_014143.2_1132-1150s |
| 517 | AD-22343.1 | A-43087.1 | GGGcuGAGcGuGAcAAGAGdTsdT | NM_014143.2_989-1007s |
| 518 | | A-43088.1 | CUCUUGUcACGCUcAGCCCdTsdT | NM_014143.2_989-1007s |
| 519 | AD-22344.1 | A-43089.1 | uAuGGuGGuGccGAcuAcAdTsdT | NM_014143.2_404-422s |
| 520 | | A-43090.1 | UGuAGUCGGcACcACcAuAdTsdT | NM_014143.2_404-422s |

TABLE 3-continued

Human CD274/PD-L1 Modified Single Strands and Duplex Sequences

| SEQ ID NO: Duplex | Single strand | Sequence | Oligo design name |
|---|---|---|---|
| 521 AD-22345.1 | A-43091.1 | AAGGuucAGcAuAGuAGcudTsdT | NM_014143.2_275-293s |
| 522 | A-43092.1 | AGCuACuAUGCUGAACCUUdTsdT | NM_014143.2_275-293s |
| 523 AD-22346.1 | A-43093.1 | AuccuAGGAAGAcGGGuuGdTsdT | NM_014143.2_1235-1253s |
| 524 | A-43094.1 | cAACCCGUCUUCCuAGGAUdTsdT | NM_014143.2_1235-1253s |
| 525 AD-22347.1 | A-43095.1 | AuGuuAcAAuuuuGucGccdTsdT | NM_014143.2_1463-1481s |
| 526 | A-43096.1 | GGCGAcAAAAUUGuAAcAUdTsdT | NM_014143.2_1463-1481s |
| 527 AD-22348.1 | A-43097.1 | AuuuAcuGucAcGGuucccdTsdT | NM_014143.2_106-124s |
| 528 | A-43098.1 | GGGAACCGUGAcAGuAAAUdTsdT | NM_014143.2_106-124s |
| 529 AD-22349.1 | A-43099.1 | cGcAuuuAcuGucAcGGuudTsdT | NM_014143.2_103-121s |
| 530 | A-43100.1 | AACCGUGAcAGuAAAUGCGdTsdT | NM_014143.2_103-121s |
| 531 AD-22350.1 | A-43101.1 | AGGuucAGcAuAGuAGcudTsdT | NM_014143.2_276-294s |
| 532 | A-43102.1 | uAGCuACuAUGCUGAACCUdTsdT | NM_014143.2_276-294s |
| 533 AD-24151.1 | A-54818.1 | cAccAGccGcGcuucuGucdTsdT | NM_014143.2_11-29s |
| 534 | A-54819.1 | GAcAGAAGCGCGGCUGGUGdTsdT | NM_014143.2_11-29s |
| 535 AD-24152.1 | A-54820.1 | cGcGcuucuGuccGccuGcdTsdT | NM_014143.2_18-36s |
| 536 | A-54821.1 | GcAGGCGGAcAGAAGCGCGdTsdT | NM_014143.2_18-36s |
| 537 AD-24153.1 | A-54822.1 | AAGAuGAGGAuAuuuGcuGdTsdT | NM_014143.2_50-68s |
| 538 | A-54823.1 | cAGcAAAuAUCCUcAUCUUdTsdT | NM_014143.2_50-68s |
| 539 AD-24154.1 | A-54824.1 | cuuuAuAuucAuGAccuAcdTsdT | NM_014143.2_70-88s |
| 540 | A-54825.1 | GuAGGUcAUGAAuAuAAAGdTsdT | NM_014143.2_70-88s |
| 541 AD-24155.1 | A-54826.1 | AuucAuGAccuAcuGGcAudTsdT | NM_014143.2_76-94s |
| 542 | A-54827.1 | AUGCcAGuAGGUcAUGAAUdTsdT | NM_014143.2_76-94s |
| 543 AD-24156.1 | A-54828.1 | ucAuGAccuAcuGGcAuuudTsdT | NM_014143.2_78-96s |
| 544 | A-54829.1 | AAAUGCcAGuAGGUcAUGAdTsdT | NM_014143.2_78-96s |
| 545 AD-24157.1 | A-54830.1 | uAcuGGcAuuuGcuGAAcGdTsdT | NM_014143.2_86-104s |
| 546 | A-54831.1 | CGUUcAGcAAAUGCcAGuAdTsdT | NM_014143.2_86-104s |
| 547 AD-24158.1 | A-54832.1 | cuGGcAuuuGcuGAAcGcAdTsdT | NM_014143.2_88-106s |
| 548 | A-54833.1 | UGCGUUcAGcAAAUGCcAGdTsdT | NM_014143.2_88-106s |
| 549 AD-24159.1 | A-54834.1 | AuuuGcuGAAcGcAuuuAcdTsdT | NM_014143.2_93-111s |
| 550 | A-54835.1 | GuAAAUGCGUUcAGcAAAUdTsdT | NM_014143.2_93-111s |
| 551 AD-24160.1 | A-54836.1 | uuuGcuGAAcGcAuuuAcudTsdT | NM_014143.2_94-112s |
| 552 | A-54837.1 | AGuAAAUGCGUUcAGcAAAdTsdT | NM_014143.2_94-112s |
| 553 AD-24161.1 | A-54838.1 | GcuGAAcGcAuuuAcuGucdTsdT | NM_014143.2_97-115s |
| 554 | A-54839.1 | GAcAGuAAAUGCGUUcAGCdTsdT | NM_014143.2_97-115s |
| 555 AD-24162.1 | A-54840.1 | uuuAcuGucAcGGuucccAdTsdT | NM_014143.2_107-125s |
| 556 | A-54841.1 | UGGGAACCGUGAcAGuAAAdTsdT | NM_014143.2_107-125s |
| 557 AD-24163.1 | A-54842.1 | AcGGuucccAAGGAccuAudTsdT | NM_014143.2_116-134s |
| 558 | A-54843.1 | AuAGGUCCUUGGGAACCGUdTsdT | NM_014143.2_116-134s |
| 559 AD-24164.1 | A-54844.1 | cGGuucccAAGGAccuAudTsdT | NM_014143.2_117-135s |
| 560 | A-54845.1 | uAuAGGUCCUUGGGAACCGdTsdT | NM_014143.2_117-135s |
| 561 AD-24165.1 | A-54846.1 | GGuucccAAGGAccuAuAudTsdT | NM_014143.2_118-136s |
| 562 | A-54847.1 | AuAuAGGUCCUUGGGAACCdTsdT | NM_014143.2_118-136s |
| 563 AD-24166.1 | A-54848.1 | GuucccAAGGAccuAuAuGdTsdT | NM_014143.2_119-137s |
| 564 | A-54849.1 | cAuAuAGGUCCUUGGGAACdTsdT | NM_014143.2_119-137s |
| 565 AD-24167.1 | A-54850.1 | GAccuAuAuGuGGuAGAGudTsdT | NM_014143.2_128-146s |
| 566 | A-54851.1 | ACUCuACcAcAuAuAGGUCdTsdT | NM_014143.2_128-146s |
| 567 AD-24168.1 | A-54852.1 | uGGuAGAGuAuGGuAGcAAdTsdT | NM_014143.2_138-156s |
| 568 | A-54853.1 | UUGCuACcAuACUCuACcAdTsdT | NM_014143.2_138-156s |

TABLE 3-continued

Human CD274/PD-L1 Modified Single Strands and Duplex Sequences

| SEQ ID NO: Duplex | Single strand | Sequence | Oligo design name |
|---|---|---|---|
| 569 AD-24169.1 | A-54854.1 | GuAuGGuAGcAAuAuGAcAAdTsdT | NM_014143.2_145-163s |
| 570 | A-54855.1 | UGUcAuAUUGCuACcAuACdTsdT | NM_014143.2_145-163s |
| 571 AD-24170.1 | A-54856.1 | uGGuAGcAAuAuGAcAAuudTsdT | NM_014143.2_148-166s |
| 572 | A-54857.1 | AAUUGUcAuAUUGCuACcAdTsdT | NM_014143.2_148-166s |
| 573 AD-24171.1 | A-54858.1 | GGuAGcAAuAuGAcAAuuGdTsdT | NM_014143.2_149-167s |
| 574 | A-54859.1 | cAAUUGUcAuAUUGCuACCdTsdT | NM_014143.2_149-167s |
| 575 AD-24172.1 | A-54860.1 | AGcAAuAuGAcAAuuGAAudTsdT | NM_014143.2_152-170s |
| 576 | A-54861.1 | AUUcAAUUGUcAuAUUGCUdTsdT | NM_014143.2_152-170s |
| 577 AD-24173.1 | A-54862.1 | cAAuAuGAcAAuuGAAuGcdTsdT | NM_014143.2_154-172s |
| 578 | A-54863.1 | GcAUUcAAUUGUcAuAUUGdTsdT | NM_014143.2_154-172s |
| 579 AD-24174.1 | A-54864.1 | AAuGAcAAuuGAAuGcAAdTsdT | NM_014143.2_155-173s |
| 580 | A-54865.1 | UGcAUUcAAUUGUcAuAUUdTsdT | NM_014143.2_155-173s |
| 581 AD-24175.1 | A-54866.1 | AuAuGAcAAuuGAAuGcAAdTsdT | NM_014143.2_156-174s |
| 582 | A-54867.1 | UUGcAUUcAAUUGUcAuAUdTsdT | NM_014143.2_156-174s |
| 583 AD-24176.1 | A-54868.1 | cAAuuGAAuGcAAAuucccdTsdT | NM_014143.2_162-180s |
| 584 | A-54869.1 | GGGAAUUUGcAUUcAAUUGdTsdT | NM_014143.2_162-180s |
| 585 AD-24177.1 | A-54870.1 | uGAAuGcAAAuucccAGudTsdT | NM_014143.2_166-184s |
| 586 | A-54871.1 | uACUGGGAAUUUGcAUUcAdTsdT | NM_014143.2_166-184s |
| 587 AD-24178.1 | A-54872.1 | AAuGcAAAuucccAGuAGAdTsdT | NM_014143.2_168-186s |
| 588 | A-54873.1 | UCuACUGGGAAUUUGcAUUdTsdT | NM_014143.2_168-186s |
| 589 AD-24179.1 | A-54874.1 | AAAAcAAuuAGAccuGGcudTsdT | NM_014143.2_187-205s |
| 590 | A-54875.1 | AGCcAGGUCuAAUUGUUUUdTsdT | NM_014143.2_187-205s |
| 591 AD-24180.1 | A-54876.1 | AAAcAAuuAGAccuGGcuGdTsdT | NM_014143.2_188-206s |
| 592 | A-54877.1 | cAGCcAGGUCuAAUUGUUUdTsdT | NM_014143.2_188-206s |
| 593 AD-24181.1 | A-54878.1 | GGcuGcAcuAAuuGucuAudTsdT | NM_014143.2_202-220s |
| 594 | A-54879.1 | AuAGAcAAUuAGUGcAGCCdTsdT | NM_014143.2_202-220s |
| 595 AD-24182.1 | A-54880.1 | uGcAcuAAuuGucuAuuGGdTsdT | NM_014143.2_205-223s |
| 596 | A-54881.1 | CcAAuAGAcAAUuAGUGcAdTsdT | NM_014143.2_205-223s |
| 597 AD-24183.1 | A-54882.1 | uAuuGGGAAAuGGAGGAuAdTsdT | NM_014143.2_218-236s |
| 598 | A-54883.1 | uAUCCUCcAUUUCCcAAuAdTsdT | NM_014143.2_218-236s |
| 599 AD-24184.1 | A-54884.1 | cAAuuuGuGcAuGGAGAGGdTsdT | NM_014143.2_248-266s |
| 600 | A-54885.1 | CCUCUCcAUGcAcAAAUUGdTsdT | NM_014143.2_248-266s |
| 601 AD-24185.1 | A-54886.1 | ccuGAAGGuucAGcAuAGudTsdT | NM_014143.2_271-289s |
| 602 | A-54887.1 | ACuAUGCUGAACCUUcAGGdTsdT | NM_014143.2_271-289s |
| 603 AD-24186.1 | A-54888.1 | uGAAGGuucAGcAuAGuAGdTsdT | NM_014143.2_273-291s |
| 604 | A-54889.1 | CuACuAUGCUGAACCUUcAdTsdT | NM_014143.2_273-291s |
| 605 AD-24187.1 | A-54890.1 | GGuucAGcAuAGuAGcuAcdTsdT | NM_014143.2_277-295s |
| 606 | A-54891.1 | GuAGCuACuAUGCUGAACCdTsdT | NM_014143.2_277-295s |
| 607 AD-24188.1 | A-54892.1 | GuucAGcAuAGuAGcuAcdTsdT | NM_014143.2_278-296s |
| 608 | A-54893.1 | UGuAGCuACuAUGCUGAACdTsdT | NM_014143.2_278-296s |
| 609 AD-24189.1 | A-54894.1 | uucAGcAuAGuAGcuAcAGdTsdT | NM_014143.2_279-297s |
| 610 | A-54895.1 | CUGuAGCuACuAUGCUGAAdTsdT | NM_014143.2_279-297s |
| 611 AD-24190.1 | A-54896.1 | cAuAGuAGcuAcAGAcAGAdTsdT | NM_014143.2_284-302s |
| 612 | A-54897.1 | UCUGUCUGuAGCuACuAUGdTsdT | NM_014143.2_284-302s |
| 613 AD-24191.1 | A-54898.1 | AuAGuAGcuAcAGAcAGAGdTsdT | NM_014143.2_285-303s |
| 614 | A-54899.1 | CUCUGUCUGuAGCuACuAUdTsdT | NM_014143.2_285-303s |
| 615 AD-24192.1 | A-54900.1 | cuAcAGAcAGAGGGcccGGdTsdT | NM_014143.2_292-310s |
| 616 | A-54901.1 | CCGGGCCCUCUGUCUGuAGdTsdT | NM_014143.2_292-310s |
| 617 AD-24193.1 | A-54902.1 | GcuGcAcuucAGAucAcAGdTsdT | NM_014143.2_341-359s |
| 618 | A-54903.1 | CUGUGAUCUGAAGUGcAGCdTsdT | NM_014143.2_341-359s |

TABLE 3-continued

Human CD274/PD-L1 Modified Single Strands and Duplex Sequences

| SEQ ID NO: Duplex | Single strand | Sequence | Oligo design name |
|---|---|---|---|
| 619 AD-24194.1 | A-54904.1 | cuGcAcuucAGAucAcAGAdTsdT | NM_014143.2_342-360s |
| 620 | A-54905.1 | UCUGUGAUCUGAAGUGcAGdTsdT | NM_014143.2_342-360s |
| 621 AD-24195.1 | A-54906.1 | uGcAcuucAGAucAcAGAudTsdT | NM_014143.2_343-361s |
| 622 | A-54907.1 | AUCUGUGAUCUGAAGUGcAdTsdT | NM_014143.2_343-361s |
| 623 AD-24196.1 | A-54908.1 | GcAcuucAGAucAcAGAuGdTsdT | NM_014143.2_344-362s |
| 624 | A-54909.1 | cAUCUGUGAUCUGAAGUGCdTsdT | NM_014143.2_344-362s |
| 625 AD-24197.1 | A-54910.1 | AAAuuGcAGGAuGcAGGGGdTsdT | NM_014143.2_365-383s |
| 626 | A-54911.1 | CCCCUGcAUCCUGcAAUUUdTsdT | NM_014143.2_365-383s |
| 627 AD-24198.1 | A-54912.1 | cAGGAuGcAGGGGuGuAccdTsdT | NM_014143.2_371-389s |
| 628 | A-54913.1 | GGuAcACCCCUGcAUCCUGdTsdT | NM_014143.2_371-389s |
| 629 AD-24199.1 | A-54914.1 | GGAuGcAGGGGuGuAccGcdTsdT | NM_014143.2_373-391s |
| 630 | A-54915.1 | GCGGuAcACCCCUGcAUCCdTsdT | NM_014143.2_373-391s |
| 631 AD-24200.1 | A-54916.1 | GuAccGcuGcAuGAucAGcdTsdT | NM_014143.2_385-403s |
| 632 | A-54917.1 | GCUGAUcAUGcAGCGGuACdTsdT | NM_014143.2_385-403s |
| 633 AD-24201.1 | A-54918.1 | AccGcuGcAuGAucAGcuAdTsdT | NM_014143.2_387-405s |
| 634 | A-54919.1 | uAGCUGAUcAUGcAGCGGUdTsdT | NM_014143.2_387-405s |
| 635 AD-24202.1 | A-54920.1 | AuGAucAGcuAuGGuGGuGdTsdT | NM_014143.2_395-413s |
| 636 | A-54921.1 | cACcACcAuAGCUGAUcAUdTsdT | NM_014143.2_395-413s |
| 637 AD-24203.1 | A-54922.1 | GcuAuGGuGGuGccGAcuAdTsdT | NM_014143.2_402-420s |
| 638 | A-54923.1 | uAGUCGGcACcACcAuAGCdTsdT | NM_014143.2_402-420s |
| 639 AD-24204.1 | A-54924.1 | uGccGAcuAcAAGcGAAuudTsdT | NM_014143.2_412-430s |
| 640 | A-54925.1 | AAUUCGCUUGuAGUCGGcAdTsdT | NM_014143.2_412-430s |
| 641 AD-24205.1 | A-54926.1 | AGcGAAuuAcuGuGAAAGudTsdT | NM_014143.2_423-441s |
| 642 | A-54927.1 | ACUUUcAcAGuAAUUCGCUdTsdT | NM_014143.2_423-441s |
| 643 AD-24206.1 | A-54928.1 | GcGAAuuAcuGuGAAAGucdTsdT | NM_014143.2_424-442s |
| 644 | A-54929.1 | GACUUUcAcAGuAAUUCGCdTsdT | NM_014143.2_424-442s |
| 645 AD-24207.1 | A-54930.1 | cGAAuuAcuGuGAAAGucAdTsdT | NM_014143.2_425-443s |
| 646 | A-54931.1 | UGACUUUcAcAGuAAUUCGdTsdT | NM_014143.2_425-443s |
| 647 AD-24208.1 | A-54932.1 | AuuAcuGuGAAAGucAAuGdTsdT | NM_014143.2_428-446s |
| 648 | A-54933.1 | cAUUGACUUUcAcAGuAAUdTsdT | NM_014143.2_428-446s |
| 649 AD-24209.1 | A-54934.1 | uAcuGuGAAAGucAAuGccdTsdT | NM_014143.2_430-448s |
| 650 | A-54935.1 | GGcAUUGACUUUcAcAGuAdTsdT | NM_014143.2_430-448s |
| 651 AD-24210.1 | A-54936.1 | AAAGucAAuGccccAuAcAdTsdT | NM_014143.2_437-455s |
| 652 | A-54937.1 | UGuAUGGGGcAUUGACUUUdTsdT | NM_014143.2_437-455s |
| 653 AD-24211.1 | A-54938.1 | GucAAuGccccAuAcAAcAdTsdT | NM_014143.2_440-458s |
| 654 | A-54939.1 | UGUUGuAUGGGGcAUUGACdTsdT | NM_014143.2_440-458s |
| 655 AD-24212.1 | A-54940.1 | AAuuuuGGuuGuGGAuccAdTsdT | NM_014143.2_472-490s |
| 656 | A-54941.1 | UGGAUCcAcAACcAAAAUUdTsdT | NM_014143.2_472-490s |
| 657 AD-24213.1 | A-54942.1 | AuuuuGGuuGuGGAuccAGdTsdT | NM_014143.2_473-491s |
| 658 | A-54943.1 | CUGGAUCcAcAACcAAAAUdTsdT | NM_014143.2_473-491s |
| 659 AD-24214.1 | A-54944.1 | AGucAccucuGAAcAuGAAdTsdT | NM_014143.2_490-508s |
| 660 | A-54945.1 | UUcAUGUUcAGAGGUGACUdTsdT | NM_014143.2_490-508s |
| 661 AD-24215.1 | A-54946.1 | AccucuGAAcAuGAAcuGAdTsdT | NM_014143.2_494-512s |
| 662 | A-54947.1 | UcAGUUcAUGUUcAGAGGUdTsdT | NM_014143.2_494-512s |
| 663 AD-24216.1 | A-54948.1 | ccucuGAAcAuGAAcuGAcdTsdT | NM_014143.2_495-513s |
| 664 | A-54949.1 | GUcAGUUcAUGUUcAGAGGdTsdT | NM_014143.2_495-513s |
| 665 AD-24217.1 | A-54950.1 | uGAAcAuGAAcuGAcAuGudTsdT | NM_014143.2_499-517s |
| 666 | A-54951.1 | AcAUGUcAGUUcAUGUUcAdTsdT | NM_014143.2_499-517s |

TABLE 3-continued

Human CD274/PD-L1 Modified Single Strands and Duplex Sequences

| SEQ ID NO: Duplex | Single strand | Sequence | Oligo design name |
|---|---|---|---|
| 667 AD-24218.1 | A-54952.1 | AcAuGAAcuGAcAuGucAGdTsdT | NM_014143.2_502-520s |
| 668 | A-54953.1 | CUGAcAUGUcAGUUcAUGUdTsdT | NM_014143.2_502-520s |
| 669 AD-24219.1 | A-54954.1 | cAuGAAcuGAcAuGucAGGdTsdT | NM_014143.2_503-521s |
| 670 | A-54955.1 | CCUGAcAUGUcAGUUcAUGdTsdT | NM_014143.2_503-521s |
| 671 AD-24220.1 | A-54956.1 | uGAAcuGAcAuGucAGGcudTsdT | NM_014143.2_505-523s |
| 672 | A-54957.1 | AGCCUGAcAUGUcAGUUcAdTsdT | NM_014143.2_505-523s |
| 673 AD-24221.1 | A-54958.1 | GAAcuGAcAuGucAGGcuGdTsdT | NM_014143.2_506-524s |
| 674 | A-54959.1 | cAGCCUGAcAUGUcAGUUCdTsdT | NM_014143.2_506-524s |
| 675 AD-24222.1 | A-54960.1 | GAcAuGucAGGcuGAGGGcdTsdT | NM_014143.2_511-529s |
| 676 | A-54961.1 | GCCCUcAGCCUGAcAUGUCdTsdT | NM_014143.2_511-529s |
| 677 AD-24223.1 | A-54962.1 | uGucAGGcuGAGGGcuAccdTsdT | NM_014143.2_515-533s |
| 678 | A-54963.1 | GGuAGCCCUcAGCCUGAcAdTsdT | NM_014143.2_515-533s |
| 679 AD-24224.1 | A-54964.1 | uAccccAAGGccGAAGucAdTsdT | NM_014143.2_530-548s |
| 680 | A-54965.1 | UGACUUCGGCCUUGGGGuAdTsdT | NM_014143.2_530-548s |
| 681 AD-24225.1 | A-54966.1 | AAGGccGAAGucAucuGGAdTsdT | NM_014143.2_536-554s |
| 682 | A-54967.1 | UCcAGAUGACUUCGGCCUUdTsdT | NM_014143.2_536-554s |
| 683 AD-24226.1 | A-54968.1 | cGAAGucAucuGGAcAAGcdTsdT | NM_014143.2_541-559s |
| 684 | A-54969.1 | GCUUGUCcAGAUGACUUCGdTsdT | NM_014143.2_541-559s |
| 685 AD-24227.1 | A-54970.1 | cAucuGGAcAAGcAGuGAcdTsdT | NM_014143.2_547-565s |
| 686 | A-54971.1 | GUcACUGCUUGUCcAGAUGdTsdT | NM_014143.2_547-565s |
| 687 AD-24228.1 | A-54972.1 | AGcAGuGAccAucAAGuccdTsdT | NM_014143.2_557-575s |
| 688 | A-54973.1 | GGACUUGAUGGUcACUGCUdTsdT | NM_014143.2_557-575s |
| 689 AD-24229.1 | A-54974.1 | ucAAGuccuGAGuGGuAAGdTsdT | NM_014143.2_568-586s |
| 690 | A-54975.1 | CUuACcACUcAGGACUUGAdTsdT | NM_014143.2_568-586s |
| 691 AD-24230.1 | A-54976.1 | GAAucAAcAcAAcAcuAAdTsdT | NM_014143.2_645-663s |
| 692 | A-54977.1 | UuAGUUGUUGUGUUGAUUCdTsdT | NM_014143.2_645-663s |
| 693 AD-24231.1 | A-54978.1 | AAucAAcAcAAcAAcuAAudTsdT | NM_014143.2_646-664s |
| 694 | A-54979.1 | AUuAGUUGUUGUGUUGAUUdTsdT | NM_014143.2_646-664s |
| 695 AD-24232.1 | A-54980.1 | uucuAcuGcAcuuuuAGGAdTsdT | NM_014143.2_671-689s |
| 696 | A-54981.1 | UCCuAAAAGUGCAGuAGAAdTsdT | NM_014143.2_671-689s |
| 697 AD-24233.1 | A-54982.1 | GcAcuuuuAGGAGAuuAGAdTsdT | NM_014143.2_678-696s |
| 698 | A-54983.1 | UCuAAUCUCCuAAAAGUGCdTsdT | NM_014143.2_678-696s |
| 699 AD-24234.1 | A-54984.1 | uuuuAGGAGAuuAGAuccudTsdT | NM_014143.2_682-700s |
| 700 | A-54985.1 | AGGAUCuAAUCUCCuAAAAdTsdT | NM_014143.2_682-700s |
| 701 AD-24235.1 | A-54986.1 | uuAGGAGAuuAGAuccuGAdTsdT | NM_014143.2_684-702s |
| 702 | A-54987.1 | UcAGGAUCuAAUCUCCuAAdTsdT | NM_014143.2_684-702s |
| 703 AD-24236.1 | A-54988.1 | uAGGAGAuuAGAuccuGAGdTsdT | NM_014143.2_685-703s |
| 704 | A-54989.1 | CUcAGGAUCuAAUCUCCuAdTsdT | NM_014143.2_685-703s |
| 705 AD-24237.1 | A-54990.1 | AGGAGAuuAGAuccuGAGGdTsdT | NM_014143.2_686-704s |
| 706 | A-54991.1 | CCUcAGGAUCuAAUCUCCUdTsdT | NM_014143.2_686-704s |
| 707 AD-24238.1 | A-54992.1 | GGAGAuuAGAuccuGAGGAdTsdT | NM_014143.2_687-705s |
| 708 | A-54993.1 | UCCUcAGGAUCuAAUCUCCdTsdT | NM_014143.2_687-705s |
| 709 AD-24239.1 | A-54994.1 | AAccAuAcAGcuGAAuuGdTsdT | NM_014143.2_706-724s |
| 710 | A-54995.1 | cAAUUcAGCUGuAUGGUUdTsdT | NM_014143.2_706-724s |
| 711 AD-24240.1 | A-54996.1 | AAccAuAcAGcuGAAuuGGdTsdT | NM_014143.2_707-725s |
| 712 | A-54997.1 | CcAAUUcAGCUGuAUGGUUdTsdT | NM_014143.2_707-725s |
| 713 AD-24241.1 | A-54998.1 | ccAuAcAGcuGAAuuGucAdTsdT | NM_014143.2_709-727s |
| 714 | A-54999.1 | GACcAAUUcAGCUGuAUGGdTsdT | NM_014143.2_709-727s |
| 715 AD-24242.1 | A-55000.1 | AuAcAGcuGAAuuGGucAudTsdT | NM_014143.2_711-729s |
| 716 | A-55001.1 | AUGACcAAUUcAGCUGuAUdTsdT | NM_014143.2_711-729s |

TABLE 3-continued

Human CD274/PD-L1 Modified Single Strands and Duplex Sequences

| SEQ ID NO: | Duplex | Single strand | Sequence | Oligo design name |
|---|---|---|---|---|
| 717 | AD-24243.1 | A-55002.1 | GcuGAAuuGGucAucccAGdTsdT | NM_014143.2_716-734s |
| 718 | | A-55003.1 | CUGGGAUGACcAAUUcAGCdTsdT | NM_014143.2_716-734s |
| 719 | AD-24244.1 | A-55004.1 | GGucAucccAGAAcuAccudTsdT | NM_014143.2_724-742s |
| 720 | | A-55005.1 | AGGuAGUUCUGGGAUGACCdTsdT | NM_014143.2_724-742s |
| 721 | AD-24245.1 | A-55006.1 | uGGcAcAuccuccAAAuGAdTsdT | NM_014143.2_744-762s |
| 722 | | A-55007.1 | UcAUUUGGAGGAUGUGCcAdTsdT | NM_014143.2_744-762s |
| 723 | AD-24455.1 | A-55008.1 | uGAAAGGAcucAcuuGGuAdTsdT | NM_014143.2_760-778s |
| 724 | | A-55009.1 | uACcAAGUGAGUCCUUUcAdTsdT | NM_014143.2_760-778s |
| 725 | AD-24456.1 | A-55010.1 | AGGAcucAcuuGGuAAuucdTsdT | NM_014143.2_764-782s |
| 726 | | A-55011.1 | GAAUuACcAAGUGAGUCCUdTsdT | NM_014143.2_764-782s |
| 727 | AD-24457.1 | A-55012.1 | GAcucAcuuGGuAAuucuGdTsdT | NM_014143.2_766-784s |
| 728 | | A-55013.1 | cAGAAUuACcAAGUGAGUCdTsdT | NM_014143.2_766-784s |
| 729 | AD-24458.1 | A-55014.1 | ucAcuuGGuAAuucuGGGAdTsdT | NM_014143.2_769-787s |
| 730 | | A-55015.1 | UCCcAGAAUuACcAAGUGAdTsdT | NM_014143.2_769-787s |
| 731 | AD-24459.1 | A-55016.1 | GGuAAuucuGGGAGccAucdTsdT | NM_014143.2_775-793s |
| 732 | | A-55017.1 | GAUGGCUCCcAGAAUuACCdTsdT | NM_014143.2_775-793s |
| 733 | AD-24460.1 | A-55018.1 | GuAAuucuGGGAGccAucudTsdT | NM_014143.2_776-794s |
| 734 | | A-55019.1 | AGAUGGCUCCcAGAAUuACdTsdT | NM_014143.2_776-794s |
| 735 | AD-24461.1 | A-55020.1 | ucuGGGAGccAucuuAuuAdTsdT | NM_014143.2_781-799s |
| 736 | | A-55021.1 | uAAuAAGAUGGCUCCcAGAdTsdT | NM_014143.2_781-799s |
| 737 | AD-24462.1 | A-55022.1 | cuGGGAGccAucuuAuuAudTsdT | NM_014143.2_782-800s |
| 738 | | A-55023.1 | AuAAuAAGAUGGCUCCcAGdTsdT | NM_014143.2_782-800s |
| 739 | AD-24463.1 | A-55024.1 | uGGGAGccAucuuAuuAuGdTsdT | NM_014143.2_783-801s |
| 740 | | A-55025.1 | cAuAAuAAGAUGGCUCCcAdTsdT | NM_014143.2_783-801s |
| 741 | AD-24464.1 | A-55026.1 | GGGAGccAucuuAuuAuGcdTsdT | NM_014143.2_784-802s |
| 742 | | A-55027.1 | GcAuAAuAAGAUGGCUCCCdTsdT | NM_014143.2_784-802s |
| 743 | AD-24465.1 | A-55028.1 | AGccAucuuAuuAuGccuudTsdT | NM_014143.2_787-805s |
| 744 | | A-55029.1 | AAGGcAuAAuAAGAUGGCUdTsdT | NM_014143.2_787-805s |
| 745 | AD-24466.1 | A-55030.1 | AucuuAuuAuGccuuGGuGdTsdT | NM_014143.2_791-809s |
| 746 | | A-55031.1 | cACcAAGGcAuAAuAAGAUdTsdT | NM_014143.2_791-809s |
| 747 | AD-24467.1 | A-55032.1 | uAuuAuGccuuGGuGuAGcdTsdT | NM_014143.2_795-813s |
| 748 | | A-55033.1 | GCuAcACcAAGGcAuAAuAdTsdT | NM_014143.2_795-813s |
| 749 | AD-24468.1 | A-55034.1 | AuuAuGccuuGGuGuAGcAdTsdT | NM_014143.2_796-814s |
| 750 | | A-55035.1 | UGCuAcACcAAGGcAuAAUdTsdT | NM_014143.2_796-814s |
| 751 | AD-24469.1 | A-55036.1 | uGccuuGGuGuAGcAcuGAdTsdT | NM_014143.2_800-818s |
| 752 | | A-55037.1 | UcAGUGCuAcACcAAGGcAdTsdT | NM_014143.2_800-818s |
| 753 | AD-24470.1 | A-55038.1 | uGGuGuAGcAcuGAcAuucdTsdT | NM_014143.2_805-823s |
| 754 | | A-55039.1 | GAAUGUcAGUGCuAcACcAdTsdT | NM_014143.2_805-823s |
| 755 | AD-24471.1 | A-55040.1 | GuAGcAcuGAcAuucAucudTsdT | NM_014143.2_809-827s |
| 756 | | A-55041.1 | AGAUGAAUGUcAGUGCuACdTsdT | NM_014143.2_809-827s |
| 757 | AD-24472.1 | A-55042.1 | cuGAcAuucAucuuccGuudTsdT | NM_014143.2_815-833s |
| 758 | | A-55043.1 | AACGGAAGAUGAAUGUcAGdTsdT | NM_014143.2_815-833s |
| 759 | AD-24473.1 | A-55044.1 | AGGGAGAAuGAuGGAuGuGdTsdT | NM_014143.2_841-859s |
| 760 | | A-55045.1 | cAcAUCcAUcAUUCUCCCUdTsdT | NM_014143.2_841-859s |
| 761 | AD-24474.1 | A-55046.1 | uGGcAuccAAGAuAcAAAcdTsdT | NM_014143.2_868-886s |
| 762 | | A-55047.1 | GUUUGuAUCUUGGAUGCcAdTsdT | NM_014143.2_868-886s |
| 763 | AD-24475.1 | A-55048.1 | GGcAuccAAGAuAcAAAcudTsdT | NM_014143.2_869-887s |
| 764 | | A-55049.1 | AGUUUGuAUCUUGGAUGCCdTsdT | NM_014143.2_869-887s |

TABLE 3-continued

Human CD274/PD-L1 Modified Single Strands and Duplex Sequences

| SEQ ID NO: Duplex | Single strand | Sequence | Oligo design name |
|---|---|---|---|
| 765 AD-24476.1 | A-55050.1 | GcAuccAAGAuAcAAAcucdTsdT | NM_014143.2_870-888s |
| 766 | A-55051.1 | GAGUUUGuAUCUUGGAUGCdTsdT | NM_014143.2_870-888s |
| 767 AD-24477.1 | A-55052.1 | cAAAGuGAuAcAcAuuuGGdTsdT | NM_014143.2_896-914s |
| 768 | A-55053.1 | CcAAAUGUGuAUcACUUUGdTsdT | NM_014143.2_896-914s |
| 769 AD-24478.1 | A-55054.1 | GuGAuAcAcAuuuGGAGGAdTsdT | NM_014143.2_900-918s |
| 770 | A-55055.1 | UCCUCcAAAUGUGuAUcACdTsdT | NM_014143.2_900-918s |
| 771 AD-24479.1 | A-55056.1 | AcAcAuuuGGAGGAGAcGudTsdT | NM_014143.2_905-923s |
| 772 | A-55057.1 | ACGUCUCCUCcAAAUGUGUdTsdT | NM_014143.2_905-923s |
| 773 AD-24480.1 | A-55058.1 | AcAuuuGGAGGAGAcGuAAdTsdT | NM_014143.2_907-925s |
| 774 | A-55059.1 | UuACGUCUCCUCcAAAUGUdTsdT | NM_014143.2_907-925s |
| 775 AD-24481.1 | A-55060.1 | cAuuuGGAGGAGAcGuAAudTsdT | NM_014143.2_908-926s |
| 776 | A-55061.1 | AUuACGUCUCCUCcAAAUGdTsdT | NM_014143.2_908-926s |
| 777 AD-24482.1 | A-55062.1 | GGAGGAGAcGuAAuccAGcdTsdT | NM_014143.2_913-931s |
| 778 | A-55063.1 | GCUGGAUuACGUCUCCUCCdTsdT | NM_014143.2_913-931s |
| 779 AD-24483.1 | A-55064.1 | AcGuAAuccAGcAuuGGAAdTsdT | NM_014143.2_920-938s |
| 780 | A-55065.1 | UUCcAAUGCUGGAUuACGUdTsdT | NM_014143.2_920-938s |
| 781 AD-24484.1 | A-55066.1 | AAccuGuGGuuuAGGGGuudTsdT | NM_014143.2_965-983s |
| 782 | A-55067.1 | AACCCCuAAACcAcAGGUUdTsdT | NM_014143.2_965-983s |
| 783 AD-24485.1 | A-55068.1 | ccuGuGGuuuAGGGGuucAdTsdT | NM_014143.2_967-985s |
| 784 | A-55069.1 | UGAACCCCuAAACcAcAGGdTsdT | NM_014143.2_967-985s |
| 785 AD-24486.1 | A-55070.1 | cuGuGGuuuAGGGGuucAudTsdT | NM_014143.2_968-986s |
| 786 | A-55071.1 | AUGAACCCCuAAACcAcAGdTsdT | NM_014143.2_968-986s |
| 787 AD-24487.1 | A-55072.1 | uGGuuuAGGGGuucAucGGdTsdT | NM_014143.2_971-989s |
| 788 | A-55073.1 | CCGAUGAACCCCuAAACcAdTsdT | NM_014143.2_971-989s |
| 789 AD-24488.1 | A-55074.1 | GGuuuAGGGGuucAucGGGdTsdT | NM_014143.2_972-990s |
| 790 | A-55075.1 | CCCGAUGAACCCCuAAACCdTsdT | NM_014143.2_972-990s |
| 791 AD-24489.1 | A-55078.1 | AGGcAAuGuGGGAcuuAAAdTsdT | NM_014143.2_1031-1049s |
| 792 | A-55079.1 | UUuAAGUCCcAcAUUGCCUdTsdT | NM_014143.2_1031-1049s |
| 793 AD-24490.1 | A-55080.1 | GGcAAuGuGGGAcuuAAAAdTsdT | NM_014143.2_1032-1050s |
| 794 | A-55081.1 | UUUuAAGUCCcAcAUUGCCdTsdT | NM_014143.2_1032-1050s |
| 795 AD-24491.1 | A-55082.1 | GcAAuGuGGGAcuuAAAAGdTsdT | NM_014143.2_1033-1051s |
| 796 | A-55083.1 | CUUUuAAGUCCcAcAUUGCdTsdT | NM_014143.2_1033-1051s |
| 797 AD-24492.1 | A-55084.1 | uGAAAAuGGAAccuGGcGAdTsdT | NM_014143.2_1062-1080s |
| 798 | A-55085.1 | UCGCcAGGUUCcAUUUUcAdTsdT | NM_014143.2_1062-1080s |
| 799 AD-24493.1 | A-55086.1 | AAAAuGGAAccuGGcGAAAdTsdT | NM_014143.2_1064-1082s |
| 800 | A-55087.1 | UUUCGCcAGGUUCcAUUUUdTsdT | NM_014143.2_1064-1082s |
| 801 AD-24494.1 | A-55088.1 | GAGGGAGAccuuGAuAcuudTsdT | NM_014143.2_1128-1146s |
| 802 | A-55089.1 | AAGuAUcAAGGUCUCCCUCdTsdT | NM_014143.2_1128-1146s |
| 803 AD-24495.1 | A-55090.1 | AGGGAGAccuuGAuAcuuudTsdT | NM_014143.2_1129-1147s |
| 804 | A-55091.1 | AAAGuAUcAAGGUCUCCCUdTsdT | NM_014143.2_1129-1147s |
| 805 AD-24496.1 | A-55092.1 | AGAccuuGAuAcuuucAAAdTsdT | NM_014143.2_1133-1151s |
| 806 | A-55093.1 | UUUGAAAGuAUcAAGGUCUdTsdT | NM_014143.2_1133-1151s |
| 807 AD-24497.1 | A-55094.1 | uuGAuAcuuucAAAuGccudTsdT | NM_014143.2_1138-1156s |
| 808 | A-55095.1 | AGGcAUUUGAAAGuAUcAAdTsdT | NM_014143.2_1138-1156s |
| 809 AD-24498.1 | A-55096.1 | AAuGccuGAGGGGcucAucdTsdT | NM_014143.2_1150-1168s |
| 810 | A-55097.1 | GAUGAGCCCCUcAGGcAUUdTsdT | NM_014143.2_1150-1168s |
| 811 AD-24499.1 | A-55098.1 | uGccuGAGGGGcucAucGAdTsdT | NM_014143.2_1152-1170s |
| 812 | A-55099.1 | UCGAUGAGCCCCUcAGGcAdTsdT | NM_014143.2_1152-1170s |
| 813 AD-24500.1 | A-55100.1 | GGGcucAucGAcGccuGuGdTsdT | NM_014143.2_1160-1178s |
| 814 | A-55101.1 | cAcAGGCGUCGAUGAGCCCdTsdT | NM_014143.2_1160-1178s |

TABLE 3-continued

Human CD274/PD-L1 Modified Single Strands and Duplex Sequences

| SEQ ID NO: Duplex | Single strand | Sequence | Oligo design name |
|---|---|---|---|
| 815 AD-24501.1 | A-55102.1 | GGcucAucGAcGccuGuGAdTsdT | NM_014143.2_1161-1179s |
| 816 | A-55103.1 | UcAcAGGCGUCGAUGAGCCdTsdT | NM_014143.2_1161-1179s |
| 817 AD-24502.1 | A-55104.1 | AucGAcGccuGuGAcAGGGdTsdT | NM_014143.2_1166-1184s |
| 818 | A-55105.1 | CCCUGUcAcAGGCGUCGAUdTsdT | NM_014143.2_1166-1184s |
| 819 AD-24503.1 | A-55106.1 | AGGAGccuccAAGcAAAucdTsdT | NM_014143.2_1205-1223s |
| 820 | A-55107.1 | GAUUUGCUUGGAGGCUCCUdTsdT | NM_014143.2_1205-1223s |
| 821 AD-24504.1 | A-55108.1 | AuccAuuGcucAuccuAGGdTsdT | NM_014143.2_1224-1242s |
| 822 | A-55109.1 | CCuAGGAUGAGcAAUGGAUdTsdT | NM_014143.2_1224-1242s |
| 823 AD-24505.1 | A-55110.1 | ucAuccuAGGAAGAcGGGudTsdT | NM_014143.2_1233-1251s |
| 824 | A-55111.1 | ACCCGUCUUCCuAGGAUGAdTsdT | NM_014143.2_1233-1251s |
| 825 AD-24506.1 | A-55112.1 | cAuccuAGGAAGAcGGGuudTsdT | NM_014143.2_1234-1252s |
| 826 | A-55113.1 | AACCCGUCUUCCuAGGAUGAdTsdT | NM_014143.2_1234-1252s |
| 827 AD-24507.1 | A-55114.1 | cuAGGAAGAcGGGuuGAGAdTsdT | NM_014143.2_1238-1256s |
| 828 | A-55115.1 | UCUcAACCCGUCUUCCuAGdTsdT | NM_014143.2_1238-1256s |
| 829 AD-24508.1 | A-55116.1 | AcGGGuuGAGAAucccuAAdTsdT | NM_014143.2_1246-1264s |
| 830 | A-55117.1 | UuAGGGAUUCUcAACCCGUdTsdT | NM_014143.2_1246-1264s |
| 831 AD-24509.1 | A-55118.1 | AGAAucccuAAuuuGAGGGdTsdT | NM_014143.2_1254-1272s |
| 832 | A-55119.1 | CCCUcAAAUuAGGGAUUCUdTsdT | NM_014143.2_1254-1272s |
| 833 AD-24510.1 | A-55120.1 | AAucccuAAuuuGAGGGucdTsdT | NM_014143.2_1256-1274s |
| 834 | A-55121.1 | GACCCUcAAAUuAGGGAUUdTsdT | NM_014143.2_1256-1274s |
| 835 AD-24511.1 | A-55122.1 | cccuAAuuuGAGGGucAGudTsdT | NM_014143.2_1259-1277s |
| 836 | A-55123.1 | ACUGACCCUcAAAUuAGGGdTsdT | NM_014143.2_1259-1277s |
| 837 AD-24512.1 | A-55124.1 | cAcucAAuGccucAAuuuGdTsdT | NM_014143.2_1302-1320s |
| 838 | A-55125.1 | cAAAUUGAGGcAUUGAGUGdTsdT | NM_014143.2_1302-1320s |
| 839 AD-24513.1 | A-55126.1 | AcucAAuGccucAAuuuGudTsdT | NM_014143.2_1303-1321s |
| 840 | A-55127.1 | AcAAAUUGAGGcAUUGAGUdTsdT | NM_014143.2_1303-1321s |
| 841 AD-24514.1 | A-55128.1 | uucuGcAuGAcuGAGAGucdTsdT | NM_014143.2_1323-1341s |
| 842 | A-55129.1 | GACUCUcAGUcAUGcAGAAdTsdT | NM_014143.2_1323-1341s |
| 843 AD-24515.1 | A-55130.1 | ucuGcAuGAcuGAGAGucudTsdT | NM_014143.2_1324-1342s |
| 844 | A-55131.1 | AGACUCUcAGUcAUGcAGAdTsdT | NM_014143.2_1324-1342s |
| 845 AD-24516.1 | A-55132.1 | GcAuGAcuGAGAGucucAGdTsdT | NM_014143.2_1327-1345s |
| 846 | A-55133.1 | CUGAGACUCUcAGUcAUGCdTsdT | NM_014143.2_1327-1345s |
| 847 AD-24517.1 | A-55134.1 | GAcuGAGAGucucAGuGuudTsdT | NM_014143.2_1331-1349s |
| 848 | A-55135.1 | AAcACUGAGACUCUcAGUCdTsdT | NM_014143.2_1331-1349s |
| 849 AD-24518.1 | A-55136.1 | GAGucucAGuGuuGGAAcGdTsdT | NM_014143.2_1337-1355s |
| 850 | A-55137.1 | CGUUCcAAcACUGAGACUCdTsdT | NM_014143.2_1337-1355s |
| 851 AD-24519.1 | A-55138.1 | cucAGuGuuGGAAcGGGAcdTsdT | NM_014143.2_1341-1359s |
| 852 | A-55139.1 | GUCCCGUUCcAAcACUGAGdTsdT | NM_014143.2_1341-1359s |
| 853 AD-24520.1 | A-55140.1 | uuAuuuuGAGucuGuGAGGdTsdT | NM_014143.2_1386-1404s |
| 854 | A-55141.1 | CCUcAcAGACUcAAAAuAAdTsdT | NM_014143.2_1386-1404s |
| 855 AD-24521.1 | A-55142.1 | AuuuuGAGucuGuGAGGucdTsdT | NM_014143.2_1388-1406s |
| 856 | A-55143.1 | GACCUcAcAGACUcAAAAUdTsdT | NM_014143.2_1388-1406s |
| 857 AD-24522.1 | A-55144.1 | AuAuuuGuAGuAGAuGuudTsdT | NM_014143.2_1449-1467s |
| 858 | A-55145.1 | AAcAUCuACuAcAAuAuAUdTsdT | NM_014143.2_1449-1467s |
| 859 AD-24523.1 | A-55146.1 | AcuAAAcuuGcuGcuuAAudTsdT | NM_014143.2_1484-1502s |
| 860 | A-55147.1 | AUuAAGcAGcAAGUUuAGUdTsdT | NM_014143.2_1484-1502s |
| 861 AD-24524.1 | A-55148.1 | GcuGcuuAAuGAuuuGcucdTsdT | NM_014143.2_1493-1511s |
| 862 | A-55149.1 | GAGcAAAUcAUuAAGcAGCdTsdT | NM_014143.2_1493-1511s |

TABLE 3-continued

Human CD274/PD-L1 Modified Single Strands and Duplex Sequences

| SEQ ID NO: | Duplex | Single strand | Sequence | Oligo design name |
|---|---|---|---|---|
| 863 | AD-24525.1 | A-55150.1 | uuAAuGAuuuGcucAcAucdTsdT | NM_014143.2_1498-1516s |
| 864 | | A-55151.1 | GAUGUGAGcAAAUcAUuAAdTsdT | NM_014143.2_1498-1516s |
| 865 | AD-24526.1 | A-55152.1 | cAcAucuAGuAAAAcAuGGdTsdT | NM_014143.2_1511-1529s |
| 866 | | A-55153.1 | CcAUGUUUuACuAGAUGUGdTsdT | NM_014143.2_1511-1529s |
| 867 | AD-24527.1 | A-55154.1 | cuAGuAAAAcAuGGAGuAudTsdT | NM_014143.2_1516-1534s |
| 868 | | A-55155.1 | AuACUCcAUGUUUuACuAGdTsdT | NM_014143.2_1516-1534s |

TABLE 4

In vitro screening Results for Human CD274/PD-L1 iRNAs

| Duplex ID | RKO 10 nM Rep 1 | RKO 10 nM Rep 2 | RKO 10 nM Avg | RKO 0.1 nM Rep 1 | RKO 0.1 nM Rep 2 | RKO 0.1 nM Avg | Hep3B 10 nM Rep 1 | Hep3B 0.1 nM Rep 1 | RKO IC50 Rep 1(nM) | RKO IC50 Rep 2(nM) | RKO IC50 Rep 3(nM) |
|---|---|---|---|---|---|---|---|---|---|---|---|
| AD-22303-b1 | 0.37 | 0.40 | 0.39 | 0.82 | 0.84 | 0.83 | 0.47 | 0.58 | | | |
| AD-22304-b1 | 0.80 | 0.78 | 0.79 | 0.89 | 0.89 | 0.89 | 0.87 | 1.25 | | | |
| AD-22305-b1 | 0.41 | 0.41 | 0.41 | 0.84 | 0.79 | 0.81 | 0.87 | 0.88 | | | |
| AD-22306-b1 | 0.54 | 0.56 | 0.55 | 0.87 | 0.88 | 0.88 | 0.89 | 1.11 | | | |
| AD-22307-b1 | 0.84 | 0.87 | 0.86 | 0.96 | 0.96 | 0.96 | 1.03 | 1.12 | | | |
| AD-22309-b1 | 0.34 | 0.43 | 0.38 | 0.52 | 0.56 | 0.54 | 0.52 | 0.54 | | | |
| AD-22310-b1 | 0.24 | 0.25 | 0.25 | 0.82 | 0.79 | 0.80 | 0.54 | 0.60 | | | |
| AD-22311-b1 | 0.70 | 0.74 | 0.72 | 0.95 | 0.90 | 0.92 | 0.83 | 1.04 | | | |
| AD-22312-b1 | 0.37 | 0.35 | 0.36 | 0.76 | 0.67 | 0.71 | 0.44 | 0.55 | | | |
| AD-22313-b1 | 0.83 | 0.73 | 0.78 | 0.93 | 0.90 | 0.91 | 0.35 | 0.99 | | | |
| AD-22314-b1 | 0.67 | 0.58 | 0.62 | 0.93 | 0.80 | 0.86 | 0.84 | 1.22 | | | |
| AD-22315-b1 | 0.98 | 0.98 | 0.98 | 1.11 | 0.91 | 1.01 | 1.08 | 1.18 | | | |
| AD-22316-b1 | 0.68 | 0.65 | 0.67 | 0.91 | 0.87 | 0.89 | 0.72 | 1.47 | | | |
| AD-22317-b1 | 0.65 | 0.60 | 0.63 | 0.92 | 0.89 | 0.90 | 1.07 | 0.89 | | | |
| AD-22318-b1 | 0.73 | 0.68 | 0.71 | 0.96 | 0.89 | 0.92 | 1.07 | 0.83 | | | |
| AD-22319-b1 | 0.40 | 0.40 | 0.40 | 0.90 | 0.90 | 0.90 | 0.76 | 1.10 | | | |
| AD-22320-b1 | 0.80 | 0.76 | 0.78 | 0.96 | 0.91 | 0.93 | 0.84 | 0.88 | | | |
| AD-22321-b1 | 0.59 | 0.58 | 0.59 | 0.93 | 0.89 | 0.91 | 0.88 | 0.79 | | | |
| AD-22322-b1 | 0.83 | 0.76 | 0.80 | 0.94 | 0.97 | 0.95 | 0.85 | 1.05 | | | |
| AD-22323-b1 | 0.84 | 0.78 | 0.81 | 1.00 | 0.94 | 0.97 | 0.82 | 0.42 | | | |
| AD-22325-b1 | 0.63 | 0.56 | 0.59 | 0.97 | 0.89 | 0.93 | 0.54 | 0.65 | | | |
| AD-22326-b1 | 0.58 | 0.48 | 0.53 | 0.92 | 0.86 | 0.89 | 0.45 | 1.33 | | | |
| AD-22327-b1 | 0.58 | 0.49 | 0.54 | 0.92 | 0.87 | 0.90 | 0.58 | 1.00 | | | |
| AD-22328-b1 | 0.88 | 0.74 | 0.81 | 0.97 | 0.85 | 0.91 | 1.07 | 1.09 | | | |
| AD-22329-b1 | 0.81 | 0.73 | 0.77 | 0.96 | 0.93 | 0.95 | 0.61 | 0.90 | | | |
| AD-22330-b1 | 0.90 | 0.86 | 0.88 | 0.99 | 0.95 | 0.97 | 1.13 | 0.90 | | | |
| AD-22331-b1 | 0.56 | 0.61 | 0.59 | 0.94 | 0.89 | 0.91 | 0.75 | 0.59 | | | |
| AD-22332-b1 | 0.91 | 0.89 | 0.90 | 0.94 | 0.95 | 0.94 | 0.84 | 1.14 | | | |
| AD-22333-b1 | 0.41 | 0.38 | 0.39 | 0.84 | 0.85 | 0.84 | 0.74 | 0.92 | | | |
| AD-22334-b1 | 0.97 | 0.94 | 0.96 | 0.97 | 0.97 | 0.97 | 1.32 | 1.35 | | | |
| AD-22335-b1 | 0.99 | 0.88 | 0.93 | 0.96 | 1.00 | 0.98 | 1.09 | 0.83 | | | |
| AD-22336-b1 | 0.62 | 0.56 | 0.59 | 0.93 | 0.99 | 0.96 | 0.71 | 0.79 | | | |
| AD-22337-b1 | 0.71 | 0.65 | 0.68 | 1.01 | 0.95 | 0.98 | 0.55 | 0.67 | | | |
| AD-22338-b1 | 0.31 | 0.30 | 0.30 | 0.81 | 0.77 | 0.79 | 0.76 | 0.75 | | | |
| AD-22339-b1 | 0.79 | 0.83 | 0.81 | 0.96 | 0.93 | 0.94 | 0.78 | 0.57 | | | |
| AD-22340-b1 | 0.45 | 0.49 | 0.47 | 0.96 | 0.76 | 0.86 | 0.54 | 0.90 | | | |
| AD-22341-b1 | 0.50 | 0.51 | 0.50 | 0.96 | 0.88 | 0.92 | 0.67 | 0.89 | | | |
| AD-22342-b1 | 0.32 | 0.29 | 0.31 | 0.82 | 0.79 | 0.81 | 0.53 | 0.66 | | | |
| AD-22343-b1 | 0.26 | 0.27 | 0.27 | 0.69 | 0.72 | 0.71 | 0.34 | 0.62 | | | |
| AD-22344-b1 | 1.00 | 0.95 | 0.98 | 0.97 | 0.96 | 0.96 | 0.57 | 0.88 | | | |
| AD-22345-b1 | 0.80 | 0.78 | 0.79 | 0.97 | 0.99 | 0.98 | 1.05 | 1.73 | | | |
| AD-22346-b1 | 0.78 | 0.76 | 0.77 | 0.96 | 0.91 | 0.93 | 0.69 | 0.69 | | | |
| AD-22347-b1 | 0.67 | 0.59 | 0.63 | 0.78 | 0.79 | 0.78 | 0.61 | 0.47 | | | |
| AD-22348-b1 | 0.94 | 0.87 | 0.90 | 0.94 | 0.94 | 0.94 | 0.68 | 0.63 | | | |
| AD-22349-b1 | 0.12 | 0.11 | 0.11 | 0.66 | 0.64 | 0.65 | 0.30 | 0.33 | | | |
| AD-22350-b1 | 0.68 | 0.64 | 0.66 | 0.93 | 0.89 | 0.91 | 0.87 | 0.81 | | | |
| AD-1955 | 1.04 | 1.00 | 1.02 | 0.97 | 0.96 | 0.96 | ND | ND | | | |
| AD-1955 | 1.05 | 1.02 | 1.04 | 0.97 | 1.01 | 0.99 | ND | ND | | | |
| AD-1955 | 0.99 | 0.92 | 0.95 | 0.98 | 0.99 | 0.98 | ND | ND | | | |
| AD-1955 | 0.97 | 0.95 | 0.96 | 0.97 | 1.03 | 1.00 | ND | ND | | | |
| AD-1955 | 1.00 | 1.05 | 1.02 | 0.99 | 1.00 | 1.00 | ND | ND | | | |

TABLE 4-continued

In vitro screening Results for Human CD274/PD-L1 iRNAs

| | RKO | | | | | | Hep3B | | RKO | | |
|---|---|---|---|---|---|---|---|---|---|---|---|
| | | | | | | | | | IC50 | IC50 | IC50 |
| Duplex ID | 10 nM Rep 1 | 10 nM Rep 2 | 10 nM Avg | 0.1 nM Rep 1 | 0.1 nM Rep 2 | 0.1 nM Avg | 10 nM Rep 1 | 0.1 nM Rep 1 | Rep 1(nM) | Rep 2(nM) | Rep 3(nM) |
| AD-1955 | 0.96 | 1.07 | 1.01 | 0.38 | 1.01 | 0.69 | ND | ND | | | |
| AD-24151-b1 | 0.79 | 0.78 | 0.79 | 0.83 | 0.86 | 0.85 | ND | ND | | | |
| AD-24152-b1 | 1.02 | 0.95 | 0.99 | 0.98 | 0.87 | 0.92 | ND | ND | | | |
| AD-24153-b1 | 0.91 | 0.89 | 0.90 | 0.98 | 0.88 | 0.93 | ND | ND | | | |
| AD-24154-b1 | 0.93 | 0.92 | 0.93 | 0.97 | 0.94 | 0.95 | ND | ND | | | |
| AD-24155-b1 | 0.55 | 0.54 | 0.55 | 0.71 | 0.69 | 0.70 | ND | ND | | | |
| AD-24156-b1 | 0.49 | 0.49 | 0.49 | 0.89 | 0.86 | 0.87 | ND | ND | | | |
| AD-24157-b1 | 0.68 | 0.72 | 0.70 | 0.93 | 0.85 | 0.89 | ND | ND | | | |
| AD-24158-b1 | 0.74 | 0.74 | 0.74 | 0.95 | 0.87 | 0.91 | ND | ND | | | |
| AD-24159-b1 | 0.84 | 0.96 | 0.90 | 0.94 | 0.82 | 0.88 | ND | ND | | | |
| AD-24160-b1 | 0.24 | 0.26 | 0.25 | 0.54 | 0.52 | 0.53 | ND | ND | | | |
| AD-24161-b1 | 0.71 | 0.78 | 0.75 | 0.84 | 0.95 | 0.90 | ND | ND | | | |
| AD-24162-b1 | 0.69 | 0.78 | 0.74 | 0.87 | 0.85 | 0.86 | ND | ND | | | |
| AD-24163-b1 | 0.94 | 0.88 | 0.91 | 1.00 | 0.94 | 0.97 | ND | ND | | | |
| AD-24164-b1 | 0.88 | 0.82 | 0.85 | 0.95 | 0.88 | 0.92 | ND | ND | | | |
| AD-24165-b1 | 1.00 | 0.89 | 0.94 | 0.96 | 0.93 | 0.94 | ND | ND | | | |
| AD-24166-b1 | 0.70 | 0.66 | 0.68 | 0.85 | 0.89 | 0.87 | ND | ND | | | |
| AD-24167-b1 | 0.89 | 0.90 | 0.89 | 0.95 | 0.92 | 0.94 | ND | ND | | | |
| AD-24168-b1 | 0.58 | 0.60 | 0.59 | 0.80 | 0.76 | 0.78 | ND | ND | | | |
| AD-24169-b1 | 0.13 | 0.13 | 0.13 | 0.41 | 0.31 | 0.36 | ND | ND | 0.276 | 0.070 | 0.030 |
| AD-24170-b1 | 0.30 | 0.32 | 0.31 | 0.63 | 0.52 | 0.58 | ND | ND | | | |
| AD-24171-b1 | 0.71 | 0.67 | 0.69 | 0.89 | 0.86 | 0.88 | ND | ND | | | |
| AD-24172-b1 | 0.54 | 0.49 | 0.52 | 0.75 | 0.70 | 0.73 | ND | ND | | | |
| AD-24173-b1 | 0.30 | 0.28 | 0.29 | 0.70 | 0.54 | 0.62 | ND | ND | | | |
| AD-24174-b1 | 0.94 | 0.88 | 0.91 | 0.94 | 0.82 | 0.88 | ND | ND | | | |
| AD-24175-b1 | 0.14 | 0.15 | 0.14 | 0.62 | 0.47 | 0.55 | ND | ND | 0.383 | 0.074 | 0.015 |
| AD-24176-b1 | 0.53 | 0.49 | 0.51 | 0.91 | 0.89 | 0.90 | ND | ND | | | |
| AD-24177-b1 | 0.95 | 0.85 | 0.90 | 0.96 | 0.91 | 0.94 | ND | ND | | | |
| AD-24178-b1 | 0.25 | 0.28 | 0.26 | 0.83 | 0.75 | 0.79 | ND | ND | | | |
| AD-24179-b1 | 0.64 | 0.66 | 0.65 | 0.91 | 0.93 | 0.92 | ND | ND | | | |
| AD-24180-b1 | 0.84 | 0.93 | 0.88 | 0.88 | 0.90 | 0.89 | ND | ND | | | |
| AD-24181-b1 | 0.89 | 0.90 | 0.90 | 0.95 | 1.01 | 0.98 | ND | ND | | | |
| AD-24182-b1 | 0.85 | 0.81 | 0.83 | 0.96 | 0.86 | 0.91 | ND | ND | | | |
| AD-24183-b1 | 0.79 | 0.75 | 0.77 | 0.91 | 0.82 | 0.86 | ND | ND | | | |
| AD-24184-b1 | 0.67 | 0.57 | 0.62 | 0.95 | 0.92 | 0.93 | ND | ND | | | |
| AD-24185-b1 | 0.45 | 0.43 | 0.44 | 0.87 | 0.88 | 0.88 | ND | ND | | | |
| AD-24186-b1 | 0.97 | 0.90 | 0.94 | 0.95 | 0.91 | 0.93 | ND | ND | | | |
| AD-24187-b1 | 0.23 | 0.23 | 0.23 | 0.44 | 0.43 | 0.43 | ND | ND | | | |
| AD-24188-b1 | 0.79 | 0.82 | 0.80 | 0.84 | 0.83 | 0.84 | ND | ND | | | |
| AD-24189-b1 | 0.72 | 0.79 | 0.75 | 0.78 | 0.81 | 0.79 | ND | ND | | | |
| AD-24190-b1 | 0.33 | 0.35 | 0.34 | 0.57 | 0.55 | 0.56 | ND | ND | | | |
| AD-24191-b1 | 0.84 | 0.87 | 0.86 | 0.88 | 0.93 | 0.91 | ND | ND | | | |
| AD-24192-b1 | 0.98 | 0.98 | 0.98 | 0.93 | 0.91 | 0.92 | ND | ND | | | |
| AD-24193-b1 | 0.96 | 1.03 | 0.99 | 0.93 | 0.96 | 0.95 | ND | ND | | | |
| AD-24194-b1 | 0.28 | 0.29 | 0.29 | 0.76 | 0.68 | 0.72 | ND | ND | | | |
| AD-24195-b1 | 0.61 | 0.60 | 0.60 | 0.77 | 0.79 | 0.78 | ND | ND | | | |
| AD-24196-b1 | 0.69 | 0.76 | 0.72 | 0.91 | 0.82 | 0.86 | ND | ND | | | |
| AD-24197-b1 | 1.02 | 0.97 | 1.00 | 0.87 | 0.88 | 0.88 | ND | ND | | | |
| AD-24198-b1 | 0.91 | 0.86 | 0.89 | 0.94 | 0.82 | 0.88 | ND | ND | | | |
| AD-24199-b1 | 0.64 | 0.66 | 0.65 | 0.89 | 0.84 | 0.87 | ND | ND | | | |
| AD-24200-b1 | 0.87 | 0.86 | 0.87 | 0.98 | 0.92 | 0.95 | ND | ND | | | |
| AD-24201-b1 | 0.43 | 0.41 | 0.42 | 0.82 | 0.75 | 0.79 | ND | ND | | | |
| AD-24202-b1 | 0.87 | 0.95 | 0.91 | 0.89 | 0.96 | 0.93 | ND | ND | | | |
| AD-24203-b1 | 0.91 | 0.94 | 0.93 | 0.86 | 0.89 | 0.87 | ND | ND | | | |
| AD-24204-b1 | 0.61 | 0.71 | 0.66 | 0.88 | 0.76 | 0.82 | ND | ND | | | |
| AD-24205-b1 | 0.33 | 0.35 | 0.34 | 0.67 | 0.63 | 0.65 | ND | ND | | | |
| AD-24206-b1 | 0.50 | 0.51 | 0.51 | 0.72 | 0.72 | 0.72 | ND | ND | | | |
| AD-24207-b1 | 0.55 | 0.54 | 0.55 | 0.73 | 0.66 | 0.70 | ND | ND | | | |
| AD-24208-b1 | 0.84 | 0.82 | 0.83 | 0.93 | 0.87 | 0.90 | ND | ND | | | |
| AD-24209-b1 | 0.26 | 0.23 | 0.25 | 0.63 | 0.41 | 0.52 | ND | ND | | | |
| AD-21113-b2 | 1.11 | 0.93 | 1.02 | 0.99 | 0.89 | 0.94 | ND | ND | | | |
| AD-24210-b1 | 1.94 | 1.76 | 1.85 | 1.24 | 1.21 | 1.23 | ND | ND | | | |
| AD-24211-b1 | 0.39 | 0.42 | 0.41 | 0.67 | 0.59 | 0.63 | ND | ND | | | |
| AD-24212-b1 | 0.66 | 0.62 | 0.64 | 0.83 | 0.82 | 0.82 | ND | ND | | | |
| AD-24213-b1 | 0.65 | 0.76 | 0.71 | 0.80 | 0.84 | 0.82 | ND | ND | | | |
| AD-24214-b1 | 0.29 | 0.23 | 0.26 | 0.66 | 0.57 | 0.61 | ND | ND | | | |
| AD-24215-b1 | 0.79 | 0.75 | 0.77 | 0.85 | 0.81 | 0.83 | ND | ND | | | |
| AD-24216-b1 | 0.63 | 0.64 | 0.64 | 0.84 | 0.79 | 0.82 | ND | ND | | | |
| AD-24217-b1 | 0.66 | 0.67 | 0.66 | 0.84 | 0.77 | 0.81 | ND | ND | | | |
| AD-24218-b1 | 0.30 | 0.30 | 0.30 | 0.67 | 0.54 | 0.61 | ND | ND | | | |
| AD-24219-b1 | 0.52 | 0.56 | 0.54 | 0.84 | 0.77 | 0.80 | ND | ND | | | |

TABLE 4-continued

In vitro screening Results for Human CD274/PD-L1 iRNAs

| | RKO | | | | | | Hep3B | | RKO | | |
|---|---|---|---|---|---|---|---|---|---|---|---|
| Duplex ID | 10 nM Rep 1 | 10 nM Rep 2 | 10 nM Avg | 0.1 nM Rep 1 | 0.1 nM Rep 2 | 0.1 nM Avg | 10 nM Rep 1 | 0.1 nM Rep 1 | IC50 Rep 1(nM) | IC50 Rep 2(nM) | IC50 Rep 3(nM) |
| AD-24220-b1 | 0.56 | 0.48 | 0.52 | 0.83 | 0.67 | 0.75 | ND | ND | | | |
| AD-24221-b1 | 1.10 | 1.06 | 1.08 | 1.00 | 0.92 | 0.96 | ND | ND | | | |
| AD-24222-b1 | 1.09 | 1.02 | 1.06 | 0.97 | 0.94 | 0.95 | ND | ND | | | |
| AD-24223-b1 | 0.97 | 0.93 | 0.95 | 0.91 | 0.89 | 0.90 | ND | ND | | | |
| AD-24224-b1 | 0.97 | 0.94 | 0.95 | 0.89 | 0.93 | 0.91 | ND | ND | | | |
| AD-24225-b1 | 0.76 | 0.76 | 0.76 | 0.84 | 0.86 | 0.85 | ND | ND | | | |
| AD-24226-b1 | 0.69 | 0.73 | 0.71 | 0.79 | 0.78 | 0.78 | ND | ND | | | |
| AD-24227-b1 | 0.80 | 0.84 | 0.82 | 0.87 | 0.86 | 0.86 | ND | ND | | | |
| AD-24228-b1 | 0.51 | 0.53 | 0.52 | 0.82 | 0.76 | 0.79 | ND | ND | | | |
| AD-24229-b1 | 0.72 | 0.75 | 0.74 | 0.96 | 0.85 | 0.91 | ND | ND | | | |
| AD-24230-b1 | 0.16 | 0.16 | 0.16 | 0.40 | 0.36 | 0.38 | ND | ND | 0.164 | 0.032 | 0.009 |
| AD-24231-b1 | 0.36 | 0.36 | 0.36 | 0.60 | 0.48 | 0.54 | ND | ND | | | |
| AD-24232-b1 | 0.84 | 0.77 | 0.80 | 0.84 | 0.85 | 0.84 | ND | ND | | | |
| AD-24233-b1 | 0.30 | 0.29 | 0.29 | 0.60 | 0.54 | 0.57 | ND | ND | | | |
| AD-24234-b1 | 0.63 | 0.63 | 0.63 | 0.80 | 0.89 | 0.85 | ND | ND | | | |
| AD-24235-b1 | 0.43 | 0.48 | 0.45 | 0.66 | 0.60 | 0.63 | ND | ND | | | |
| AD-24236-b1 | 0.76 | 0.70 | 0.73 | 0.82 | 0.70 | 0.76 | ND | ND | | | |
| AD-24237-b1 | 0.62 | 0.73 | 0.68 | 0.90 | 0.77 | 0.83 | ND | ND | | | |
| AD-24238-b1 | 0.67 | 0.67 | 0.67 | 0.87 | 0.80 | 0.84 | ND | ND | | | |
| AD-24239-b1 | 0.54 | 0.64 | 0.59 | 0.91 | 0.76 | 0.84 | ND | ND | | | |
| AD-24240-b1 | 0.62 | 0.73 | 0.68 | 0.88 | 0.61 | 0.74 | ND | ND | | | |
| AD-24241-b1 | 0.31 | 0.36 | 0.33 | 0.17 | 0.53 | 0.35 | ND | ND | 0.383 | 0.282 | 0.180 |
| AD-24242-b1 | 0.54 | 0.62 | 0.58 | 0.79 | 0.63 | 0.71 | ND | ND | | | |
| AD-24243-b1 | 0.79 | 0.78 | 0.78 | 0.74 | 0.79 | 0.77 | ND | ND | | | |
| AD-24244-b1 | 0.90 | 1.10 | 1.00 | 0.86 | 0.83 | 0.84 | ND | ND | | | |
| AD-24245-b1 | 0.76 | 0.94 | 0.85 | 0.99 | 0.86 | 0.92 | ND | ND | | | |
| AD-24455-b1 | 0.33 | 0.34 | 0.34 | 0.66 | 0.73 | 0.69 | ND | ND | | | |
| AD-24456-b1 | 0.59 | 0.68 | 0.64 | 0.72 | 0.66 | 0.69 | ND | ND | | | |
| AD-24457-b1 | 0.71 | 0.82 | 0.76 | 0.73 | 0.84 | 0.78 | ND | ND | | | |
| AD-24458-b1 | 0.59 | 0.55 | 0.57 | 0.69 | 0.68 | 0.69 | ND | ND | | | |
| AD-24459-b1 | 0.81 | 0.86 | 0.83 | 0.77 | 0.98 | 0.87 | ND | ND | | | |
| AD-24460-b1 | 1.25 | 1.12 | 1.18 | 1.04 | 1.12 | 1.08 | ND | ND | | | |
| AD-24461-b1 | 0.79 | 0.85 | 0.82 | 0.86 | 0.91 | 0.89 | ND | ND | | | |
| AD-24462-b1 | 0.82 | 0.88 | 0.85 | 0.90 | 0.93 | 0.91 | ND | ND | | | |
| AD-24463-b1 | 0.97 | 0.98 | 0.98 | 0.86 | 0.98 | 0.92 | ND | ND | | | |
| AD-24464-b1 | 0.73 | 0.85 | 0.79 | 0.88 | 0.82 | 0.85 | ND | ND | | | |
| AD-24465-b1 | 0.97 | 1.00 | 0.99 | 0.82 | 0.95 | 0.89 | ND | ND | | | |
| AD-24466-b1 | 0.78 | 0.83 | 0.81 | 0.86 | 0.84 | 0.85 | ND | ND | | | |
| AD-24467-b1 | 0.26 | 0.27 | 0.26 | 0.37 | 0.45 | 0.41 | ND | ND | 0.283 | 0.112 | 0.115 |
| AD-24468-b1 | 0.59 | 0.63 | 0.61 | 0.58 | 0.73 | 0.66 | ND | ND | | | |
| AD-24469-b1 | 0.76 | 0.77 | 0.76 | 0.76 | 0.74 | 0.75 | ND | ND | | | |
| AD-24470-b1 | 0.28 | 0.35 | 0.32 | 0.54 | 0.59 | 0.56 | ND | ND | | | |
| AD-24471-b1 | 0.46 | 0.54 | 0.50 | 0.70 | 0.78 | 0.74 | ND | ND | | | |
| AD-24472-b1 | 0.37 | 0.36 | 0.37 | 0.53 | 0.59 | 0.56 | ND | ND | | | |
| AD-24473-b1 | 1.00 | 0.96 | 0.98 | 0.95 | 1.03 | 0.99 | ND | ND | | | |
| AD-24474-b1 | 0.39 | 0.40 | 0.39 | 0.58 | 0.64 | 0.61 | ND | ND | | | |
| AD-24475-b1 | 0.56 | 0.59 | 0.57 | 0.74 | 0.82 | 0.78 | ND | ND | | | |
| AD-24476-b1 | 0.15 | 0.19 | 0.17 | 0.47 | 0.48 | 0.47 | ND | ND | 0.428 | 0.111 | 0.039 |
| AD-24477-b1 | 0.32 | 0.33 | 0.33 | 0.55 | 0.65 | 0.60 | ND | ND | | | |
| AD-24478-b1 | 0.81 | 0.78 | 0.79 | 0.88 | 0.87 | 0.88 | ND | ND | | | |
| AD-24479-b1 | 0.51 | 0.51 | 0.51 | 0.55 | 0.74 | 0.64 | ND | ND | | | |
| AD-24480-b1 | 0.50 | 0.48 | 0.49 | 0.50 | 0.59 | 0.54 | ND | ND | | | |
| AD-24481-b1 | 0.36 | 0.40 | 0.38 | 0.49 | 0.62 | 0.56 | ND | ND | | | |
| AD-24482-b1 | 0.23 | 0.29 | 0.26 | 0.54 | 0.73 | 0.63 | ND | ND | | | |
| AD-24483-b1 | 0.16 | 0.21 | 0.18 | 0.46 | 0.53 | 0.49 | ND | ND | 0.509 | 0.132 | 0.087 |
| AD-24484-b1 | 0.63 | 0.73 | 0.68 | 0.74 | 0.97 | 0.86 | ND | ND | | | |
| AD-24485-b1 | 0.54 | 0.61 | 0.58 | 0.59 | 0.75 | 0.67 | ND | ND | | | |
| AD-24486-b1 | 0.32 | 0.44 | 0.38 | 0.48 | 0.63 | 0.55 | ND | ND | | | |
| AD-24487-b1 | 0.11 | 0.14 | 0.13 | 0.26 | 0.28 | 0.27 | ND | ND | 0.939 | 0.013 | 0.011 |
| AD-24488-b1 | 0.29 | 0.37 | 0.33 | 0.50 | 0.61 | 0.56 | ND | ND | | | |
| AD-24489-b1 | 0.37 | 0.47 | 0.42 | 0.53 | 0.67 | 0.60 | ND | ND | | | |
| AD-24490-b1 | 0.60 | 0.53 | 0.57 | 0.65 | 0.73 | 0.69 | ND | ND | | | |
| AD-24491-b1 | 0.84 | 0.85 | 0.84 | 0.73 | 0.90 | 0.81 | ND | ND | | | |
| AD-24492-b1 | 0.43 | 0.49 | 0.46 | 0.42 | 0.51 | 0.46 | ND | ND | | | |
| AD-24493-b1 | 0.64 | 0.69 | 0.67 | 0.63 | 0.67 | 0.65 | ND | ND | | | |
| AD-24494-b1 | 0.29 | 0.37 | 0.33 | 0.42 | 0.49 | 0.45 | ND | ND | | | |
| AD-24495-b1 | 0.24 | 0.29 | 0.26 | 0.32 | 0.39 | 0.35 | ND | ND | 0.161 | 0.056 | 0.037 |
| AD-24496-b1 | 0.13 | 0.20 | 0.17 | 0.33 | 0.33 | 0.33 | ND | ND | 0.143 | 0.007 | 0.001 |
| AD-24497-b1 | 0.65 | 0.67 | 0.66 | 0.68 | 0.75 | 0.71 | ND | ND | | | |
| AD-24498-b1 | 0.69 | 0.72 | 0.70 | 0.72 | 0.88 | 0.80 | ND | ND | | | |
| AD-24499-b1 | 0.52 | 0.61 | 0.57 | 0.58 | 0.72 | 0.65 | ND | ND | | | |

TABLE 4-continued

In vitro screening Results for Human CD274/PD-L1 iRNAs

| Duplex ID | RKO 10 nM Rep 1 | RKO 10 nM Rep 2 | RKO 10 nM Avg | RKO 0.1 nM Rep 1 | RKO 0.1 nM Rep 2 | RKO 0.1 nM Avg | Hep3B 10 nM Rep 1 | Hep3B 0.1 nM Rep 1 | RKO IC50 Rep 1(nM) | RKO IC50 Rep 2(nM) | RKO IC50 Rep 3(nM) |
|---|---|---|---|---|---|---|---|---|---|---|---|
| AD-24500-b1 | 0.85 | 0.93 | 0.89 | 0.86 | 0.83 | 0.85 | ND | ND | | | |
| AD-24501-b1 | 0.84 | 0.91 | 0.87 | 0.82 | 0.90 | 0.86 | ND | ND | | | |
| AD-24502-b1 | 0.60 | 0.67 | 0.63 | 0.77 | 0.81 | 0.79 | ND | ND | | | |
| AD-24503-b1 | 0.84 | 0.88 | 0.86 | 0.76 | 0.95 | 0.86 | ND | ND | | | |
| AD-24504-b1 | 0.37 | 0.44 | 0.40 | 0.55 | 0.60 | 0.58 | ND | ND | | | |
| AD-24505-b1 | 0.69 | 0.70 | 0.70 | 0.70 | 0.87 | 0.79 | ND | ND | | | |
| AD-24506-b1 | 0.31 | 0.33 | 0.32 | 0.40 | 0.51 | 0.46 | ND | ND | | | |
| AD-24507-b1 | 0.38 | 0.55 | 0.46 | 0.45 | 0.61 | 0.53 | ND | ND | | | |
| AD-24508-b1 | 0.64 | 0.70 | 0.67 | 0.69 | 0.77 | 0.73 | ND | ND | | | |
| AD-24509-b1 | 0.84 | 0.76 | 0.80 | 0.72 | 0.81 | 0.76 | ND | ND | | | |
| AD-24510-b1 | 0.83 | 0.93 | 0.88 | 0.78 | 0.87 | 0.82 | ND | ND | | | |
| AD-24511-b1 | 0.44 | 0.50 | 0.47 | 0.61 | 0.68 | 0.64 | ND | ND | | | |
| AD-24512-b1 | 0.26 | 0.28 | 0.27 | 0.37 | 0.42 | 0.39 | ND | ND | 0.308 | 0.046 | 0.026 |
| AD-24513-b1 | 0.36 | 0.39 | 0.37 | 0.40 | 0.53 | 0.47 | ND | ND | | | |
| AD-24514-b1 | 0.37 | 0.36 | 0.36 | 0.46 | 0.44 | 0.45 | ND | ND | | | |
| AD-24515-b1 | 0.35 | 0.31 | 0.33 | 0.39 | 0.46 | 0.43 | ND | ND | | | |
| AD-24516-b1 | 0.21 | 0.29 | 0.25 | 0.29 | 0.35 | 0.32 | ND | ND | 0.104 | 0.024 | 0.015 |
| AD-24517-b1 | 0.19 | 0.21 | 0.20 | 0.23 | 0.28 | 0.25 | ND | ND | 0.021 | 0.005 | 0.003 |
| AD-24518-b1 | 0.21 | 0.32 | 0.27 | 0.29 | 0.30 | 0.30 | ND | ND | 0.049 | 0.010 | 0.009 |
| AD-24519-b1 | 0.32 | 0.30 | 0.31 | 0.42 | 0.34 | 0.38 | ND | ND | 4.481 | 0.052 | 0.115 |
| AD-24520-b1 | 0.38 | 0.42 | 0.40 | 0.47 | 0.51 | 0.49 | ND | ND | | | |
| AD-24521-b1 | 0.45 | 0.48 | 0.47 | 0.46 | 0.56 | 0.51 | ND | ND | | | |
| AD-24522-b1 | 0.37 | 0.39 | 0.38 | 0.42 | 0.36 | 0.39 | ND | ND | 0.219 | 0.051 | 0.045 |
| AD-24523-b1 | 0.60 | 0.58 | 0.59 | 0.60 | 0.67 | 0.64 | ND | ND | | | |
| AD-24524-b1 | 0.33 | 0.40 | 0.36 | 0.42 | 0.48 | 0.45 | ND | ND | | | |
| AD-24525-b1 | 0.51 | 0.53 | 0.52 | 0.56 | 0.67 | 0.62 | ND | ND | | | |
| AD-24526-b1 | 0.52 | 0.53 | 0.53 | 0.75 | 0.88 | 0.81 | ND | ND | | | |
| AD-24527-b1 | 0.65 | 0.68 | 0.66 | 0.62 | 0.65 | 0.63 | ND | ND | | | |

TABLE 5

Human CD274/PD-L1 Single Strands and Duplex Sequences

| Duplex Name | Duplex Idx | SEQ ID NO: | Sense (s) OligoName | Sense OligoSeq | SEQ ID NO: | asOligoName | asOligoSeq |
|---|---|---|---|---|---|---|---|
| AD-31053.1 | 13430449 | 877 | A-67871.1 | uGAAuAuAucuuAAcGccAdTsdT | 901 | A-67872.1 | UGGCGUuAAGAuAuAUUcAdTsdT |
| AD-31054.1 | 13430466 | 878 | A-67873.1 | GcuAGAAAGAAuccuGGGudTsdT | 902 | A-67874.1 | ACCcAGGAUUCUUUCuAGCdTsdT |
| AD-31055.1 | 13430483 | 879 | A-67875.1 | GGAGcuAcuGcAuGuuGAudTsdT | 903 | A-67876.1 | AUcAAcAUGcAGuAGCUCCdTsdT |
| AD-31056.1 | 13430500 | 880 | A-67877.1 | AGuccucAuAucAAAuAcAdTsdT | 904 | A-67878.1 | UGuAUUUGAuAUGAGGACUdTsdT |
| AD-31057.1 | 13430517 | 881 | A-67879.1 | ucAuAucAAAuAcAGAAcAdTsdT | 905 | A-67880.1 | UGUUCUGuAUUUGAuAUGAdTsdT |
| AD-31058.1 | 13430534 | 882 | A-67881.1 | cAuAucAAAuAcAGAAcAudTsdT | 906 | A-67882.1 | AUGUUCUGuAUUUGAuAUGdTsdT |
| AD-31059.1 | 13430551 | 883 | A-67883.1 | uccuGcuAAuGuuGAGccudTsdT | 907 | A-67884.1 | AGGCUcAAcAUuAGcAGGAdTsdT |
| AD-31060.1 | 13430568 | 884 | A-67885.1 | GcuAAuGuuGAGccuGGAAdTsdT | 908 | A-67886.1 | UUCcAGGCUcAAcAUuAGCdTsdT |
| AD-31061.1 | 13430585 | 885 | A-67887.1 | ucccuAAGGAAcuGuAcAudTsdT | 909 | A-67888.1 | AUGuAcAGUUCCuuAGGGAdTsdT |
| AD-31062.1 | 13430602 | 886 | A-67889.1 | cccuAAGGAAcuGuAcAuAdTsdT | 910 | A-67890.1 | uAUGuAcAGUUCCuuAGGGdTsdT |
| AD-31063.1 | 13430619 | 887 | A-67891.1 | uAcuAAuAGAGcAuGGcAdTsdT | 911 | A-67892.1 | UGCcAUGCUCuAuuAUGuAdTsdT |
| AD-31064.1 | 13430636 | 888 | A-67893.1 | AuAAuAGAGcAuGGcAGcAdTsdT | 912 | A-67894.1 | UGCUGCcAUGCUCuAuuAUdTsdT |
| AD-31065.1 | 13430653 | 889 | A-67895.1 | uAAuAGAGcAuGGcAGcAAdTsdT | 913 | A-67896.1 | UUGCUGCcAUGCUCuAuuAdTsdT |
| AD-31066.1 | 13430670 | 890 | A-67897.1 | AAuAGAGcAuGGcAGcAAudTsdT | 914 | A-67898.1 | AUUGCUGCcAUGCUCuAUUdTsdT |
| AD-31067.1 | 13430687 | 891 | A-67899.1 | GAcccuGGAAuGcAAcuuudTsdT | 915 | A-67900.1 | AAAGUUGcAUUCcAGGGUCdTsdT |
| AD-31068.1 | 13430704 | 892 | A-67901.1 | cAAuAAcAGccAGuuuGcAdTsdT | 916 | A-67902.1 | UGcAAACUGGCUGUuAUUGdTsdT |

TABLE 5-continued

Human CD274/PD-L1 Single Strands and Duplex Sequences

| Duplex Name | Duplex Idx | SEQ ID NO: | Sense (s) OligoName | Sense OligoSeq | SEQ ID NO: | asOligoName | asOligoSeq |
|---|---|---|---|---|---|---|---|
| AD-31069.1 | 13430721 | 893 | A-67903.1 | AuAAcAGccAGuuuGcAAAdTsdT | 917 | A-67904.1 | UUUGcAAACUGGCUGUuAUdTsdT |
| AD-31070.1 | 13430738 | 894 | A-67905.1 | uccAcAuAccucAAGuccAdTsdT | 918 | A-67906.1 | UGGACUUGAGGuAUGUGGAdTsdT |
| AD-31071.1 | 13430755 | 895 | A-67907.1 | AccAAuGcAuAAucAucuAdTsdT | 919 | A-67908.1 | uAGAUGAUuAUGcAUUGGUdTsdT |
| AD-31072.1 | 13430772 | 896 | A-67909.1 | GGAcuAcAAGuAccuGAcudTsdT | 920 | A-67910.1 | AGUcAGGuACUUGuAGUCCdTsdT |
| AD-31073.1 | 13430789 | 897 | A-67911.1 | AcuAcAAGuAccuGAcucudTsdT | 921 | A-67912.1 | AGAGUcAGGuACUUGuAGUdTsdT |
| AD-31074.1 | 13430806 | 898 | A-67913.1 | GucAAAGcuuccuAcAGGAdTsdT | 922 | A-67914.1 | UCCUGuAGGAAGCUUUGACdTsdT |
| AD-31075.1 | 13430823 | 899 | A-67915.1 | cAcucAcAuccuAAAGGuudTsdT | 923 | A-67916.1 | AACCUUuAGGAUGUGAGUGdTsdT |
| AD-31076.1 | 13430840 | 900 | A-67917.1 | ucAcAuccuAAAGGuuccAdTsdT | 924 | A-67918.1 | UGGAACCUUuAGGAUGUGAdTsdT |

We claim:

1. A double-stranded ribonucleic acid (dsRNA) for inhibiting expression of CD274/PD-L1, wherein said dsRNA comprises a sense strand and an antisense strand, wherein the sense strand comprises at least 15 contiguous nucleotides differing by no more than 3 nucleotides from the nucleotide sequence of SEQ ID NO: 415 and the antisense strand comprises at least 15 contiguous nucleotides differing by no more than 3 nucleotides from the corresponding antisense nucleotide sequence of SEQ ID NO: 416, and wherein each said strand is no more than 30 nucleotides in length.

2. A double-stranded ribonucleic acid (dsRNA) for inhibiting expression of CD274/PD-L1, wherein said dsRNA comprises a sense strand and an antisense strand, the antisense strand comprising a region of complementarity to a CD274/PD-L1 RNA transcript, which comprises at least 15 contiguous nucleotides differing by no more than 3 nucleotides from the antisense sequence of SEQ ID NO: 416, and wherein each said strand is no more than 30 nucleotides in length.

3. The dsRNA of claim 2, wherein said dsRNA comprises at least one modified nucleotide.

4. The dsRNA of claim 3, wherein at least one of said modified nucleotides is chosen from the group consisting of: a 2'-O-methyl modified nucleotide, a nucleotide comprising a 5'-phosphorothioate group, and a terminal nucleotide linked to a cholesteryl derivative or dodecanoic acid bisdecylamide group.

5. The dsRNA of claim 3, wherein said modified nucleotide is chosen from the group consisting of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

6. The dsRNA of a claim 2, wherein the region of complementarity is between 19 and 21 nucleotides in length.

7. The dsRNA of claim 6, wherein the region of complementarity is 19 nucleotides in length.

8. The dsRNA of claim 2, wherein at least one strand comprises a 3' overhang of at least 1 nucleotide.

9. The dsRNA of claim 2, wherein at least one strand comprises a 3' overhang of at least 2 nucleotides.

10. The dsRNA of claim 2, further comprising a ligand.

11. The dsRNA of claim 2, wherein the region of complementarity consists of the antisense sequence of SEQ ID NO: 416.

12. A double-stranded ribonucleic acid (dsRNA) for inhibiting expression of CD274/PD-L1, wherein said dsRNA comprises a sense strand and an antisense strand, the antisense strand comprising a region of complementarity to a CD274/PD-L1 RNA transcript, which comprises at least 15 contiguous nucleotides differing by no more than 3 nucleotides from the antisense sequence consisting of SEQ ID NO: 416 and wherein the sense strand consists of SEQ ID NO: 415.

13. A double-stranded ribonucleic acid (dsRNA) for inhibiting expression of CD274/PD-L1, wherein said dsRNA comprises a sense strand and an antisense strand, the antisense strand comprising a region of complementarity to a CD274/PD-L1 RNA transcript, which comprises at least 15 contiguous nucleotides differing by no more than 3 nucleotides from the antisense sequence consisting of SEQ ID NO: 416 and wherein the dsRNA comprises a sense strand consisting of a sense strand sequence of SEQ ID NO: 415.

14. A cell containing the dsRNA of claim 2.

15. The dsRNA of claim 2, further comprising a pharmaceutically acceptable carrier.

16. A vector encoding the dsRNA of claim 1, 2, 12, or 13.

\* \* \* \* \*

SEQUENCE LISTING

<160> NUMBER OF SEQ ID NOS: 925

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Val Ala Leu Leu Pro Ala Val Leu Leu Ala Leu Leu Ala Pro
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Leu Pro Val Leu Leu Ala Ala Pro
1               5                   10

<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Pro Pro Gln
1               5                   10

<210> SEQ ID NO 4
<211> LENGTH: 16
<212> TYPE: PRT
<213> ORGANISM: Drosophila melanogaster

<400> SEQUENCE: 4

Arg Gln Ile Lys Ile Trp Phe Gln Asn Arg Arg Met Lys Trp Lys Lys

```
<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cgacuacaag cgaauuacu                                                  19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aguaauucgc uuguagucg                                                  19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uccuaggaag acggguuga                                                  19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucaacccguc uuccuagga                                                  19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gugccgacua caagcgaau                                                  19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
auucgcuugu agucggcac                                                  19
```

```
<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccgacuacaa gcgaauuac                                                  19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
guaauucgcu uguagucgg                                                  19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gccgacuaca agcgaauua                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uaauucgcuu guagucggc                                                  19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
guuuaggggu ucaucgggg                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ccccgaugaa ccccuaaac                                                  19

<210> SEQ ID NO 17
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gauguuacaa uuugucgc                                                       19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgacaaaau uguaacauc                                                      19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gcauuuacug ucacgguuc                                                      19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gaaccgugac aguaaaugc                                                      19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gagccaucuu auuaugccu                                                      19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aggcauaaua agauggcuc                                                      19

<210> SEQ ID NO 23
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 23
agucucagug uuggaacgg                                                  19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24 ccguccaac acugagacu                                                   19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cuuuuaggag auuagaucc                                                  19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggaucuaauc uccuaaaag                                                  19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
auggaaccug gcgaaagca                                                  19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugcuuucgcc agguuccau                                                  19

<210> SEQ ID NO 29
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 29
cuaccccaag gccgaaguc                                                   19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gacuucggcc uuggguag                                                    19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uggaaccugg cgaaagcag                                                   19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cugcuuucgc cagguucca                                                   19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33 uauggguag aguauggua                                                    19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uaccauacuc uaccacaua                                                   19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 35
uggucauccc agaacuacc                                                19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gguaguucug ggaugacca                                                19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cauuuacugu cacgguucc                                                19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggaaccguga caguaaaug                                                19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ggagccaucu uauuaugcc                                                19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggcauaauaa gauggcucc                                                19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
```

-continued gacuacaagc gaauuacug                                             19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
caguaauucg cuuguaguc                                             19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cauacagcug aauugguca                                             19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ugaccaauuc agcuguaug                                             19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gcacuaauug ucuauuggg                                             19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cccaauagac aauuagugc                                             19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuuagggguu caucggggc                                             19

```
<210> SEQ ID NO 48
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gccccgauga accccuaaa                                                    19

<210> SEQ ID NO 49
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cucaaccugu gguuuaggg                                                    19

<210> SEQ ID NO 50
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cccuaaacca cagguugag                                                    19

<210> SEQ ID NO 51
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ccuaauuuga gggucaguu                                                    19

<210> SEQ ID NO 52
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
aacugacccu caaauuagg                                                    19

<210> SEQ ID NO 53
<211> LENTGH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ucucaaccug ugguuuagg                                                    19
```

```
<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccuaaaccac agguugaga                                                19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuuaggagau uagauccug                                                19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
caggaucuaa ucuccuaaa                                                19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccauugcuca uccuaggaa                                                19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uuccuaggau gagcaaugg                                                19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cccaaggacc uauaugugg                                                19

<210> SEQ ID NO 60
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ccacauauag guccuuggg                                                   19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gacggguuga gaaucccua                                                   19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uagggauucu caacccguc                                                   19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gcugcacuaa uugucuauu                                                   19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
aauagacaau uagugcagc                                                   19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuacugucac gguucccaa                                                   19

<210> SEQ ID NO 66
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 66
uugggaaccg ugacaguaa                                               19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuggucaucc cagaacuac                                               19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
guaguucugg gaugaccaa                                               19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
guggugccga cuacaagcg                                               19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cgcuuguagu cggcaccac                                               19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ccgugggaug caggcaaug                                               19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
<400> SEQUENCE: 72
cauugccugc aucccacgg                                                        19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ccaucuuauu augccuugg                                                        19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ccaaggcaua auaagaugg                                                        19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugaacgcauu uacugucac                                                        19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gugacaguaa augcguuca                                                        19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gguguagcac ugacauuca                                                        19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 78
ugaaugucag ugcuacacc                                                  19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cugaacgcau uuacuguca                                                  19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ugacaguaaa ugcguucag                                                  19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
caaggaccua uauguggua                                                  19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uaccacauau agguccuug                                                  19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
gagaccuuga uacuuucaa                                                  19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
```

-continued uugaaaguau caaggucuc         19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gggcugagcg ugacaagag         19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cucuugucac gcucagccc         19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uaugguggug ccgacuaca         19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uguagucggc accaccaua         19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aagguucagc auaguagcu         19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
agcuacuaug cugaaccuu         19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
auccuaggaa gacggguug                                                19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
caacccgucu uccuaggau                                                19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
auguuacaau uuugucgcc                                                19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcgacaaaa uuguaacau                                                19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
auuuacuguc acgguuccc                                                19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gggaaccgug acaguaaau                                                19

<210> SEQ ID NO 97

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cgcauuuacu gucacgguu                                                  19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aaccgugaca guaaaugcg                                                  19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
agguucagca uaguagcua                                                  19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uagcuacuau gcugaaccu                                                  19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
caccagccgc gcuucuguc                                                  19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gacagaagcg cggcuggug                                                  19

<210> SEQ ID NO 103
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 103
cgcgcuucug uccgccugc                                                   19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gcaggcggac agaagcgcg                                                   19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aagaugagga uauuugcug                                                   19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
cagcaaauau ccucaucuu                                                   19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cuuuauauuc augaccuac                                                   19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
guaggucaug aauauaaag                                                   19

<210> SEQ ID NO 109
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 109
auucaugacc uacuggcau                                                19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
augccaguag gucaugaau                                                19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucaugaccua cuggcauuu                                                19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
aaaugccagu aggucauga                                                19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uacuggcauu ugcugaacg                                                19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
cguucagcaa augccagua                                                19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 115
cuggcauuug cugaacgca                                                    19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ugcguucagc aaaugccag                                                    19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
auuugcugaa cgcauuuac                                                    19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
guaaaugcgu ucagcaaau                                                    19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuugcugaac gcauuuacu                                                    19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aguaaaugcg uucagcaaa                                                    19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
```

```
gcugaacgca uuuacuguc                                                    19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gacaguaaau gcguucagc                                                    19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uuuacuguca cgguuccca                                                    19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ugggaaccgu gacaguaaa                                                    19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
acgguuccca aggaccuau                                                    19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
auagguccuu gggaaccgu                                                    19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cgguucccaa ggaccuaua                                                    19
```

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uauagguccu ugggaaccg                                                19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gguucccaag gaccuauau                                                19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
auauaggucc uugggaacc                                                19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
guucccaagg accuauaug                                                19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cauauagguc cuugggaac                                                19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gaccuauaug ugguagagu                                                19

```
<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
acucuaccac auauagguc                                                     19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ugguagagua ugguagcaa                                                     19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uugcuaccau acucuacca                                                     19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
guaugguagc aauaugaca                                                     19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ugucauauug cuaccauac                                                     19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugguagcaau augacaauu                                                     19

<210> SEQ ID NO 140
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aauugucaua uugcuacca                                                    19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gguagcaaua ugacaauug                                                    19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
caauugucau auugcuacc                                                    19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
agcaauauga caauugaau                                                    19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
auucaauugu cauauugcu                                                    19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
caauaugaca auugaaugc                                                    19

<210> SEQ ID NO 146
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 146
gcauucaauu gucauauug                                                    19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
aauaugacaa uugaaugca                                                    19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ugcauucaau ugucauauu                                                    19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
auaugacaau ugaaugcaa                                                    19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uugcauucaa uugucauau                                                    19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
caauugaaug caaauuccc                                                    19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
       oligonucleotide

<400> SEQUENCE: 152
gggaauuugc auucaauug                                              19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugaaugcaaa uucccagua                                              19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
uacugggaau uugcauuca                                              19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aaugcaaauu cccaguaga                                              19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ucuacuggga auuugcauu                                              19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaaacaauua gaccuggcu                                              19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 158
agccaggucu aauuguuuu                                                    19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aaacaauuag accuggcug                                                    19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cagccagguc uaauuguuu                                                    19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ggcugcacua auugucuau                                                    19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
auagacaauu agugcagcc                                                    19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ugcacuaauu gucuauugg                                                    19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164

```
ccaauagaca auuagugca                                               19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uauugggaaa uggaggaua                                               19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
uauccuccau uucccaaua                                               19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
caauuugugc auggagagg                                               19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ccucuccaug cacaaauug                                               19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ccugaagguu cagcauagu                                               19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
acuaugcuga accuucagg                                               19
```

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ugaagguuca gcauaguag                                                    19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
cuacuaugcu gaaccuuca                                                    19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
gguucagcau aguagcuac                                                    19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
guagcuacua ugcugaacc                                                    19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
guucagcaua guagcuaca                                                    19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uguagcuacu augcugaac                                                    19

<210> SEQ ID NO 177

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uucagcauag uagcuacag                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
cuguagcuac uaugcugaa                                                19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cauaguagcu acagacaga                                                19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ucugucugua gcuacuaug                                                19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
auaguagcua cagacagag                                                19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
cucugucugu agcuacuau                                                19

<210> SEQ ID NO 183
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 183
cuacagacag agggcccgg                                                    19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ccgggcccuc ugucuguag                                                    19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
gcugcacuuc agaucacag                                                    19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
cugugaucug aagugcagc                                                    19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
cugcacuuca gaucacaga                                                    19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ucugugaucu gaagugcag                                                    19

<210> SEQ ID NO 189
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 189
ugcacuucag aucacagau                                                19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
aucugugauc ugaagugca                                                19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gcacuucaga ucacagaug                                                19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
caucugugau cugaagugc                                                19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aaauugcagg augcagggg                                                19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ccccugcauc cugcaauuu                                                19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 195
caggaugcag ggguguacc                                                19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gguacacccc ugcauccug                                                19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ggaugcaggg guguaccgc                                                19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcgguacacc ccugcaucc                                                19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
guaccgcugc augaucagc                                                19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcugaucaug cagcgguac                                                19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
```

```
accgcugcau gaucagcua                                          19
```

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202

```
uagcugauca ugcagcggu                                          19
```

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203

```
augaucagcu augguggug                                          19
```

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204

```
caccaccaua gcugaucau                                          19
```

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205

```
gcuauggugg ugccgacua                                          19
```

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206

```
uagucggcac caccauagc                                          19
```

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207

```
ugccgacuac aagcgaauu                                          19
```

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
aauucgcuug uagucggca                                              19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agcgaauuac ugugaaagu                                              19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
acuuucacag uaauucgcu                                              19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gcgaauuacu gugaaaguc                                              19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gacuuucaca guaauucgc                                              19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
cgaauuacug ugaaaguca                                              19

```
<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ugacuuucac aguaauucg                                                    19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
auuacuguga aagucaaug                                                    19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
cauugacuuu cacaguaau                                                    19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uacugugaaa gucaaugcc                                                    19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ggcauugacu uucacagua                                                    19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
aaagucaaug ccccauaca                                                    19

<210> SEQ ID NO 220
<211> LENGTH: 19
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
uguauggggc auugacuuu                                                19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gucaaugccc cauacaaca                                                19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uguuguaugg ggcauugac                                                19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
aauuuugguu guggaucca                                                19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uggauccaca accaaaauu                                                19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
auuuugguug uggauccag                                                19

<210> SEQ ID NO 226
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 226
cuggauccac aaccaaaau                                                       19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
agucaccucu gaacaugaa                                                       19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uucauguuca gaggugacu                                                       19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
accucugaac augaacuga                                                       19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
ucaguucaug uucagaggu                                                       19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
ccucugaaca ugaacugac                                                       19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
    oligonucleotide

<400> SEQUENCE: 232
gucaguucau guucagagg                                                   19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ugaacaugaa cugacaugu                                                   19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
acaugucagu ucauguuca                                                   19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
acaugaacug acaugucag                                                   19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
cugacauguc aguucaugu                                                   19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
caugaacuga caugucagg                                                   19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 238
ccugacaugu caguucaug                                                19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ugaacugaca ugucaggcu                                                19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
agccugacau gucaguuca                                                19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gaacugacau gucaggcug                                                19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
cagccugaca ugucaguuc                                                19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
gacaugucag gcugagggc                                                19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
```

```
gcccucagcc ugacauguc                                               19
```

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245

```
ugucaggcug agggcuacc                                               19
```

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246

```
gguagcccuc agccugaca                                               19
```

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247

```
uaccccaagg ccgaaguca                                               19
```

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248

```
ugacuucggc cuuggggua                                               19
```

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249

```
aaggccgaag ucaucugga                                               19
```

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250

```
uccagaugac uucggccuu                                               19
```

```
<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
cgaagucauc uggacaagc                                                19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcuuguccag augacuucg                                                19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
caucuggaca agcagugac                                                19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gucacugcuu guccagaug                                                19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
agcagugacc aucaagucc                                                19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ggacuugaug gucacugcu                                                19

<210> SEQ ID NO 257
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
ucaaguccug agugguaag                                                       19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
cuuaccacuc aggacuuga                                                       19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gaaucaacac aacaacuaa                                                       19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uuaguuguug uguugauuc                                                       19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aaucaacaca acaacuaau                                                       19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
auuaguuguu guguugauu                                                       19

<210> SEQ ID NO 263
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 263
uucuacugca cuuuuagga                                                      19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uccuaaaagu gcaguagaa                                                      19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265 gcacuuuag gagauuaga                                                       19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ucuaaucucc uaaaagugc                                                      19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uuuuaggaga uuagauccu                                                      19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
aggaucuaau cuccuaaaa                                                      19

<210> SEQ ID NO 269
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 269
uuaggagauu agauccuga                                                      19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ucaggaucua aucuccuaa                                                      19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uaggagauua gauccugag                                                      19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
cucaggaucu aaucuccua                                                      19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aggagauuag auccugagg                                                      19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ccucaggauc uaaucuccu                                                      19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 275
ggagauuaga uccugagga                                              19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
uccucaggau cuaaucucc                                              19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
aaaccauaca gcugaauug                                              19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
caauucagcu guaugguuu                                              19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
aaccauacag cugaauugg                                              19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ccaauucagc uguaugguu                                              19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
```
ccauacagcu gaauugguc                    19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
gaccaauuca gcuguaugg                    19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
auacagcuga auuggucau                    19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
augaccaauu cagcuguau                    19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcugaauugg ucaucccag                    19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
cugggaugac caaucagc                     19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ggucauccca gaacuaccu                    19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 288
agguaguucu gggaugacc                                                19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 289
uggcacaucc uccaaauga                                                19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 290 ucauuggag gaugugcca                                                 19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 291
ugaaaggacu cacuuggua                                                19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 292
uaccaaguga guccuuuca                                                19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 293
aggacucacu ugguaauuc                                                19

```
<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
gaauuaccaa gugaguccu                                                    19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gacucacuug guaauucug                                                    19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cagaauuacc aagugaguc                                                    19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ucacuuggua auucuggga                                                    19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ucccagaauu accaaguga                                                    19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gguaauucug ggagccauc                                                    19

<210> SEQ ID NO 300
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
gauggcuccc agaauuacc                                                     19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
guaauucugg gagccaucu                                                     19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
agauggcucc cagaauuac                                                     19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ucugggagcc aucuuauua                                                     19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uaauaagaug gcucccaga                                                     19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cugggagcca ucuuauuau                                                     19

<210> SEQ ID NO 306
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 306
auaauaagau ggcucccag                                                 19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ugggagccau cuuauuaug                                                 19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
cauaauaaga uggcuccca                                                 19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gggagccauc uuauuaugc                                                 19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
gcauaauaag auggcuccc                                                 19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
agccaucuua uuaugccuu                                                 19

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 312
aaggcauaau aagauggcu                                                 19

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aucuuauuau gccuuggug                                                 19

<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
caccaaggca uaauaagau                                                 19

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
uauuaugccu ugguguagc                                                 19

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
gcuacaccaa ggcauaaua                                                 19

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
auuaugccuu gguguagca                                                 19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 318
ugcuacacca aggcauaau                                               19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ugccuuggug uagcacuga                                               19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ucagugcuac accaaggca                                               19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
ugguguagca cugacauuc                                               19

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
gaaugucagu gcuacacca                                               19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
guagcacuga cauucaucu                                               19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
```

-continued agaugaaugu cagugcuac                                    19

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
cugacauuca ucuuccguu                                    19

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
aacggaagau gaaugucag                                    19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
agggagaaug auggaugug                                    19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
cacauccauc auucucccu                                    19

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uggcauccaa gauacaaac                                    19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
guuuguaucu uggaugcca                                    19

```
<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
ggcauccaag auacaaacu                                              19

<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
aguuuguauc uuggaugcc                                              19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
gcauccaaga uacaaacuc                                              19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
gaguuuguau cuuggaugc                                              19

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
caaagugaua cacauuugg                                              19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ccaaaugugu aucacuuug                                              19

<210> SEQ ID NO 337
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
gugauacaca uuuggagga                                                      19

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
uccuccaaau guguaucac                                                      19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
acacauuugg aggagacgu                                                      19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
acgucuccuc caaaugugu                                                      19

<210> SEQ ID NO 341
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
acauuuggag gagacguaa                                                      19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uuacgucucc uccaaaugu                                                      19

<210> SEQ ID NO 343
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 343
cauuuggagg agacguaau                                                19

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
auuacgucuc cuccaaaug                                                19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
ggaggagacg uaauccagc                                                19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
gcuggauuac gucuccucc                                                19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
acguaaucca gcauuggaa                                                19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uuccaaugcu ggauuacgu                                                19

<210> SEQ ID NO 349
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 349
aaccuguggu uuaggggguu                                                  19

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aaccccuaaa ccacagguu                                                   19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ccugugguuu agggguuca                                                   19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352 ugaacccccua aaccacagg                                                  19

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
cugugguuua gggguucau                                                   19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
augaaccccu aaaccacag                                                   19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 355
ugguuuaggg guucaucgg                                            19

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ccgaugaacc ccuaaacca                                            19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gguuuagggg uucaucggg                                            19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
cccgaugaac cccuaaacc                                            19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aggcaaugug ggacuuaaa                                            19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uuuaagtccc acauugccu                                            19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ggcaaugugg gacuuaaaa                    19

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
uuuuaagucc cacauugcc                    19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
gcaauguggg acuuaaaag                    19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
cuuuuaaguc ccacauugc                    19

<210> SEQ ID NO 365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365 ugaaaugga accuggcga                     19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ucgccagguu ccauuuuca                    19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
aaaauggaac cuggcgaaa                    19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uuucgccagg uuccauuuu                                                      19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
gagggagacc uugauacuu                                                      19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
aaguaucaag gucucccuc                                                      19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
agggagaccu ugauacuuu                                                      19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aaaguaucaa ggucucccu                                                      19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
agaccuugau acuuucaaa                                                      19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
uuugaaagua ucaaggucu                                                    19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
uugauacuuu caaaugccu                                                    19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
aggcauuuga aaguaucaa                                                    19

<210> SEQ ID NO 377
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
aaugccugag gggcucauc                                                    19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
gaugagcccc ucaggcauu                                                    19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
ugccugaggg gcucaucga                                                    19

<210> SEQ ID NO 380
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ucgaugagcc ccucaggca                                                19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gggcucaucg acgccugug                                                19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cacaggcguc gaugagccc                                                19

<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ggcucaucga cgccuguga                                                19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ucacaggcgu cgaugagcc                                                19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
aucgacgccu gugacaggg                                                19

<210> SEQ ID NO 386
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 386
cccugucaca ggcgucgau                                                19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
aggagccucc aagcaaauc                                                19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
gauuugcuug gaggcuccu                                                19

<210> SEQ ID NO 389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
auccauugcu cauccuagg                                                19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
ccuaggauga gcaauggau                                                19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
ucauccuagg aagacgggu                                                19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 392
acccgucuuc cuaggauga                                                    19

<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
cauccuagga agacggguu                                                    19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
aacccgucuu ccuaggaug                                                    19

<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
cuaggaagac ggguugaga                                                    19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ucucaacccg ucuuccuag                                                    19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
acggguugag aaucccuaa                                                    19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 398
uuagggauuc ucaacccgu                                                19

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
agaaucccua auuugaggg                                                19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
cccucaaauu agggauucu                                                19

<210> SEQ ID NO 401
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aaucccuaau uugaggguc                                                19

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
gacccucaaa uuagggauu                                                19

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
cccuaauuug agggucagu                                                19

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404

-continued acugacccuc aaauuaggg 19

<210> SEQ ID NO 405
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 405
cacucaaugc cucaauuug 19

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 406
caaauugagg cauugagug 19

<210> SEQ ID NO 407
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 407
acucaaugcc ucaauuugu 19

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 408
acaaauugag gcauugagu 19

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
uucugcauga cugagaguc 19

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
gacucucagu caugcagaa 19

```
<210> SEQ ID NO 411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
ucugcaugac ugagagucu                                                19

<210> SEQ ID NO 412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
agacucucag ucaugcaga                                                19

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gcaugacuga gagucucag                                                19

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
cugagacucu cagucaugc                                                19

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gacugagagu cucaguguu                                                19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
aacacugaga cucucaguc                                                19

<210> SEQ ID NO 417
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
gagucucagu guuggaacg                                                19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
cguuccaaca cugagacuc                                                19

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
cucaguguug gaacgggac                                                19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gucccguucc aacacugag                                                19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uuauuuugag ucugugagg                                                19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ccucacagac ucaaaauaa                                                19

<210> SEQ ID NO 423
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 423
auuuugaguc ugugagguc                                                19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
gaccucacag acucaaaau                                                19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
auauauugua guagauguu                                                19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
aacaucuacu acaauauau                                                19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
acuaaacuug cugcuuaau                                                19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
auuaagcagc aaguuuagu                                                19

<210> SEQ ID NO 429
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 429
gcugcuuaau gauuugcuc                                                    19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
gagcaaauca uuaagcagc                                                    19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
uuaaugauuu gcucacauc                                                    19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gaugugagca aaucauuaa                                                    19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
cacaucuagu aaaacaugg                                                    19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ccauguuuua cuagaugug                                                    19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 435
cuaguaaaac auggaguau                                                    19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
auacuccaug uuuuacuag                                                    19

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
cgacuacaag cgaauuacut t                                                 21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
aguaauucgc uuguagucgt t                                                 21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
uccuaggaag acggguugat t                                                 21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
```
ucaacccguc uuccuaggat t                                              21

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
gugccgacua caagcgaaut t                                              21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
auucgcuugu agucggcact t                                              21

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
ccgacuacaa gcgaauuact t                                              21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
guaauucgcu uguagucggt t                                              21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445

```
gccgacuaca agcgaauuat t                                              21
```

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446

```
uaauucgcuu guagucggct t                                              21
```

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447

```
guuuaggggu ucaucggggt t                                              21
```

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448

```
ccccgaugaa ccccuaaact t                                              21
```

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449

```
gauguuacaa uuuugucgct t                                              21
```

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450

-continued

```
gcgacaaaau uguaacauct t                                              21
```

<210> SEQ ID NO 451
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451

```
gcauuuacug ucacgguuct t                                              21
```

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452

```
gaaccgugac aguaaaugct t                                              21
```

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453

```
gagccaucuu auuaugccut t                                              21
```

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454

```
aggcauaaua agauggcuct t                                              21
```

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
agucucagug uuggaacggt t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456 ccguccaac acugagacut t                                               21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
cuuuuaggag auuagaucct t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
ggaucuaauc uccuaaaagt t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
auggaaccug gcgaaagcat t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460

-continued ugcuuucgcc agguuccaut t                                              21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
cuaccccaag gccgaaguct t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
gacuucggcc uugggguagt t                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
uggaaccugg cgaaagcagt t                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
cugcuuucgc cagguuccat t                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465

```
uauguggguag aguauggguat t                                            21
```

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466

```
uaccauacuc uaccacauat t                                              21
```

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467

```
uggucauccc agaacuacct t                                              21
```

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468

```
gguaguucug ggaugaccat t                                              21
```

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469

```
cauuuacugu cacgguucct t                                              21
```

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
ggaaccguga caguaaaugt t         21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
ggagccaucu uauuaugcct t         21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
ggcauaauaa gauggcucct t         21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
gacuacaagc gaauuacugt t         21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
caguaauucg cuuguaguct t         21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475

-continued cauacagcug aauuggucat t					21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
ugaccaauuc agcuguaugt t					21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
gcacuaauug ucuauugggt t					21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
cccaauagac aauuagugct t					21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
uuuagggguu caucggggct t					21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
gccccgauga acccuaaat t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
cucaaccugu gguuuagggt t                                             21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
cccuaaacca cagguugagt t                                             21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
ccuaauuuga gggucaguut t                                             21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
aacugacccu caaauuaggt t                                             21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485

-continued ucucaaccug ugguuuaggt t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
ccuaaaccac agguugagat t                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
uuuaggagau uagauccugt t                                              21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
caggaucuaa ucuccuaaat t                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
ccauugcuca uccuaggaat t                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
uuccuaggau gagcaauggt t    21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
cccaaggacc uauauguggt t    21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
ccacauauag guccuugggt t    21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
gacggguuga gaaucccuat t    21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
uagggauucu caacccguct t    21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
gcugcacuaa uugucuauut t 21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 496
aauagacaau uagugcagct t 21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 497
uuacugucac gguucccaat t 21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 498
uugggaaccg ugacaguaat t 21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 499
uuggucaucc cagaacuact t 21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 500

```
guaguucugg gaugaccaat t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
guggugccga cuacaagcgt t                                              21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
cgcuuguagu cggcaccact t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
ccgugggaug caggcaaugt t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
cauugccugc aucccacggt t                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
```

-continued ccaucuuauu augccuuggt t                                                21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
ccaaggcaua auaagauggt t                                                21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
ugaacgcauu uacugucact t                                                21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
gugacaguaa augcguucat t                                                21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
gguguagcac ugacauucat t                                                21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510

-continued ugaaugucag ugcuacacct t        21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
cugaacgcau uuacugucat t        21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
ugacaguaaa ugcguucagt t        21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
caaggaccua uaugugguat t        21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
uaccacauau agguccuugt t        21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
gagaccuuga uacuuucaat t         21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
uugaaaguau caaggucuct t         21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
gggcugagcg ugacaagagt t         21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
cucuugucac gcucagccct t         21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
uaugguggug ccgacuacat t         21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520

-continued

```
uguagucggc accaccauat t                                          21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
aagguucagc auaguagcut t                                          21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
agcuacuaug cugaaccuut t                                          21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
auccuaggaa gacggguugt t                                          21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
caacccgucu uccuaggaut t                                          21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
```

-continued auguuacaau uuugucgcct t            21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
ggcgacaaaa uuguaacaut t            21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
auuuacuguc acgguuccct t            21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
gggaaccgug acaguaaaut t            21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
cgcauuuacu gucacgguut t            21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530

```
aaccgugaca guaaaugcgt t                                       21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
agguucagca uaguagcuat t                                       21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
uagcuacuau gcugaaccut t                                       21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
caccagccgc gcuucuguct t                                       21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
gacagaagcg cggcuggugt t                                       21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
```

-continued cgcgcuucug uccgccugct t                                                21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
gcaggcggac agaagcgcgt t                                                21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
aagaugagga uauuugcugt t                                                21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
cagcaaauau ccucaucuut t                                                21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
cuuuauauuc augaccuact t                                                21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
guaggucaug aauauaaagt t    21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
auucaugacc uacuggcaut t    21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
augccaguag gucaugaaut t    21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
ucaugaccua cuggcauuut t    21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
aaaugccagu aggucaugat t    21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545

-continued

```
uacuggcauu ugcugaacgt t                                              21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
cguucagcaa augccaguat t                                              21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
cuggcauuug cugaacgcat t                                              21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
ugcguucagc aaaugccagt t                                              21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 549
auuugcugaa cgcauuuact t                                              21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
```

-continued guaaaugcgu ucagcaaaut t     21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
uuugcugaac gcauuuacut t     21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
aguaaaugcg uucagcaaat t     21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
gcugaacgca uuuacuguct t     21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554
gacaguaaau gcguucagct t     21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
uuuacuguca cgguucccat t    21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
ugggaaccgu gacaguaaat t    21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 557
acgguuccca aggaccuaut t    21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
auagguccuu gggaaccgut t    21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 559
cgguucccaa ggaccuauat t    21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560

-continued uauagguccu ugggaaccgt t                                             21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
gguucccaag gaccuauaut t                                             21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
auauaggucc uugggaacct t                                             21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
guucccaagg accuauaugt t                                             21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
cauauagguc cuugggaact t                                             21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
gaccuauaug ugguagagut t                                                    21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
acucuaccac auauagguct t                                                    21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
ugguagagua ugguagcaat t                                                    21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
uugcuaccau acucuaccat t                                                    21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
guaugguagc aauaugacat t                                                    21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
ugucauauug cuaccauact t    21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
ugguagcaau augacaauut t    21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
aauugucaua uugcuaccat t    21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
gguagcaaua ugacaauugt t    21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 574
caauugucau auugcuacct t    21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575

-continued agcaauauga caauugaaut t    21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
auucaauugu cauauugcut t    21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
caauaugaca auugaaugct t    21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
gcauucaauu gucauauugt t    21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
aauaugacaa uugaaugcat t    21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580

```
ugcauucaau ugucauauut t                                          21

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
auaugacaau ugaaugcaat t                                          21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
uugcauucaa uugucauaut t                                          21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
caauugaaug caaauuccct t                                          21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
gggaauuugc auucaauugt t                                          21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
```
ugaaugcaaa uucccaguat t                                               21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
uacugggaau uugcauucat t                                               21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
aaugcaaauu cccaguagat t                                               21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
ucuacuggga auuugcauut t                                               21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
aaaacaauua gaccuggcut t                                               21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590

-continued

```
agccaggucu aauuguuut t                                          21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
aaacaauuag accuggcugt t                                          21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
cagccagguc uaauuguuut t                                          21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
ggcugcacua auugucuaut t                                          21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
auagacaauu agugcagcct t                                          21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
```
ugcacuaauu gucuauuggt t    21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
ccaauagaca auuagugcat t    21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
uauugggaaa uggaggauat t    21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
uauccuccau uucccaauat t    21

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
caauuugugc auggagaggt t    21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600

-continued ccucuccaug cacaaauugt t    21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
ccugaagguu cagcauagut t    21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
acuaugcuga accuucaggt t    21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
ugaagguuca gcauaguagt t    21

<210> SEQ ID NO 604
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
cuacuaugcu gaaccuucat t    21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605

-continued gguucagcau aguagcuact t                                              21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
guagcuacua ugcugaacct t                                              21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
guucagcaua guagcuacat t                                              21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
uguagcuacu augcugaact t                                              21

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
uucagcauag uagcuacagt t                                              21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
cuguagcuac uaugcugaat t                                            21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
cauaguagcu acagacagat t                                            21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 612
ucugucugua gcuacuaugt t                                            21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
auaguagcua cagacagagt t                                            21

<210> SEQ ID NO 614
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
cucugucugu agcuacuaut t                                            21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
cuacagacag agggcccggt t                                               21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
ccgggcccuc ugucuguagt t                                               21

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
gcugcacuuc agaucacagt t                                               21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
cugugaucug aagugcagct t                                               21

<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
cugcacuuca gaucacagat t                                               21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
ucugugaucu gaagugcagt t    21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
ugcacuucag aucacagaut t    21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622
aucugugauc ugaagugcat t    21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
gcacuucaga ucacagaugt t    21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 624
caucugugau cugaagugct t    21

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 625

```
aaauugcagg augcaggggt t                                            21
```

```
<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 626
ccccugcauc cugcaauuut t                                            21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
caggaugcag ggguguacct t                                            21

<210> SEQ ID NO 628
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 628
gguacacccc ugcauccugt t                                            21

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
ggaugcaggg guguaccgct t                                            21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 630
```
gcgguacacc ccugcaucct t								21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
guaccgcugc augaucagct t								21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 632
gcugaucaug cagcgguact t								21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 633
accgcugcau gaucagcuat t								21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 634
uagcugauca ugcagcggut t								21

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 635
augaucagcu augguggugt t                                          21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 636
caccaccaua gcugaucaut t                                          21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 637
gcuauggugg ugccgacuat t                                          21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 638
uagucggcac caccauagct t                                          21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
ugccgacuac aagcgaauut t                                          21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 640
aauucgcuug uagucggcat t                                              21

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 641
agcgaauuac ugugaaagut t                                              21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 642
acuuucacag uaauucgcut t                                              21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 643
gcgaauuacu gugaaaguct t                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
gacuuucaca guaauucgct t                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 645
cgaauuacug ugaaagucat t                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 646
ugacuuucac aguaauucgt t                                              21

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
auuacuguga aagucaaugt t                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 648
cauugacuuu cacaguaaut t                                              21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
uacugugaaa gucaaugcct t                                              21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650

-continued ggcauugacu uucacaguat t					21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
aaagucaaug ccccauacat t					21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 652
uguauggggc auugacuuut t					21

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
gucaaugccc cauacaacat t					21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
uguuguaugg ggcauugact t					21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655

```
aauuugguu guggauccat t                                          21
```

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656

```
uggauccaca accaaaaauut t                                        21
```

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657

```
auuugguug uggauccagt t                                          21
```

<210> SEQ ID NO 658
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 658

```
cuggauccac aaccaaaaut t                                         21
```

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659

```
agucaccucu gaacaugaat t                                         21
```

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660

```
uucauguuca gaggugacut t                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
accucugaac augaacugat t                                              21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
ucaguucaug uucagaggut t                                              21

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
ccucugaaca ugaacugact t                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
gucaguucau guucagaggt t                                              21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
```
ugaacaugaa cugacaugut t     21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
acaugucagu ucauguucat t     21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
acaugaacug acaugucagt t     21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
cugacauguc aguucaugut t     21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
caugaacuga caugucaggt t     21

<210> SEQ ID NO 670
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670

-continued

```
ccugacaugu caguucaugt t                                             21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
ugaacugaca ugucaggcut t                                             21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
agccugacau gucaguucat t                                             21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
gaacugacau gucaggcugt t                                             21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
cagccugaca ugucaguuct t                                             21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
```

```
gacaugucag gcugagggct t                                           21
```

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676

```
gcccucagcc ugacauguct t                                           21
```

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 677

```
ugucaggcug agggcuacct t                                           21
```

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678

```
gguagcccuc agccugacat t                                           21
```

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679

```
uaccccaagg ccgaagucat t                                           21
```

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
ugacuucggc cuugggguat t                                              21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
aaggccgaag ucaucuggat t                                              21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
uccagaugac uucggccuut t                                              21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
cgaagucauc uggacaagct t                                              21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
gcuuguccag augacuucgt t                                              21

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 685
caucuggaca agcagugact t    21

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 686
gucacugcuu guccagaugt t    21

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 687
agcagugacc aucaaguect t    21

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
ggacuugaug gucacugcut t    21

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
ucaaguccug agugguaagt t    21

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690

-continued cuuaccacuc aggacuugat t                                               21

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 691
gaaucaacac aacaacuaat t                                               21

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
uuaguuguug uguugauuct t                                               21

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
aaucaacaca acaacuaaut t                                               21

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
auuaguuguu guguugauut t                                               21

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
uucuacugca cuuuuaggat t                                              21

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
uccuaaaagu gcaguagaat t                                              21

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
gcacuuuuag gagauuagat t                                              21

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
ucuaaucucc uaaaagugct t                                              21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
uuuuaggaga uuagauccut t                                              21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700

```
aggaucuaau cuccuaaaat t                                           21

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 701
uuaggagauu agauccugat t                                           21

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 702
ucaggaucua aucuccuaat t                                           21

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 703
uaggagauua gauccugagt t                                           21

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 704
cucaggaucu aaucuccuat t                                           21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 705
```

-continued

```
aggagauuag auccugaggt t                                              21

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 706
ccucaggauc uaaucuccut t                                              21

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 707
ggagauuaga uccugaggat t                                              21

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 708
uccucaggau cuaaucucct t                                              21

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 709
aaaccauaca gcugaauugt t                                              21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 710
```

-continued caauucagcu guaugguuut t                        21

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 711
aaccauacag cugaauuggt t                        21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 712
ccaauucagc uguaugguut t                        21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
ccauacagcu gaauugguct t                        21

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 714
gaccaauuca gcuguauggt t                        21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715

-continued auacagcuga auuggucaut t         21

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 716
augaccaauu cagcuguaut t         21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 717
gcugaauugg ucaucccagt t         21

<210> SEQ ID NO 718
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
cugggaugac caauucagct t         21

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 719
ggucauccca gaacuaccut t         21

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720

-continued agguaguucu gggaugacct t 21

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721
uggcacaucc uccaaaugat t 21

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 722
ucauuuggag gaugugccat t 21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
ugaaaggacu cacuugguat t 21

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 724
uaccaaguga guccuuucat t 21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
aggacucacu ugguaauuct t                                              21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 726
gaauuaccaa gugaguccut t                                              21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
gacucacuug guaauucugt t                                              21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
cagaauuacc aagugaguct t                                              21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 729
ucacuuggua auucugggat t                                              21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730

```
ucccagaauu accaagugat t                                              21
```

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731

```
gguaauucug ggagccauct t                                              21
```

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732

```
gauggcuccc agaauuacct t                                              21
```

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733

```
guaauucugg gagccaucut t                                              21
```

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734

```
agauggcucc cagaauuact t                                              21
```

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
ucugggagcc aucuuauuat t					21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
uaauaagaug gcucccagat t					21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
cugggagcca ucuuauuaut t					21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
auaauaagau ggcucccagt t					21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
ugggagccau cuuauuaugt t					21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 740
cauaauaaga uggcucccat t                                              21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 741
gggagccauc uuauuaugct t                                              21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 742
gcauaauaag auggcuccct t                                              21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
agccaucuua uuaugccuut t                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
aaggcauaau aagauggcut t                                              21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
aucuuauuau gccuuggugt t                                           21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
caccaaggca uaauaagaut t                                           21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 747
uauuaugccu ugguguagct t                                           21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748
gcuacaccaa ggcauaaauat t                                          21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
auuaugccuu gguguagcat t                                           21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
ugcuacacca aggcauaaut t                                21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 751
ugccuuggug uagcacugat t                                21

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
ucagugcuac accaaggcat t                                21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
ugguguagca cugacauuct t                                21

<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
gaaugucagu gcuacaccat t                                21

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 755

```
guagcacuga cauucaucut t                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 756
agaugaaugu cagugcuact t                                              21

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 757
cugacauuca ucuuccguut t                                              21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 758
aacggaagau gaaugucagt t                                              21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 759
agggagaaug auggaugugt t                                              21

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 760
```

```
cacauccauc auucucccut t                                              21
```

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 761

```
uggcauccaa gauacaaact t                                              21
```

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 762

```
guuuguaucu uggaugccat t                                              21
```

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 763

```
ggcauccaag auacaaacut t                                              21
```

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 764

```
aguuuguauc uuggaugcct t                                              21
```

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765

| gcauccaaga uacaaacuct t | 21 |

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766

| gaguuuguau cuuggaugct t | 21 |

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767

| caaagugaua cacauuggt t | 21 |

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768

| ccaaaugugu aucacuuugt t | 21 |

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769

| gugauacaca uuuggaggat t | 21 |

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 770
uccuccaaau guguaucact t					21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 771
acacauuugg aggagacgut t					21

<210> SEQ ID NO 772
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 772
acgucuccuc caaaugugut t					21

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
acauuuggag gagacguaat t					21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 774
uuacgucucc uccaaaugut t					21

<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 775

-continued cauuuggagg agacguaaut t                                     21

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 776
auuacgucuc cuccaaaugt t                                     21

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 777
ggaggagacg uaauccagct t                                     21

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
gcuggauuac gucuccucct t                                     21

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779
acguaaucca gcauuggaat t                                     21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780
uuccaaugcu ggauuacgut t    21

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 781
aaccuguggu uuaggggut t    21

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 782
aaccccuaaa ccacagguut t    21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 783
ccuguggtuu aggguucat t    21

<210> SEQ ID NO 784
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
ugaaccccua aaccacaggt t    21

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785

-continued

```
cuguggguuua gggguucaut t                                        21

<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 786
augaaccccu aaaccacagt t                                         21

<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
ugguuuaggg guucaucggt t                                         21

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 788
ccgaugaacc ccuaaaccat t                                         21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
gguuuagggg uucaucgggt t                                         21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
```
cccgaugaac cccuaaacct t                                              21

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 791
aggcaaugug ggacuuaaat t                                              21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 792
uuuaaguccc acauugccut t                                              21

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 793
ggcaaugugg gacuuaaaat t                                              21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 794
uuuuaagucc cacauugcct t                                              21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 795 gcaaugugggg acuuaaaagt t                                              21

<210> SEQ ID NO 796
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 796
cuuuuaaguc ccacauugct t                                               21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 797
ugaaaaugga accuggcgat t                                               21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 798
ucgccagguu ccauuuucat t                                               21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 799
aaaauggaac cuggcgaaat t                                               21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 800

-continued

```
uuucgccagg uuccauuuut t                                              21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 801
gagggagacc uugauacuut t                                              21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 802
aaguaucaag gucucccuct t                                              21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 803
agggagaccu ugauacuuut t                                              21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 804
aaaguaucaa ggucucccut t                                              21

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 805
```
agaccuugau acuuucaaat t                                              21

<210> SEQ ID NO 806
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 806
uuugaaagua ucaaggucut t                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 807
uugauacuuu caaaugccut t                                              21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 808
aggcauuuga aaguaucaat t                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 809
aaugccugag gggcucauct t                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 810

-continued gaugagcccc ucaggcauut t					21

<210> SEQ ID NO 811
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 811
ugccugaggg gcucaucgat t					21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 812
ucgaugagcc ccucaggcat t					21

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 813
gggcucaucg acgccugugt t					21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 814
cacaggcguc gaugagccct t					21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 815

-continued ggcucaucga cgccugugat t                                21

<210> SEQ ID NO 816
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 816
ucacaggcgu cgaugagcct t                                21

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
aucgacgccu gugacagggt t                                21

<210> SEQ ID NO 818
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
cccugucaca ggcgucgaut t                                21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
aggagccucc aagcaaauct t                                21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820

-continued gauuugcuug gaggcuccut t                                              21

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 821
auccauugcu cauccuaggt t                                              21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 822
ccuaggauga gcaauggaut t                                              21

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 823
ucauccuagg aagacgggut t                                              21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 824
acccgucuuc cuaggaugat t                                              21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 825

-continued cauccuagga agacggguut t          21

<210> SEQ ID NO 826
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 826
aacccgucuu ccuaggaugt t          21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 827
cuaggaagac ggguugagat t          21

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 828
ucucaacccg ucuuccuagt t          21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829 acgguugag aaucccuaat t          21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830

-continued uuagggauuc ucaacccgut t         21

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 831 agaauccccua auuugagggt t         21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 832
cccucaaauu agggauucut t         21

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 833
aaucccuaau uugaggguct t         21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 834
gacccucaaa uuagggauut t         21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 835
cccuaauuug agggucagut t				21

<210> SEQ ID NO 836
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 836
acugacccuc aaauuagggt t				21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 837
cacucaaugc cucaauuugt t				21

<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 838
caaauugagg cauugagugt t				21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 839
acucaaugcc ucaauuugut t				21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 840

```
acaaauugag gcauugagut t                                              21
```

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841

```
uucugcauga cugagaguct t                                              21
```

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 842

```
gacucucagu caugcagaat t                                              21
```

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 843

```
ucugcaugac ugagagucut t                                              21
```

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 844

```
agacucucag ucaugcagat t                                              21
```

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 845
gcaugacuga gagucucagt t                                     21

<210> SEQ ID NO 846
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 846
cugagacucu cagucaugct t                                     21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 847
gacugagagu cucaguguut t                                     21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
aacacugaga cucucaguct t                                     21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
gagucucagu guuggaacgt t                                     21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850

-continued

```
cguuccaaca cugagacuct t                                              21

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
cucaguguug gaacgggact t                                              21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
gucccguucc aacacugagt t                                              21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
uuauuuugag ucugugaggt t                                              21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
ccucacagac ucaaaauaat t                                              21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 855
```

-continued auuuugaguc ugugagguct t            21

<210> SEQ ID NO 856
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 856
gaccucacag acucaaaaut t            21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 857
auauauugua guagauguut t            21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 858
aacaucuacu acaauauaut t            21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
acuaaacuug cugcuuaaut t            21

<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 860
auuaagcagc aaguuuagut t                          21

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
gcugcuuaau gauuugcuct t                          21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
gagcaaauca uuaagcagct t                          21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
uuaaugauuu gcucacauct t                          21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
gaugugagca aaucauuaat t                          21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 865

```
cacaucuagu aaaacauggt t                                              21
```

<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 866

```
ccauguuuua cuagaugugt t                                              21
```

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867

```
cuaguaaaac auggaguaut t                                              21
```

<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868

```
auacuccaug uuuuacuagt t                                              21
```

<210> SEQ ID NO 869
<211> LENGTH: 1553
<212> TYPE: DNA
<213> ORGANISM: Homo sapiens

<400> SEQUENCE: 869

```
cgaggctccg caccagccgc gcttctgtcc gcctgcaggg cattccagaa agatgaggat    60
atttgctgtc tttatattca tgacctactg gcatttgctg aacgcattta ctgtcacggt   120
tcccaaggac ctatatgtgg tagagtatgg tagcaatatg acaattgaat gcaaattccc   180
agtagaaaaa caattagacc tggctgcact aattgtctat tgggaaatgg aggataagaa   240
cattattcaa tttgtgcatg agaggaaga cctgaaggtt cagcatagta gctacagaca   300
gagggcccgg ctgttgaagg accagctctc cctgggaaat gctgcacttc agatcacaga   360
tgtgaaattg caggatgcag gggtgtaccg ctgcatgatc agctatggtg gtgccgacta   420
caagcgaatt actgtgaaag tcaatgcccc atacaacaaa atcaaccaaa gaattttggt   480
tgtggatcca gtcacctctg aacatgaact gacatgtcag gctgagggct accccaaggc   540
cgaagtcatc tggacaagca gtgaccatca agtcctgagt ggtaagacca ccaccaccaa   600
ttccaagaga gaggagaagc ttttcaatgt gaccagcaca ctgagaatca acacaacaac   660
```

```
taatgagatt ttctactgca cttttaggag attagatcct gaggaaaacc atacagctga    720
attggtcatc ccagaactac ctctggcaca tcctccaaat gaaaggactc acttggtaat    780
tctgggagcc atcttattat gccttggtgt agcactgaca ttcatcttcc gtttaagaaa    840
agggagaatg atggatgtga aaaaatgtgg catccaagat acaaactcaa agaagcaaag    900
tgatacacat ttggaggaga cgtaatccag cattggaact tctgatcttc aagcagggat    960
tctcaacctg tggtttaggg gttcatcggg gctgagcgtg acaagaggaa ggaatgggcc   1020
cgtgggatgc aggcaatgtg ggacttaaaa ggcccaagca ctgaaaatgg aacctggcga   1080
aagcagagga ggagaatgaa gaaagatgga gtcaaacagg gagcctggag ggagaccttg   1140
atactttcaa atgcctgagg ggctcatcga cgcctgtgac agggagaaag gatacttctg   1200
aacaaggagc ctccaagcaa atcatccatt gctcatccta ggaagacggg ttgagaatcc   1260
ctaatttgag ggtcagttcc tgcagaagtg ccctttgcct ccactcaatg cctcaatttg   1320
ttttctgcat gactgagagt ctcagtgttg aacgggaca gtatttatgt atgagttttt   1380
cctatttatt ttgagtctgt gaggtcttct tgtcatgtga gtgtggttgt gaatgatttc   1440
ttttgaagat atattgtagt agatgttaca attttgtcgc caaactaaac ttgctgctta   1500
atgatttgct cacatctagt aaaacatgga gtatttgtaa aaaaaaaaa aaa           1553

<210> SEQ ID NO 870
<211> LENGTH: 3653
<212> TYPE: DNA
<213> ORGANISM: Mus musculus

<400> SEQUENCE: 870
gaaatcgtgg tccccaagcc tcatgccagg ctgcacttgc acgtcgcggg ccagtctcct     60
cgcctgcaga tagttcccaa acatgagga tatttgctgg cattatattc acagcctgct    120
gtcacttgct acgggcgttt actatcacgg ctccaaagga cttgtacgtg gtggagtatg    180
gcagcaacgt cacgatggag tgcagattcc ctgtagaacg ggagctggac ctgcttgcgt    240
tagtggtgta ctgggaaaag gaagatgagc aagtgattca gttgtgtgca ggagaggagg    300
accttaagcc tcagcacagc aacttcaggg ggagagcctc gctgccaaag gaccagcttt    360
tgaagggaaa tgctgccctt cagatcacag acgtcaagct gcaggacgca ggcgtttact    420
gctgcataat cagctacggt ggtgcggact acaagcgaat cacgctgaaa gtcaatgccc    480
cataccgcaa aatcaaccag agaatttccg tggatccagc cacttctgag catgaactaa    540
tatgtcaggc cgagggttat ccagaagctg aggtaatctg dacaaacagt gaccaccaac    600
ccgtgagtgg gaagagaagt gtcaccactt cccggacaga ggggatgctt ctcaatgtga    660
ccagcagtct gagggtcaac gccacagcga atgatgtttt ctactgtacg ttttggagat    720
cacagccagg gcaaaaccac acagcggagc tgatcatccc agaactgcct gcaacacatc    780
ctccacagaa caggactcac tgggtgcttc tgggatccat cctgttgttc ctcattgtag    840
tgtccacggt cctcctcttc ttgagaaaac aagtgagaat gctagatgtg gagaaatgtg    900
gcgttgaaga tacaagctca aaaaaccgaa atgatacaca attcgaggag cgtaagcag    960 tgttgaaccc tctgatcgtc gattggcagc ttgtggtctg tgaaagaaag ggcccatggg   1020
acatgagtcc aaagactcaa gatggaacct gaggagaga accagaaaag tgttgggaga   1080
ggagcctgga acaacggaca ttttttccag ggagacactg ctaagcaagt tgcccatcag   1140
tcgtcttggg aaatggattg agggttcctg gcttagcagc tggtccttgc acagtgacct   1200
tttcctctgc tcagtgccgg gatgagagat ggagtcatga gtgttgaaga ataagtgcct   1260
```

```
tctatttatt ttgagtctgt gtgttctcac tttgggcatg taattatgac tggtgaattc    1320
tgacgacatg atagatctta agatgtagtc accaaactca actgctgctt agcatcctcc    1380
gtaactactg atacaagcag ggaacacaga ggtcacctgc ttggtttgac aggctcttgc    1440
tgtctgactc aaataatctt tatttttcag tcctcaaggc tcttcgatag cagttgttct    1500
gtatcagcct tataggtgtc aggtatagca ctcaacatct catctcatta caatagcaac    1560
cctcatcacc atagcaacag ctaacctctg ttatcctcac ttcatagcca ggaagctgag    1620
cgactaagtc acttgcccac agagtatcag ctctcagatt tctgttcttc agccactgtc    1680 cttcaggat agaatttgtc gttaagaaat taatttaaaa actgattatt gagtagcatt     1740
gtatatcaat cacaacatgc cttgtgcact gtgctggcct ctgagcataa agatgtacgc    1800
cggagtaccg gtcggacatg tttatgtgtg ttaaatactc agagaaatgt tcattaacaa    1860
ggagcttgca ttttagagac actggaaagt aactccagtt cattgtctag cattacattt    1920
acctcatttg ctatccttgc catacagtct cttgttctcc atgaagtgtc atgaatcttg    1980
ttgaatagtt cttttatttt ttaaatgttt ctatttaaat gatattgaca tctgaggcga    2040
tagctcagtt ggtaaaaccc tttcctcaca agtgtgaaac cctgagtctt atccctagaa    2100
cccacataaa aaacagttgc gtatgtttgt gcatgctttt gatcccagca ctagggaggc    2160
agaggcaggc agatcctgag ctctcattga ccacccagcc tagcctacat ggttagctcc    2220
aggcctacag gagctggcag agcctgaaaa acgatgccta gacacacaca cacacacaca    2280
cacacacaca cacacacaca caccatgt actcatagac ctaagtgcac cctcctacac     2340
atgcacacac atacaattca aacacaaatc aacagggaat tgtctcagaa tggtcccaa    2400 gacaaagaag aagaaaaaca ccaaaccagc tctattccct cagcctatcc tctctactcc    2460
ttcctagaag caactactat tgttttttgta tataaattta cccaacgaca gttaatatgt   2520
agaatatata ttaaagtgtc tgtcaatata tattatctct ttctttcttt cttcctttct    2580
ttctttcttt ctttctttct ttctttcttct cttctttct ttcttccttc cttccttcct   2640
tccttccttc cttccttcct ttctttcttt ctttctttt ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaagggga gccttgtttg     3000 tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240
tctgggggga ggaaaggagg aggaacccag aactttctta cagttttcct tgttctgtca    3300
catgtcaaga ctgaaggaac aggctgggct acgtagtgag atcctgtctc aaaggaaaga    3360
cgagcatagc cgaaccccg gtggaacccc ctctgttacc tgttcacaca agcttattga     3420
tgagtctcat gttaatgtct tgtttgtatg aagtttaaga aaatatcggg ttgggcaaca    3480 cattctatttt attcatttta tttgaaatct taatgccatc tcatggtgtt ggattggtgt    3540
ggcactttat tcttttgtgt tgtgtataac cataaatttt attttgcatc agattgtcaa    3600
tgtattgcat taatttaata aatattttta tttattaaaa aaaaaaaaaa aaa           3653
```

<210> SEQ ID NO 871
<211> LENGTH: 1080
<212> TYPE: DNA
<213> ORGANISM: Rattus norvegicus

<400> SEQUENCE: 871

| | | | | |
|---|---|---|---|---|
| atgaggatat | ttgctgtcct | tatagtcaca | gcctgcagtc acgtgctagc ggcatttacc | 60 |
| atcacagctc | caaaggacct | gtacgtggtg | gagtatggca gcaatgtcac gatggaatgc | 120 |
| agattcccag | tagaacagaa | attggacctg | cttgccttag tggtgtactg ggaaaaggaa | 180 |
| gacaaggaag | ttattcagtt | tgtggaggga | gaggaggacc tgaagcctca acacagcagc | 240 |
| ttcaggggga | gagccttctt | gccaaaggac | cagcttttga aggggaacgc ggtgcttcag | 300 |
| atcacagatg | tcaagctgca | ggacgcaggt | gtctactgct gcatgatcag ctatggtgga | 360 |
| gcggactaca | agcgaatcac | attgaaagtc | aacgctccat accgcaaaat caaccaaaga | 420 |
| atttccatgg | atccagccac | ttctgagcat | gaactaatgt gccaggctga gggttaccca | 480 |
| gaagccgaag | tgatctggac | aaacagtgac | caccagtccc tgagtgggga acaactgtc | 540 |
| accacttccc | agactgagga | gaagcttctc | aacgtgacca gcgttctgag ggtcaacgca | 600 |
| acagctaatg | atgttttcca | ctgtacgttc | tggagagtac actcagggga gaaccacacg | 660 |
| gctgaactga | tcatcccaga | actgcctgta | ccacgtctcc cacataacag gacacactgg | 720 |
| gtactcctgg | gatccgtcct | tttgttcctc | atcgtgqqgt tcaccgtctt cttctgcttg | 780 |
| agaaaacaag | tgagaatgct | agatgtggaa | aaatgcggct tcgaagatag aaattcaaag | 840 |
| aaccgaaatg | ttcgaggaga | cgtaagcagt | gttgaaccct ctgagcctcg aggcgggatt | 900 |
| ggcagcttgt | ggtctgtgaa | agaaagggcc | cgtgggacat gggtccaggg actcaaaaat | 960 |
| ggaaccggag | aggagaagag | aacaaagaaa | gtgttggaag aggagcctgg gacgaaagac | 1020 |
| atttctacag | gagacactgc | taagcaagtt | acccatcagt catctcgggc aataagttga | 1080 |

<210> SEQ ID NO 872
<211> LENGTH: 1080
<212> TYPE: DNA
<213> ORGANISM: Rattus norvegicus

<400> SEQUENCE: 872

| | | | | |
|---|---|---|---|---|
| atgaggatat | ttgctgtcct | tatagtcaca | gcctgcagtc acgtgctagc ggcatttacc | 60 |
| atcacagctc | caaaggacct | gtacgtggtg | gagtatggca gcaatgtcac gatggaatgc | 120 |
| agattcccag | tagaacagaa | attggacctg | cttgccttag tggtgtactg ggaaaaggaa | 180 |
| gacaaggaag | ttattcagtt | tgtggaggga | gaggaggacc tgaagcctca acacagcagc | 240 |
| ttcaggggga | gagccttctt | gccaaaggac | cagcttttga aggggaacgc ggtgcttcag | 300 |
| atcacagatg | tcaagctgca | ggacgcaggt | gtctactgct gcatgatcag ctatggtgga | 360 |
| gcggactaca | agcgaatcac | attgaaagtc | aacgctccat accgcaaaat caaccaaaga | 420 |
| atttccatgg | atccagccac | ttctgagcat | gaactaatgt gccaggctga gggttaccca | 480 |
| gaagccgaag | tgatctggac | aaacagtgac | caccagtccc tgagtgggga acaactgtc | 540 |
| accacttccc | agactgagga | gaagcttctc | aacgtgacca gcgttctgag ggtcaacgca | 600 |
| acagctaatg | atgttttcca | ctgtacgttc | tggagagtac actcagggga gaaccacacg | 660 |
| gctgaactga | tcatcccaga | actgcctgta | ccacgtctcc cacataacag gacacactgg | 720 |
| gtactcctgg | gatccgtcct | tttgttcctc | atcgtgqqgt tcaccgtctt cttctgcttg | 780 |
| agaaaacaag | tgagaatgct | agatgtggaa | aaatgcggct tcgaagatag aaattcaaag | 840 |

```
aaccgaaatg ttcgaggaga cgtaagcagt gttgaaccct ctgagcctcg aggcgggatt    900
ggcagcttgt ggtctgtgaa agaaagggcc cgtgggacat gggtccaggg actcaaaaat    960
ggaaccggag aggagaagag aacaaagaaa gtgttggaag aggagcctgg gacgaaagac   1020
atttctacag gagacactgc taagcaagtt acccatcagt catctcgggc aataagttga   1080
```

<210> SEQ ID NO 873
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25

<210> SEQ ID NO 874
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 874

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 875
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Ala Leu Glu Ala Leu Ala Glu Ala Leu Glu Ala Leu Ala Glu Ala
1               5                   10                  15

<210> SEQ ID NO 876

<400> SEQUENCE: 876

000

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 877
ugaauauauc uuaacgccat t                                                21

```
<210> SEQ ID NO 878
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
gcuagaaaga auccugggut t                                              21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 879
ggagcuacug cauguugaut t                                              21

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
aguccucaua ucaaauacat t                                              21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 881
ucauaucaaa uacagaacat t                                              21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 882
cauaucaaau acagaacaut t                                              21
```

```
<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
uccugcuaau guugagccut t                                              21

<210> SEQ ID NO 884
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
gcuaauguug agccuggaat t                                              21

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
ucccuaagga acuguacaut t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
cccuaaggaa cuguacauat t                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 887
uacauaauag agcauggcat t                                              21
```

-continued

```
<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 888
auaauagagc auggcagcat t                                              21

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 889
uaauagagca uggcagcaat t                                              21

<210> SEQ ID NO 890
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 890
aauagagcau ggcagcaaut t                                              21

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
gacccuggaa ugcaacuuut t                                              21

<210> SEQ ID NO 892
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 892
caauaacagc caguuugcat t                                              21
```

```
<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
auaacagcca guuugcaaat t                                           21

<210> SEQ ID NO 894
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
uccacauacc ucaaguccat t                                           21

<210> SEQ ID NO 895
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 895
accaaugcau aaucaucuat t                                           21

<210> SEQ ID NO 896
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
ggacuacaag uaccugacut t                                           21

<210> SEQ ID NO 897
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
acuacaagua ccugacucut t                                           21
```

```
<210> SEQ ID NO 898
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
gucaaagcuu ccuacaggat t                                             21

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 899
cacucacauc cuaaagguut t                                             21

<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
ucacauccua aagguuccat t                                             21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
uggcguuaag auauauucat t                                             21

<210> SEQ ID NO 902
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
acccaggauu cuuucuagct t                                             21
```

```
<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
aucaacaugc aguagcucct t                                              21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
uguauuugau augaggacut t                                              21

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
uguucuguau uugauaugat t                                              21

<210> SEQ ID NO 906
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
auguucugua uuugauaugt t                                              21

<210> SEQ ID NO 907
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
aggcucaaca uuagcaggat t                                              21
```

```
<210> SEQ ID NO 908
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
uuccaggcuc aacauuagct t                                                   21

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 909
auguacaguu ccuuagggat t                                                   21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 910
uauguacagu uccuuagggt t                                                   21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 911
ugccaugcuc uauuauguat t                                                   21

<210> SEQ ID NO 912
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 912
ugcugccaug cucuauuaut t                                                   21
```

```
<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 913
uugcugccau gcucuauuat t                                                   21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
auugcugcca ugcucuauut t                                                   21

<210> SEQ ID NO 915
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
aaaguugcau uccaggguct t                                                   21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
ugcaaacugg cuguuauugt t                                                   21

<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
uuugcaaacu ggcuguuaut t                                                   21
```

```
<210> SEQ ID NO 918
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
uggacuugag guauguggat t                                              21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 919
uagaugauua ugcauuggut t                                              21

<210> SEQ ID NO 920
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
agucagguac uuguagucct t                                              21

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
agagucaggu acuuguagut t                                              21

<210> SEQ ID NO 922
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 922
uccuguagga agcuuugact t                                              21
```

```
<210> SEQ ID NO 923
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
aaccuuuagg augugagugt t                                              21

<210> SEQ ID NO 924
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 924
uggaaccuuu aggaugugat t                                              21

<210> SEQ ID NO 925
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Arg Arg Lys Arg Arg Arg
1               5
```